US008926670B2

(12) United States Patent
Jackson

(10) Patent No.: US 8,926,670 B2
(45) Date of Patent: *Jan. 6, 2015

(54) POLYAXIAL BONE SCREW ASSEMBLY

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/815,750

(22) Filed: Mar. 15, 2013

(65) Prior Publication Data

US 2013/0325075 A1    Dec. 5, 2013

Related U.S. Application Data

(63) Continuation-in-part of application No. 12/800,314, filed on May 12, 2010, now Pat. No. 8,398,682, which is a continuation-in-part of application No. 12/009,130, filed on Jan. 16, 2008, now Pat. No. 8,257,398, which is a continuation-in-part of application No. 10/818,554, filed on Apr. 5, 2004, now Pat. No. 7,662,175, which is a continuation of application No. 10/464,633, filed on Jun. 18, 2003, now Pat. No. 6,716,214, and a continuation-in-part of application No. 10/651,003, filed on Aug. 28, 2003, now Pat. No. 8,137,386.

(60) Provisional application No. 61/178,840, filed on May 15, 2009.

(51) Int. Cl.
*A61B 17/70* (2006.01)

(52) U.S. Cl.
CPC .......... *A61B 17/7032* (2013.01); *A61B 17/7037* (2013.01); *A61B 17/708* (2013.01); *A61B 17/704* (2013.01)
USPC ........................................................ 606/264

(58) Field of Classification Search
USPC ......... 606/246, 253, 256, 264–270, 278, 279, 606/301
See application file for complete search history.

(56) References Cited

U.S. PATENT DOCUMENTS

| 154,864 A | 9/1874 | Harvey |
| 791,548 A | 6/1905 | Fischer |

(Continued)

FOREIGN PATENT DOCUMENTS

| AU | 2012203959 | 8/2012 |
| DE | 373809 | 4/1923 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Pedro Philogene
*Assistant Examiner* — David Comstock
(74) *Attorney, Agent, or Firm* — John C. McMahon

(57) ABSTRACT

A polyaxial bone screw assembly includes a shank body having an upper head portion with a mating segment and a first partial spherical surface, a retainer structure being mateable with the mating segment of the upper head portion, the retainer structure having a second partial spherical surface such that when mated, the first and second partial spherical surfaces form a spherical ball member, a receiver defining an open channel and having a base with a seating surface partially defining a cavity with a shaped wall, the open channel communicating with the cavity, the cavity communicating with an exterior of the base through an opening sized and shaped to receive the shank upper head portion therethrough, and a bushing sized and shaped to fit within open channel and cavity and lock in recesses on interior of receiver.

8 Claims, 15 Drawing Sheets

(56) References Cited

U.S. PATENT DOCUMENTS

| | | |
|---|---|---|
| 1,300,275 A | 4/1919 | Johnson |
| 1,330,673 A | 2/1920 | Anderson |
| 1,472,464 A | 10/1923 | Ellison |
| 2,083,092 A | 6/1937 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,445,978 A | 7/1948 | Stellin |
| 2,531,892 A | 11/1950 | Reese |
| 2,532,815 A | 12/1950 | Kindsvatter et al. |
| 2,537,029 A | 1/1951 | Cambern |
| 2,553,337 A | 5/1951 | Shafer |
| 2,778,265 A | 1/1957 | Brown |
| 2,813,450 A | 11/1957 | Dzus |
| 2,877,681 A | 3/1959 | Brown |
| 2,927,332 A | 3/1960 | Moore |
| 2,969,250 A | 1/1961 | Kull |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,444,775 A | 5/1969 | Hills |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Gryctko |
| 3,989,284 A | 11/1976 | Blose |
| 3,997,138 A | 12/1976 | Crock et al. |
| 4,013,071 A | 3/1977 | Rosenberg |
| 4,033,139 A | 7/1977 | Frederick |
| 4,041,939 A | 8/1977 | Hall |
| 4,103,422 A | 8/1978 | Weiss et al. |
| 4,190,091 A | 2/1980 | Colognori |
| 4,269,246 A | 5/1981 | Larson et al. |
| 4,347,845 A | 9/1982 | Mayfield |
| 4,369,769 A | 1/1983 | Edwards |
| 4,373,754 A | 2/1983 | Bollfrass et al. |
| 4,409,968 A | 10/1983 | Drummond |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen |
| 4,577,448 A | 3/1986 | Howorth |
| 4,600,224 A | 7/1986 | Blose |
| 4,600,225 A | 7/1986 | Blose |
| 4,641,636 A | 2/1987 | Cotrel |
| 4,653,481 A | 3/1987 | Howland et al. |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee et al. |
| 4,877,020 A | 10/1989 | Vich |
| 4,887,596 A | 12/1989 | Sherman |
| 4,917,606 A | 4/1990 | Miller |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,042,982 A | 8/1991 | Harms et al. |
| 5,056,492 A | 10/1991 | Banse |
| 5,067,428 A | 11/1991 | Dickerson et al. |
| 5,067,955 A | 11/1991 | Cotrel |
| 5,073,074 A | 12/1991 | Corrigan et al. |
| 5,084,048 A | 1/1992 | Jacob et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,679 A | 1/1993 | Lin |
| 5,176,680 A | 1/1993 | Vignaud et al. |
| 5,180,393 A | 1/1993 | Commarmond |
| 5,201,734 A | 4/1993 | Cozad et al. |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,263,953 A | 11/1993 | Bagby |
| 5,275,601 A | 1/1994 | Gogolewski et al. |
| 5,282,707 A | 2/1994 | Palm |
| 5,282,862 A | 2/1994 | Baker et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,211 A | 2/1995 | Saadatmanesh et al. |
| 5,387,212 A | 2/1995 | Yuan et al. |
| 5,395,371 A | 3/1995 | Miller et al. |
| 5,409,488 A | 4/1995 | Ulrich |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,434,001 A | 7/1995 | Yamada et al. |
| 5,443,467 A | 8/1995 | Biedermann et al. |
| 5,466,237 A | 11/1995 | Byrd, III et al. |
| 5,466,238 A | 11/1995 | Lin |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer et al. |
| 5,505,731 A | 4/1996 | Tornier |
| 5,507,745 A | 4/1996 | Logroscino et al. |
| 5,507,747 A | 4/1996 | Yuan et al. |
| 5,534,001 A | 7/1996 | Schlapfer et al. |
| 5,540,688 A | 7/1996 | Navas |
| 5,545,165 A | 8/1996 | Biedermann et al. |
| 5,549,607 A | 8/1996 | Olson et al. |
| 5,549,608 A | 8/1996 | Errico et al. |
| 5,554,157 A | 9/1996 | Errico et al. |
| 5,562,660 A | 10/1996 | Grob |

(56) References Cited

U.S. PATENT DOCUMENTS

| | | |
|---|---|---|
| 5,562,663 A | 10/1996 | Wisnewski et al. |
| 5,569,247 A | 10/1996 | Morrison |
| 5,569,251 A | 10/1996 | Baker et al. |
| 5,578,033 A | 11/1996 | Errico et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,609,593 A | 3/1997 | Errico et al. |
| 5,609,594 A | 3/1997 | Errico et al. |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann |
| 5,676,665 A | 10/1997 | Bryan |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,690,630 A | 11/1997 | Errico et al. |
| 5,702,393 A | 12/1997 | Pfaifer |
| 5,711,709 A | 1/1998 | McCoy |
| 5,713,705 A | 2/1998 | Grunbichler |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,351 A | 3/1999 | Viart |
| 5,882,350 A | 3/1999 | Ralph et al. |
| 5,902,303 A | 5/1999 | Eckhof et al. |
| RE36,221 E | 6/1999 | Breard et al. |
| 5,910,141 A | 6/1999 | Morrison et al. |
| 5,910,142 A | 6/1999 | Tatar |
| 5,928,236 A | 7/1999 | Augagneur et al. |
| 5,938,663 A | 8/1999 | Petreto |
| 5,941,880 A | 8/1999 | Errico et al. |
| 5,944,465 A | 8/1999 | Janitzki |
| 5,951,553 A | 9/1999 | Betz et al. |
| 5,961,517 A | 10/1999 | Biedermann et al. |
| 5,964,760 A | 10/1999 | Richelsoph |
| 5,964,767 A | 10/1999 | Tapia et al. |
| 5,997,539 A | 12/1999 | Errico et al. |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,056,753 A | 5/2000 | Jackson |
| 6,063,088 A | 5/2000 | Winslow |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,117,137 A | 9/2000 | Halm et al. |
| 6,129,763 A | 10/2000 | Chauvin et al. |
| 6,132,431 A | 10/2000 | Nilsson et al. |
| 6,136,002 A | 10/2000 | Shih et al. |
| 6,136,003 A | 10/2000 | Hoeck et al. |
| 6,143,032 A | 11/2000 | Schafer et al. |
| 6,146,383 A | 11/2000 | Studer et al. |
| 6,149,533 A | 11/2000 | Finn |
| 6,162,223 A | 12/2000 | Orsak et al. |
| 6,168,597 B1 | 1/2001 | Biedermann et al. |
| 6,183,472 B1 | 2/2001 | Lutz |
| 6,186,718 B1 | 2/2001 | Fogard |
| 6,193,719 B1 | 2/2001 | Gournay et al. |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,028 B1 | 5/2001 | Brumfield et al. |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,280,445 B1 | 8/2001 | Morrison et al. |
| 6,287,308 B1 | 9/2001 | Betz et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| RE37,665 E | 4/2002 | Ralph et al. |
| 6,368,321 B1 | 4/2002 | Jackson |
| 6,379,356 B1 | 4/2002 | Jackson |
| 6,402,757 B1 | 6/2002 | Moore et al. |
| 6,440,133 B1 | 8/2002 | Beale et al. |
| 6,443,956 B1 | 9/2002 | Ray |
| 6,467,958 B1 | 10/2002 | Sasaki et al. |
| 6,471,703 B1 | 10/2002 | Ashman |
| 6,478,797 B1 | 11/2002 | Paul |
| 6,478,798 B1 | 11/2002 | Howland |
| 6,485,491 B1 | 11/2002 | Farris et al. |
| 6,485,492 B1 | 11/2002 | Halm et al. |
| 6,485,494 B1 | 11/2002 | Haider |
| 6,520,962 B1 | 2/2003 | Taylor et al. |
| 6,527,804 B1 | 3/2003 | Gauchet et al. |
| 6,533,786 B1 | 3/2003 | Needham et al. |
| 6,554,831 B1 | 4/2003 | Rivard et al. |
| 6,554,834 B1 | 4/2003 | Crozet et al. |
| 6,562,040 B1 | 5/2003 | Wagner |
| 6,565,565 B1 | 5/2003 | Yuan et al. |
| 6,565,567 B1 | 5/2003 | Haider |
| 6,595,992 B1 | 7/2003 | Wagner et al. |
| 6,602,255 B1 | 8/2003 | Campbell et al. |
| 6,613,050 B1 | 9/2003 | Wagner et al. |
| 6,616,667 B1 | 9/2003 | Steiger et al. |
| 6,648,885 B1 | 11/2003 | Friesem |

(56) References Cited

U.S. PATENT DOCUMENTS

| | | |
|---|---|---|
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,663,632 B1 | 12/2003 | Frigg |
| 6,673,073 B1 | 1/2004 | Schafer |
| 6,676,661 B1 | 1/2004 | Benlloch et al. |
| 6,712,818 B1 | 3/2004 | Michelson |
| 6,716,214 B1 | 4/2004 | Jackson |
| 6,743,231 B1 | 6/2004 | Gray et al. |
| 6,755,829 B1 | 6/2004 | Bono et al. |
| 6,778,861 B1 | 8/2004 | Liebrecht et al. |
| 6,872,208 B1 | 3/2005 | McBride et al. |
| 6,896,677 B1 | 5/2005 | Lin |
| 7,001,389 B1 | 2/2006 | Navarro et al. |
| RE39,035 E | 3/2006 | Finn et al. |
| RE39,089 E | 5/2006 | Ralph et al. |
| 7,081,116 B1 | 7/2006 | Carly |
| 7,316,684 B1 | 1/2008 | Baccelli et al. |
| 7,686,833 B1 | 3/2010 | Muhanna et al. |
| 7,766,943 B1 | 8/2010 | Fallin et al. |
| 7,833,251 B1 | 11/2010 | Ahlgren et al. |
| 8,043,340 B1 | 10/2011 | Law |
| 8,092,499 B1 | 1/2012 | Roth |
| 8,167,914 B1 | 5/2012 | Hunt et al. |
| 8,197,517 B1 | 6/2012 | Lab et al. |
| 8,211,110 B1 | 7/2012 | Corin et al. |
| 8,236,035 B1 | 8/2012 | Bedor |
| 8,388,659 B1 | 3/2013 | Lab et al. |
| 8,439,924 B1 | 5/2013 | McBride et al. |
| 8,470,009 B1 | 6/2013 | Rezach |
| 2001/0007941 A1 | 7/2001 | Steiner et al. |
| 2001/0010000 A1 | 7/2001 | Gertzbein et al. |
| 2001/0011172 A1 | 8/2001 | Orbay et al. |
| 2001/0012937 A1 | 8/2001 | Schaffler-Wachter et al. |
| 2001/0023350 A1 | 9/2001 | Choi |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2001/0052438 A1 | 12/2001 | Spencer |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0049446 A1 | 4/2002 | Harkey, III et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0068975 A1 | 6/2002 | Teitelbaum et al. |
| 2002/0072750 A1 | 6/2002 | Jackson |
| 2002/0072751 A1 | 6/2002 | Jackson |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0095153 A1 | 7/2002 | Jones et al. |
| 2002/0095154 A1 | 7/2002 | Atkinson et al. |
| 2002/0095881 A1 | 7/2002 | Shreiner |
| 2002/0103487 A1 | 8/2002 | Errico et al. |
| 2002/0111627 A1 | 8/2002 | Vincent-Prestigiacomo |
| 2002/0116001 A1 | 8/2002 | Schaefer et al. |
| 2002/0120270 A1 | 8/2002 | Trieu et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143328 A1 | 10/2002 | Shluzas et al. |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0173791 A1 | 11/2002 | Howland |
| 2002/0183747 A1 | 12/2002 | Jao et al. |
| 2002/0198526 A1 | 12/2002 | Shaolian et al. |
| 2003/0004519 A1 | 1/2003 | Torode et al. |
| 2003/0023243 A1 | 1/2003 | Biedermann et al. |
| 2003/0028191 A1 | 2/2003 | Shluzas |
| 2003/0032957 A1 | 2/2003 | McKinley |
| 2003/0055426 A1 | 3/2003 | Carbone et al. |
| 2003/0055427 A1 | 3/2003 | Graf |
| 2003/0060826 A1 | 3/2003 | Foley et al. |
| 2003/0073995 A1 | 4/2003 | Reed |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0139745 A1 | 7/2003 | Ashman |
| 2003/0149431 A1 | 8/2003 | Varieur |
| 2003/0149432 A1 | 8/2003 | Frigg et al. |
| 2003/0149435 A1 | 8/2003 | Baynham et al. |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176863 A1 | 9/2003 | Ueyama et al. |
| 2003/0181913 A1 | 9/2003 | Lieberman |
| 2003/0187433 A1 | 10/2003 | Lin |
| 2003/0187434 A1 | 10/2003 | Lin |
| 2003/0191470 A1 | 10/2003 | Ritland |
| 2003/0199872 A1 | 10/2003 | Markworth et al. |
| 2003/0199873 A1 | 10/2003 | Richelsoph |
| 2003/0208204 A1 | 11/2003 | Bailey et al. |
| 2003/0212398 A1 | 11/2003 | Jackson |
| 2003/0216735 A1 | 11/2003 | Altarac et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0006342 A1 | 1/2004 | Altarac et al. |
| 2004/0039384 A1 | 2/2004 | Boehm, Jr. et al. |
| 2004/0039385 A1 | 2/2004 | Mazda et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |

(56) References Cited

U.S. PATENT DOCUMENTS

| | | |
|---|---|---|
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0122442 A1 | 6/2004 | Lewis |
| 2004/0127904 A1 | 7/2004 | Konieczynski et al. |
| 2004/0133207 A1 | 7/2004 | Abdou |
| 2004/0138660 A1 | 7/2004 | Serhan |
| 2004/0138662 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar, Jr. et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167523 A1 | 8/2004 | Jackson |
| 2004/0167525 A1 | 8/2004 | Jackson |
| 2004/0172025 A1 | 9/2004 | Drewry et al. |
| 2004/0172031 A1 | 9/2004 | Rubecamp et al. |
| 2004/0172032 A1 | 9/2004 | Jackson |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0210216 A1 | 10/2004 | Farris et al. |
| 2004/0210227 A1 | 10/2004 | Trail et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236330 A1 | 11/2004 | Purcell et al. |
| 2004/0249378 A1 | 12/2004 | Saint Martin et al. |
| 2004/0254574 A1 | 12/2004 | Morrison et al. |
| 2004/0260283 A1 | 12/2004 | Wu et al. |
| 2004/0267264 A1 | 12/2004 | Konieczynski et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0090821 A1 | 4/2005 | Berrevoets et al. |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |
| 2005/0131422 A1 | 6/2005 | Anderson |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149053 A1 | 7/2005 | Varieur |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177154 A1 | 8/2005 | Moumene et al. |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192572 A1 | 9/2005 | Abdelgany et al. |
| 2005/0192573 A1 | 9/2005 | Abdelgany et al. |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228379 A1 | 10/2005 | Jackson |
| 2005/0228385 A1 | 10/2005 | Lee et al. |
| 2005/0228400 A1 | 10/2005 | Chao |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |

(56) References Cited

U.S. PATENT DOCUMENTS

| | | |
|---|---|---|
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288672 A1 | 12/2005 | Ferree |
| 2005/0288673 A1 | 12/2005 | Catbagan et al. |
| 2006/0004359 A1 | 1/2006 | Kramer et al. |
| 2006/0004363 A1 | 1/2006 | Brockmeyer et al. |
| 2006/0009767 A1 | 1/2006 | Kiester |
| 2006/0009769 A1 | 1/2006 | Lieberman |
| 2006/0009770 A1 | 1/2006 | Speirs et al. |
| 2006/0009780 A1 | 1/2006 | Foley et al. |
| 2006/0015099 A1 | 1/2006 | Cannon et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036243 A1 | 2/2006 | Sasso et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074418 A1 | 4/2006 | Jackson |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106381 A1 | 5/2006 | Ferree et al. |
| 2006/0106394 A1 | 5/2006 | Colleran |
| 2006/0111713 A1 | 5/2006 | Jackson |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0149228 A1 | 7/2006 | Schlapfer et al. |
| 2006/0149229 A1 | 7/2006 | Kwak et al. |
| 2006/0149238 A1 | 7/2006 | Sherman et al. |
| 2006/0149240 A1 | 7/2006 | Jackson |
| 2006/0149241 A1 | 7/2006 | Richelsoph et al. |
| 2006/0149251 A1 | 7/2006 | Ziolo et al. |
| 2006/0155277 A1 | 7/2006 | Metz-Stavenhagen |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173456 A1 | 8/2006 | Hawkes et al. |
| 2006/0184171 A1 | 8/2006 | Biedermann |
| 2006/0184180 A1 | 8/2006 | Augostino et al. |
| 2006/0189983 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200133 A1 | 9/2006 | Jackson |
| 2006/0200149 A1 | 9/2006 | Hoy et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217716 A1 | 9/2006 | Baker et al. |
| 2006/0217719 A1 | 9/2006 | Albert et al. |
| 2006/0229608 A1 | 10/2006 | Foster et al. |
| 2006/0229609 A1 | 10/2006 | Wang |
| 2006/0229613 A1 | 10/2006 | Timm et al. |
| 2006/0229614 A1 | 10/2006 | Foley et al. |
| 2006/0229615 A1 | 10/2006 | Abdou |
| 2006/0241593 A1 | 10/2006 | Sherman et al. |
| 2006/0241595 A1 | 10/2006 | Molz, IV et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247658 A1 | 11/2006 | Pond, Jr. et al. |
| 2006/0260483 A1 | 11/2006 | Hartmann et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264962 A1 | 11/2006 | Chin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016190 A1 | 1/2007 | Martinez et al. |
| 2007/0016194 A1 | 1/2007 | Shaolian et al. |

(56) References Cited

U.S. PATENT DOCUMENTS

| | | |
|---|---|---|
| 2007/0016200 A1 | 1/2007 | Jackson |
| 2007/0021750 A1 | 1/2007 | Shluzas et al. |
| 2007/0032123 A1 | 2/2007 | Timm et al. |
| 2007/0043356 A1 | 2/2007 | Timm et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055236 A1 | 3/2007 | Hudgins et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073289 A1 | 3/2007 | Kwak et al. |
| 2007/0073290 A1 | 3/2007 | Boehm, Jr. |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan et al. |
| 2007/0093814 A1 | 4/2007 | Callahan, II et al. |
| 2007/0093815 A1 | 4/2007 | Callahan, II et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123867 A1 | 5/2007 | Kirschman |
| 2007/0123870 A1 | 5/2007 | Jeon et al. |
| 2007/0156142 A1 | 7/2007 | Rezach et al. |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191832 A1 | 8/2007 | Trieu |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233073 A1 | 10/2007 | Wisnewski et al. |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233089 A1 | 10/2007 | Dipoto et al. |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0244482 A1 | 10/2007 | Aferzon |
| 2007/0250061 A1 | 10/2007 | Chin et al. |
| 2007/0260243 A1 | 11/2007 | Kagami |
| 2007/0270813 A1 | 11/2007 | Garamszegi |
| 2007/0270821 A1 | 11/2007 | Trieu et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270843 A1 | 11/2007 | Matthis et al. |
| 2007/0270869 A1 | 11/2007 | Young et al. |
| 2007/0276371 A1 | 11/2007 | Baynham et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288012 A1 | 12/2007 | Colleran et al. |
| 2007/0293862 A1 | 12/2007 | Jackson |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0027432 A1 | 1/2008 | Strauss et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091213 A1 | 4/2008 | Jackson |
| 2008/0097441 A1 | 4/2008 | Hayes et al. |
| 2008/0103502 A1 | 5/2008 | Capote et al. |
| 2008/0108992 A1 | 5/2008 | Barry et al. |
| 2008/0114362 A1 | 5/2008 | Justis et al. |
| 2008/0114403 A1 | 5/2008 | Kuester et al. |
| 2008/0119849 A1 | 5/2008 | Beardsley et al. |
| 2008/0119857 A1 | 5/2008 | Potash et al. |
| 2008/0125777 A1 | 5/2008 | Veldman et al. |
| 2008/0125787 A1 | 5/2008 | Doubler et al. |
| 2008/0125813 A1 | 5/2008 | Erickson et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0140136 A1 | 6/2008 | Jackson |
| 2008/0147121 A1 | 6/2008 | Justis et al. |
| 2008/0147122 A1 | 6/2008 | Jackson |
| 2008/0147129 A1 | 6/2008 | Biedermann et al. |
| 2008/0147195 A1 | 6/2008 | Kwak et al. |
| 2008/0154279 A1 | 6/2008 | Schumacher et al. |
| 2008/0154308 A1 | 6/2008 | Sherman et al. |
| 2008/0154315 A1 | 6/2008 | Jackson |
| 2008/0161857 A1 | 7/2008 | Hestad et al. |

(56) References Cited

U.S. PATENT DOCUMENTS

| | | |
|---|---|---|
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177321 A1 | 7/2008 | Drewry et al. |
| 2008/0177322 A1 | 7/2008 | Davis et al. |
| 2008/0177323 A1 | 7/2008 | Null et al. |
| 2008/0177388 A1 | 7/2008 | Patterson et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0188898 A1 | 8/2008 | Jackson |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0215100 A1 | 9/2008 | Matthis et al. |
| 2008/0228184 A1 | 9/2008 | Hestad |
| 2008/0228228 A1 | 9/2008 | Hestad et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0243052 A1 | 10/2008 | Pond et al. |
| 2008/0243185 A1 | 10/2008 | Felix et al. |
| 2008/0243193 A1 | 10/2008 | Ensign et al. |
| 2008/0249570 A1 | 10/2008 | Carson et al. |
| 2008/0262548 A1 | 10/2008 | Lange et al. |
| 2008/0262551 A1 | 10/2008 | Rice et al. |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0294203 A1 | 11/2008 | Kovach et al. |
| 2008/0300630 A1 | 12/2008 | Bonnema et al. |
| 2008/0300631 A1 | 12/2008 | Tornier |
| 2008/0300633 A1 | 12/2008 | Jackson |
| 2008/0306513 A1 | 12/2008 | Winslow et al. |
| 2008/0306525 A1 | 12/2008 | Winslow et al. |
| 2008/0306526 A1 | 12/2008 | Winslow et al. |
| 2008/0306533 A1 | 12/2008 | Winslow et al. |
| 2008/0306536 A1 | 12/2008 | Frigg et al. |
| 2008/0306540 A1 | 12/2008 | Mitchell et al. |
| 2008/0306543 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2008/0319482 A1 | 12/2008 | Jackson |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018557 A1 | 1/2009 | Pisharodi |
| 2009/0018583 A1 | 1/2009 | Song et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0062860 A1 | 3/2009 | Frasier et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082666 A1 | 3/2009 | Geist et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088769 A1 | 4/2009 | Poletti |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093846 A1 | 4/2009 | Hestad et al. |
| 2009/0099606 A1 | 4/2009 | Hestad et al. |
| 2009/0099608 A1 | 4/2009 | Szczesny |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0105820 A1 | 4/2009 | Jackson |
| 2009/0112265 A1 | 4/2009 | Hudgins et al. |
| 2009/0112266 A1 | 4/2009 | Weng et al. |
| 2009/0112269 A1 | 4/2009 | Lieberman et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0149885 A1 | 6/2009 | Durward et al. |
| 2009/0149892 A1 | 6/2009 | Stad et al. |
| 2009/0157120 A1 | 6/2009 | Marino et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0177237 A1 | 7/2009 | Zucherman et al. |
| 2009/0182380 A1 | 7/2009 | Abdelgany |
| 2009/0182430 A1 | 7/2009 | Tyber et al. |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0216278 A1 | 8/2009 | Song |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248083 A1 | 10/2009 | Patterson et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0259257 A1 | 10/2009 | Prevost |

(56) References Cited

U.S. PATENT DOCUMENTS

| | | |
|---|---|---|
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275985 A1 | 11/2009 | Jackson |
| 2009/0275986 A1 | 11/2009 | Prevost et al. |
| 2009/0281542 A1 | 11/2009 | Justis |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0281574 A1 | 11/2009 | Jackson |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2010/0004692 A1 | 1/2010 | Biedermann et al. |
| 2010/0004694 A1 | 1/2010 | Little |
| 2010/0004695 A1 | 1/2010 | Stad et al. |
| 2010/0010540 A1 | 1/2010 | Park |
| 2010/0010542 A1 | 1/2010 | Jackson |
| 2010/0010543 A1 | 1/2010 | Jackson |
| 2010/0023061 A1 | 1/2010 | Randol et al. |
| 2010/0030224 A1 | 2/2010 | Winslow et al. |
| 2010/0030272 A1 | 2/2010 | Winslow et al. |
| 2010/0030283 A1 | 2/2010 | King et al. |
| 2010/0036417 A1 | 2/2010 | James et al. |
| 2010/0036422 A1 | 2/2010 | Flynn et al. |
| 2010/0036423 A1 | 2/2010 | Hayes et al. |
| 2010/0036425 A1 | 2/2010 | Barrus et al. |
| 2010/0036432 A1 | 2/2010 | Ely |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0057125 A1 | 3/2010 | Viker |
| 2010/0057126 A1 | 3/2010 | Hestad |
| 2010/0057131 A1 | 3/2010 | Ely |
| 2010/0063544 A1 | 3/2010 | Butler |
| 2010/0063545 A1 | 3/2010 | Richelsoph |
| 2010/0063546 A1 | 3/2010 | Miller et al. |
| 2010/0063547 A1 | 3/2010 | Morin et al. |
| 2010/0063550 A1 | 3/2010 | Felix et al. |
| 2010/0063552 A1 | 3/2010 | Chin et al. |
| 2010/0069919 A1 | 3/2010 | Carls et al. |
| 2010/0069969 A1 | 3/2010 | Ampuero et al. |
| 2010/0082066 A1 | 4/2010 | Biyani |
| 2010/0087858 A1 | 4/2010 | Abdou |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0094343 A1 | 4/2010 | Pham et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0106192 A1 | 4/2010 | Barry |
| 2010/0114165 A1 | 5/2010 | Ely |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121386 A1 | 5/2010 | Peultier et al. |
| 2010/0125302 A1 | 5/2010 | Hammill, Sr. et al. |
| 2010/0137908 A1 | 6/2010 | Zhang |
| 2010/0137912 A1 | 6/2010 | Alcock et al. |
| 2010/0137918 A1 | 6/2010 | Wilcox et al. |
| 2010/0137920 A1 | 6/2010 | Hammill, Sr. et al. |
| 2010/0152776 A1 | 6/2010 | Keyer et al. |
| 2010/0152785 A1 | 6/2010 | Forton et al. |
| 2010/0160965 A1 | 6/2010 | Viker |
| 2010/0160967 A1 | 6/2010 | Capozzoli |
| 2010/0160968 A1 | 6/2010 | Joshi et al. |
| 2010/0160974 A1 | 6/2010 | Viker |
| 2010/0160976 A1 | 6/2010 | Biedermann et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0191293 A1 | 7/2010 | Jackson |
| 2010/0204735 A1 | 8/2010 | Gephart et al. |
| 2010/0211104 A1 | 8/2010 | Moumene et al. |
| 2010/0211105 A1 | 8/2010 | Moumene et al. |
| 2010/0211114 A1 | 8/2010 | Jackson |
| 2010/0222822 A1 | 9/2010 | Farris et al. |
| 2010/0222828 A1 | 9/2010 | Stad et al. |
| 2010/0234902 A1 | 9/2010 | Biedermann et al. |
| 2010/0249843 A1 | 9/2010 | Wegrzyn, III |
| 2010/0249846 A1 | 9/2010 | Simonson |
| 2010/0249856 A1 | 9/2010 | Iott et al. |
| 2010/0262185 A1 | 10/2010 | Gelfand et al. |
| 2010/0262187 A1 | 10/2010 | Marik et al. |
| 2010/0262190 A1 | 10/2010 | Ballard et al. |
| 2010/0262191 A1 | 10/2010 | Marik et al. |
| 2010/0262192 A1 | 10/2010 | Foley |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2010/0298891 A1 | 11/2010 | Jackson |
| 2010/0305621 A1 | 12/2010 | Wang et al. |
| 2010/0312288 A1 | 12/2010 | Hammill, Sr. et al. |
| 2010/0331885 A1 | 12/2010 | Remington et al. |
| 2011/0004256 A1 | 1/2011 | Biedermann et al. |
| 2011/0009906 A1 | 1/2011 | Hestad et al. |
| 2011/0009911 A1 | 1/2011 | Hammill et al. |
| 2011/0029022 A1 | 2/2011 | Zehnder et al. |
| 2011/0040338 A1 | 2/2011 | Jackson |
| 2011/0046683 A1 | 2/2011 | Biedermann et al. |
| 2011/0093015 A1 | 4/2011 | Ramsay et al. |
| 2011/0093021 A1 | 4/2011 | Fanger et al. |
| 2011/0106174 A1 | 5/2011 | Rezach |
| 2011/0106175 A1 | 5/2011 | Rezach |
| 2011/0130792 A1 | 6/2011 | Nydegger et al. |
| 2011/0152939 A1 | 6/2011 | Aldridge |
| 2011/0152949 A1 | 6/2011 | Biedermann et al. |
| 2011/0160778 A1 | 6/2011 | Elsbury |
| 2011/0166610 A1 | 7/2011 | Altarac et al. |
| 2011/0178558 A1 | 7/2011 | Barry |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0190822 A1 | 8/2011 | Spitler et al. |
| 2011/0196430 A1 | 8/2011 | Walsh et al. |
| 2011/0202094 A1 | 8/2011 | Pereira et al. |
| 2011/0202095 A1 | 8/2011 | Semler et al. |
| 2011/0230915 A1 | 9/2011 | Anderson et al. |
| 2011/0238119 A1 | 9/2011 | Moumene et al. |
| 2011/0251644 A1 | 10/2011 | Hestad et al. |
| 2011/0257685 A1 | 10/2011 | Hay et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2011/0263945 A1 | 10/2011 | Peterson et al. |

(56) References Cited

U.S. PATENT DOCUMENTS

| | | |
|---|---|---|
| 2011/0313460 A1 | 12/2011 | Mclean et al. |
| 2011/0313463 A1 | 12/2011 | McLean |
| 2011/0313471 A1 | 12/2011 | McLean et al. |
| 2012/0029568 A1 | 2/2012 | Jackson |
| 2012/0046699 A1 | 2/2012 | Jones et al. |
| 2012/0053636 A1 | 3/2012 | Schmocker |
| 2012/0078307 A1 | 3/2012 | Nihalani |
| 2012/0197314 A1 | 8/2012 | Farris |
| 2012/0232598 A1 | 9/2012 | Hestad et al. |
| 2012/0310284 A1 | 12/2012 | Gerchow |
| 2013/0103097 A1 | 4/2013 | May et al. |

FOREIGN PATENT DOCUMENTS

| | | |
|---|---|---|
| DE | 3630863 | 3/1988 |
| DE | G9202745.8 | 4/1992 |
| DE | 4425392 | 11/1995 |
| DE | 29806563 | 6/1998 |
| DE | 29810798 | 12/1999 |
| DE | 19951145 | 5/2001 |
| DE | 102007055745 | 7/2008 |
| EP | 0172130 | 2/1987 |
| EP | 0276153 | 7/1988 |
| EP | 0667127 | 8/1995 |
| EP | 0669109 | 8/1995 |
| EP | 0677277 | 10/1995 |
| EP | 1277444 | 1/2003 |
| EP | 2082709 | 7/2009 |
| EP | 2468198 | 12/2010 |
| ES | 2384773 | 7/2012 |
| FR | 2467312 | 4/1981 |
| FR | 2715825 | 8/1995 |
| FR | 2717370 | 9/1995 |
| FR | 2718946 | 10/1995 |
| FR | 2799949 | 4/2001 |
| FR | 2814936 | 4/2002 |
| FR | 2815535 | 4/2002 |
| FR | 2856578 | 6/2003 |
| FR | 2865377 | 1/2004 |
| FR | 2846223 | 4/2004 |
| FR | 2857850 | 4/2004 |
| FR | 2925288 | 6/2009 |
| GB | 203508 | 9/1923 |
| GB | 2082709 | 3/1982 |
| GB | 0195455 | 11/1984 |
| GB | 2140523 | 11/1984 |
| GB | 2365345 | 2/2002 |
| GB | 2382304 | 5/2003 |
| JP | S4867159 | 9/1973 |
| JP | S50106061 | 8/1975 |
| JP | H10277070 | 10/1998 |
| JP | 2000325358 | 3/2000 |
| JP | 0252030 | 2/2002 |
| JP | 2002221218 | 8/2002 |
| SU | 371359 | 2/1973 |
| WO | 8909030 | 10/1989 |
| WO | 8912431 | 12/1989 |
| WO | 9116018 | 10/1991 |
| WO | 9116020 | 10/1991 |
| WO | 9203100 | 3/1992 |
| WO | 9321848 | 11/1993 |
| WO | 9325161 | 12/1993 |
| WO | 9410927 | 5/1994 |
| WO | 9410944 | 5/1994 |
| WO | 9426191 | 11/1994 |
| WO | 9428824 | 12/1994 |
| WO | 9501132 | 1/1995 |
| WO | 9513755 | 5/1995 |
| WO | 9528889 | 11/1995 |
| WO | 9531947 | 11/1995 |
| WO | 9535067 | 12/1995 |
| WO | 9606576 | 3/1996 |
| WO | 9621396 | 7/1996 |
| WO | 9625104 | 8/1996 |
| WO | 9628105 | 9/1996 |
| WO | 9628118 | 9/1996 |
| WO | 9641582 | 12/1996 |
| WO | 9714366 | 4/1997 |
| WO | 9714368 | 4/1997 |
| WO | 9727812 | 8/1997 |
| WO | 9730649 | 8/1997 |
| WO | 9737604 | 10/1997 |
| WO | 9737605 | 10/1997 |
| WO | 9812977 | 4/1998 |
| WO | 9815233 | 4/1998 |
| WO | 9825534 | 6/1998 |
| WO | 9832386 | 7/1998 |
| WO | 9834554 | 8/1998 |
| WO | 9834556 | 8/1998 |
| WO | 9838924 | 9/1998 |
| WO | 9903415 | 1/1999 |
| WO | 9905980 | 2/1999 |
| WO | 9932084 | 7/1999 |
| WO | 9938463 | 8/1999 |
| WO | 9947083 | 9/1999 |
| WO | 9949802 | 10/1999 |
| WO | 0015125 | 3/2000 |
| WO | 0022997 | 4/2000 |
| WO | 0027297 | 5/2000 |
| WO | 0072769 | 7/2000 |
| WO | 0065268 | 11/2000 |
| WO | 0066045 | 11/2000 |
| WO | 0106940 | 2/2001 |
| WO | 0108574 | 2/2001 |
| WO | 0110317 | 2/2001 |
| WO | 0115612 | 3/2001 |
| WO | 0122893 | 4/2001 |
| WO | 0128435 | 4/2001 |
| WO | 0128436 | 4/2001 |
| WO | 0145576 | 6/2001 |
| WO | 0149191 | 7/2001 |
| WO | 0158370 | 8/2001 |
| WO | 0167972 | 9/2001 |
| WO | 0167974 | 9/2001 |
| WO | 0222030 | 3/2002 |
| WO | 0234150 | 5/2002 |
| WO | 02054966 | 7/2002 |
| WO | 02102259 | 12/2002 |
| WO | 03007828 | 1/2003 |
| WO | 03026523 | 4/2003 |
| WO | 03037199 | 5/2003 |
| WO | 03047442 | 6/2003 |
| WO | 03068083 | 8/2003 |
| WO | 03068088 | 8/2003 |
| WO | 03084415 | 10/2003 |
| WO | 03094699 | 11/2003 |
| WO | 2004021900 | 3/2004 |
| WO | 2004022108 | 3/2004 |
| WO | 2004041100 | 5/2004 |
| WO | 2004075778 | 9/2004 |
| WO | 2004089245 | 10/2004 |
| WO | 2004098452 | 11/2004 |
| WO | 2004105577 | 12/2004 |
| WO | 2004107997 | 12/2004 |
| WO | 2005000136 | 1/2005 |
| WO | 2005000137 | 1/2005 |
| WO | 2005013839 | 2/2005 |
| WO | 2005018466 | 3/2005 |
| WO | 2005018471 | 3/2005 |
| WO | 2005020829 | 3/2005 |
| WO | 2005030068 | 4/2005 |
| WO | 2005065374 | 7/2005 |
| WO | 2005072632 | 8/2005 |
| WO | 2005082262 | 9/2005 |
| WO | 2005087121 | 9/2005 |
| WO | 2005099400 | 10/2005 |
| WO | 2005102195 | 11/2005 |
| WO | 2005104969 | 11/2005 |
| WO | 2006005198 | 1/2006 |
| WO | 2006017616 | 2/2006 |
| WO | 2006020530 | 2/2006 |
| WO | 2006042188 | 4/2006 |
| WO | 2006047711 | 5/2006 |

(56) References Cited

FOREIGN PATENT DOCUMENTS

| | | |
|---|---|---|
| WO | 2006054111 | 5/2006 |
| WO | 2006065607 | 6/2006 |
| WO | 2006066685 | 6/2006 |
| WO | 2006068711 | 6/2006 |
| WO | 2006071742 | 7/2006 |
| WO | 2006079531 | 8/2006 |
| WO | 2006096240 | 9/2006 |
| WO | 2006096351 | 9/2006 |
| WO | 2006104874 | 10/2006 |
| WO | 2006110463 | 10/2006 |
| WO | 2006116437 | 11/2006 |
| WO | 2006119447 | 11/2006 |
| WO | 2007002409 | 1/2007 |
| WO | 2007038350 | 4/2007 |
| WO | 2007040750 | 4/2007 |
| WO | 2007040888 | 4/2007 |
| WO | 2007041702 | 4/2007 |
| WO | 2007053566 | 5/2007 |
| WO | 2007060534 | 5/2007 |
| WO | 2007075454 | 7/2007 |
| WO | 2007081849 | 8/2007 |
| WO | 2007087469 | 8/2007 |
| WO | 2007087628 | 8/2007 |
| WO | 2007090021 | 8/2007 |
| WO | 2007092056 | 8/2007 |
| WO | 2007092870 | 8/2007 |
| WO | 2007097905 | 8/2007 |
| WO | 2007109470 | 9/2007 |
| WO | 2007114834 | 10/2007 |
| WO | 2007118045 | 10/2007 |
| WO | 2007121030 | 10/2007 |
| WO | 2007121057 | 10/2007 |
| WO | 2007121271 | 10/2007 |
| WO | 2007123920 | 11/2007 |
| WO | 2007124222 | 11/2007 |
| WO | 2007124249 | 11/2007 |
| WO | 2007127595 | 11/2007 |
| WO | 2007127604 | 11/2007 |
| WO | 2007130835 | 11/2007 |
| WO | 2007130840 | 11/2007 |
| WO | 2007130941 | 11/2007 |
| WO | 2007138270 | 12/2007 |
| WO | 2007146032 | 12/2007 |
| WO | 2008005740 | 1/2008 |
| WO | 2008006098 | 1/2008 |
| WO | 2008008511 | 1/2008 |
| WO | 2008013892 | 1/2008 |
| WO | 2008027860 | 3/2008 |
| WO | 2008033742 | 3/2008 |
| WO | 2008036975 | 3/2008 |
| WO | 2008037256 | 4/2008 |
| WO | 2008039777 | 4/2008 |
| WO | 2008042948 | 4/2008 |
| WO | 2008048923 | 4/2008 |
| WO | 2008048953 | 4/2008 |
| WO | 2008051737 | 4/2008 |
| WO | 2008069420 | 6/2008 |
| WO | 2008070716 | 6/2008 |
| WO | 2008134703 | 6/2008 |
| WO | 2008078163 | 7/2008 |
| WO | 2008082737 | 7/2008 |
| WO | 2008100590 | 8/2008 |
| WO | 2008118295 | 10/2008 |
| WO | 2008119006 | 10/2008 |
| WO | 2008124772 | 10/2008 |
| WO | 2008140756 | 11/2008 |
| WO | 2008157589 | 12/2008 |
| WO | 2009003153 | 12/2008 |
| WO | 2009006225 | 1/2009 |
| WO | 2009011845 | 1/2009 |
| WO | 2009014540 | 1/2009 |
| WO | 2009015100 | 1/2009 |
| WO | 2009018086 | 2/2009 |
| WO | 2009029928 | 3/2009 |
| WO | 2009055028 | 4/2009 |
| WO | 2009055400 | 4/2009 |
| WO | 2009055407 | 4/2009 |
| WO | 2009152302 | 12/2009 |
| WO | 2009155360 | 12/2009 |
| WO | 2010017631 | 2/2010 |
| WO | 2010018316 | 2/2010 |
| WO | 2010018317 | 2/2010 |
| WO | 2010019857 | 2/2010 |
| WO | 2010030916 | 3/2010 |
| WO | 2010045383 | 4/2010 |
| WO | 2010065648 | 6/2010 |
| WO | 2010078901 | 7/2010 |
| WO | 2010111500 | 9/2010 |
| WO | 2010120989 | 10/2010 |
| WO | 2010147639 | 12/2010 |
| WO | 2011043805 | 4/2011 |
| WO | 2011068818 | 6/2011 |
| WO | 2012033532 | 3/2012 |
| WO | 2012075827 | 6/2012 |
| WO | 2012088890 | 7/2012 |

OTHER PUBLICATIONS

CD Horizon M8 Multi Axial Screw Spinal System Brochure, Medtronic Sofamor Danek, no publish date.
Claris Instrumentation Brochure, G Med, pub. 1997.
Contour Spinal System Brochure, Ortho Development, no publish date.
EBI Omega 21 Brochure, EBI Spine Systems, pub. 1999.
SDRS Surgical Dynamics Rod System Brochure, Surgical Dynamics, pub. 1998-1999.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.
Brochure of DePuySpine on Surgical Technique, Published 2004, pp. 1-36.

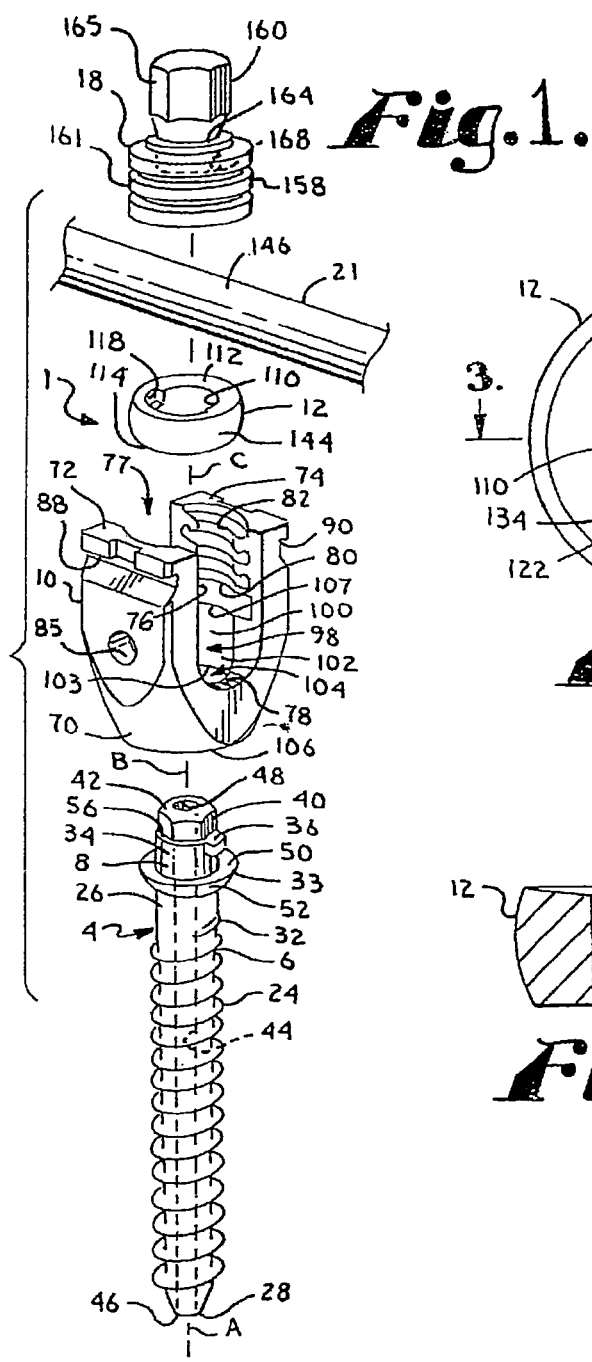
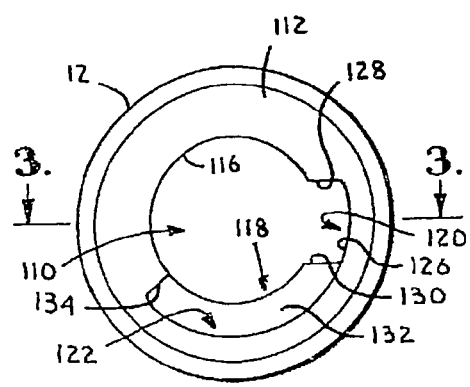
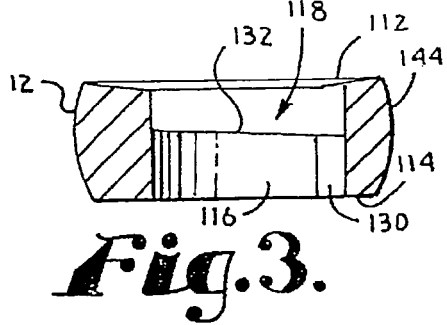

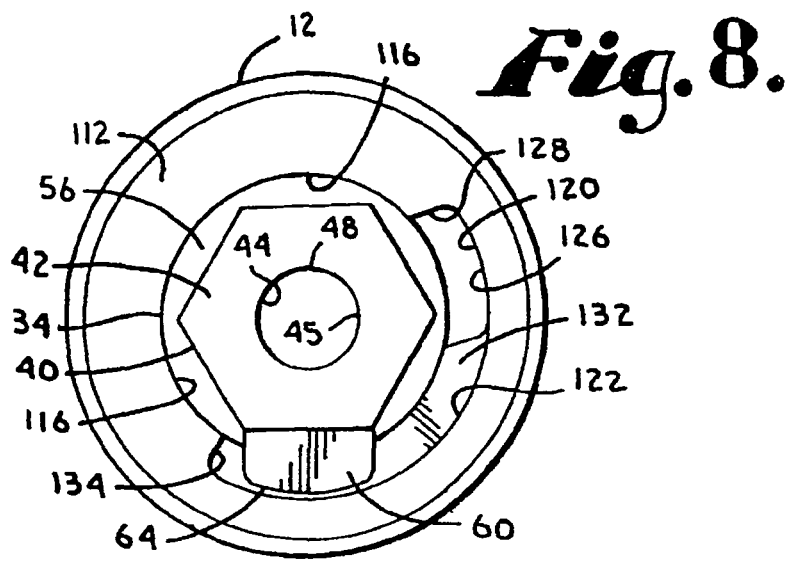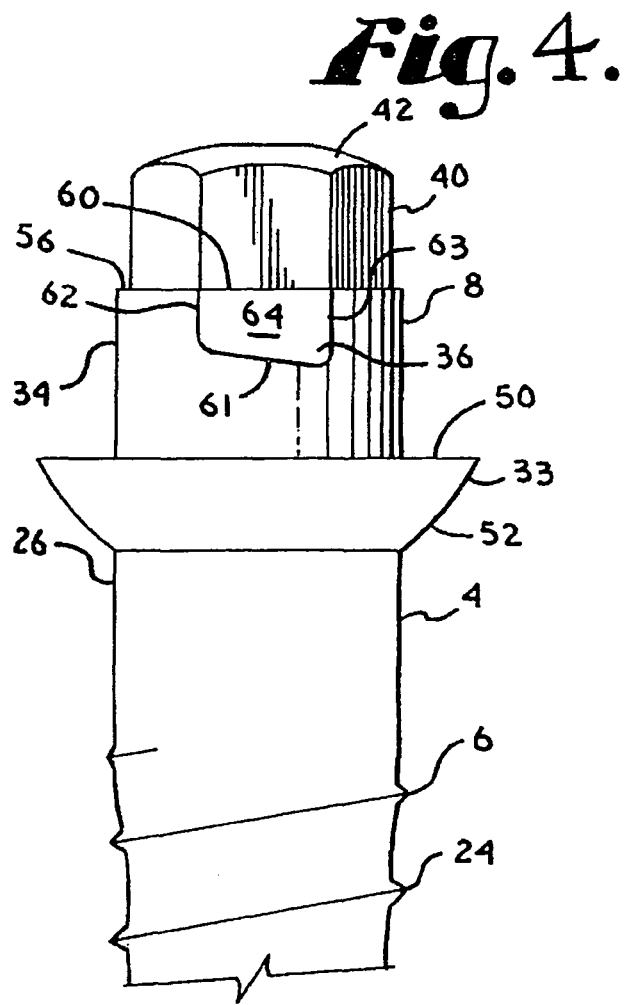

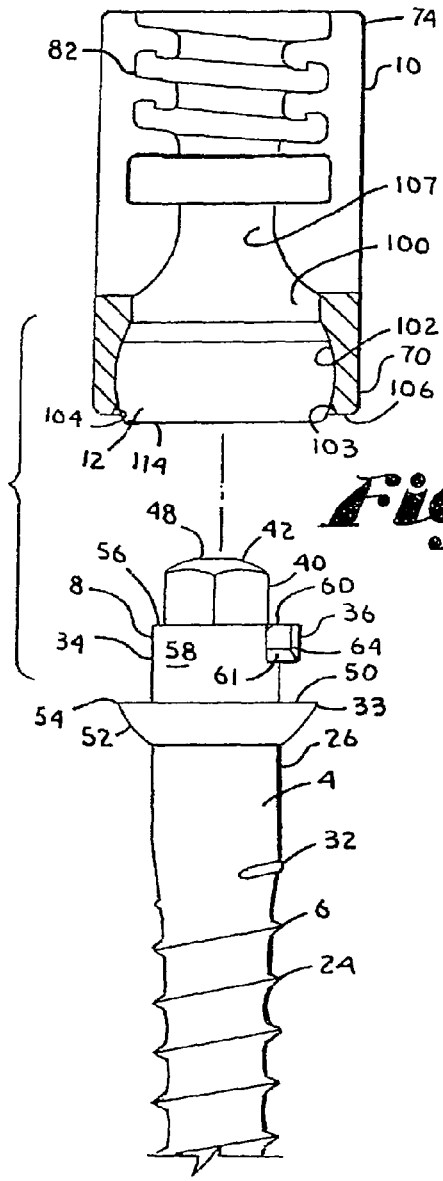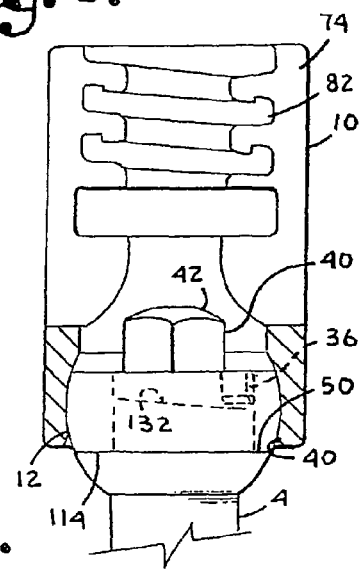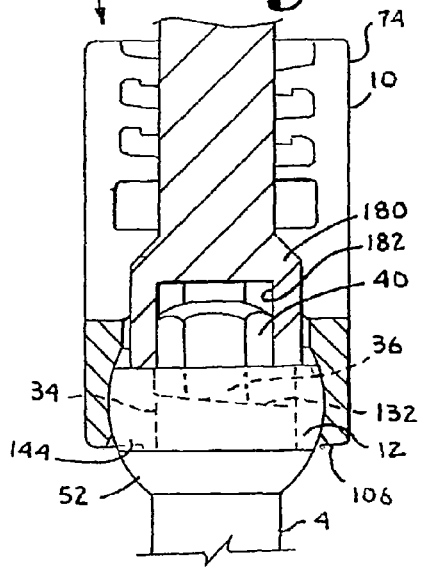

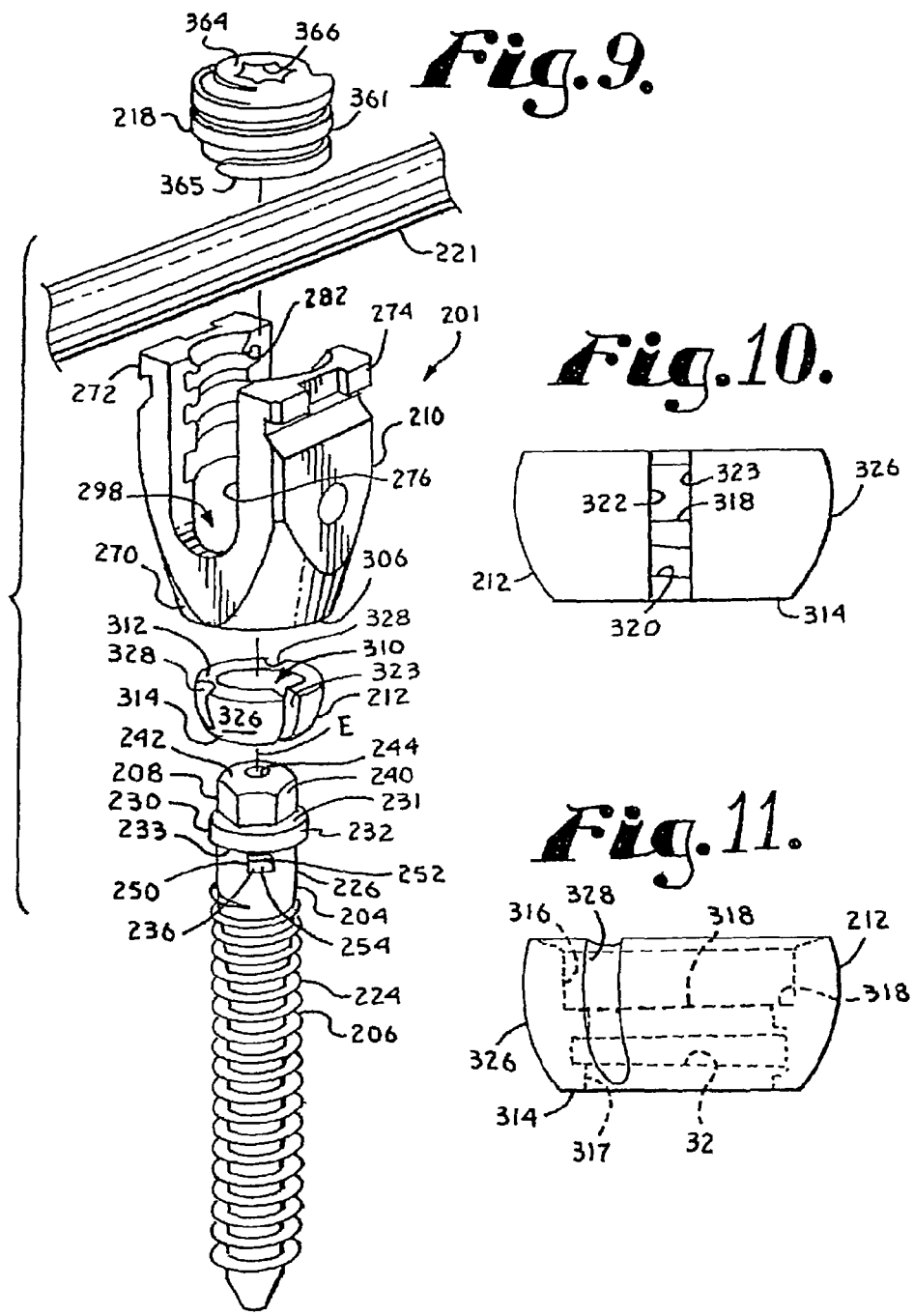

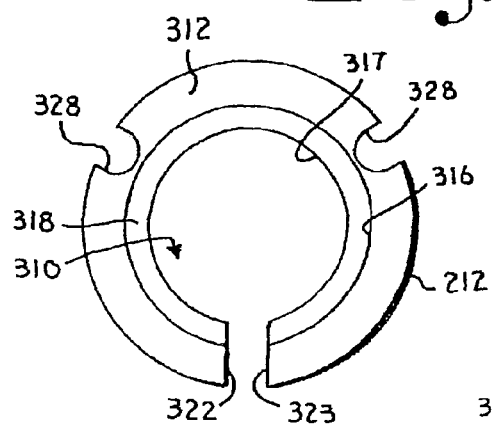
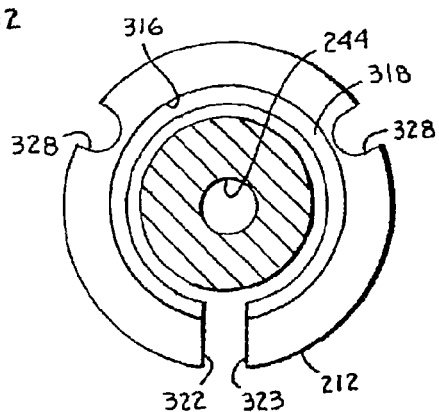
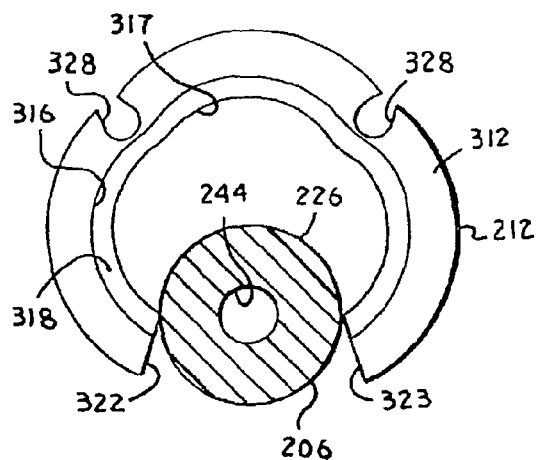

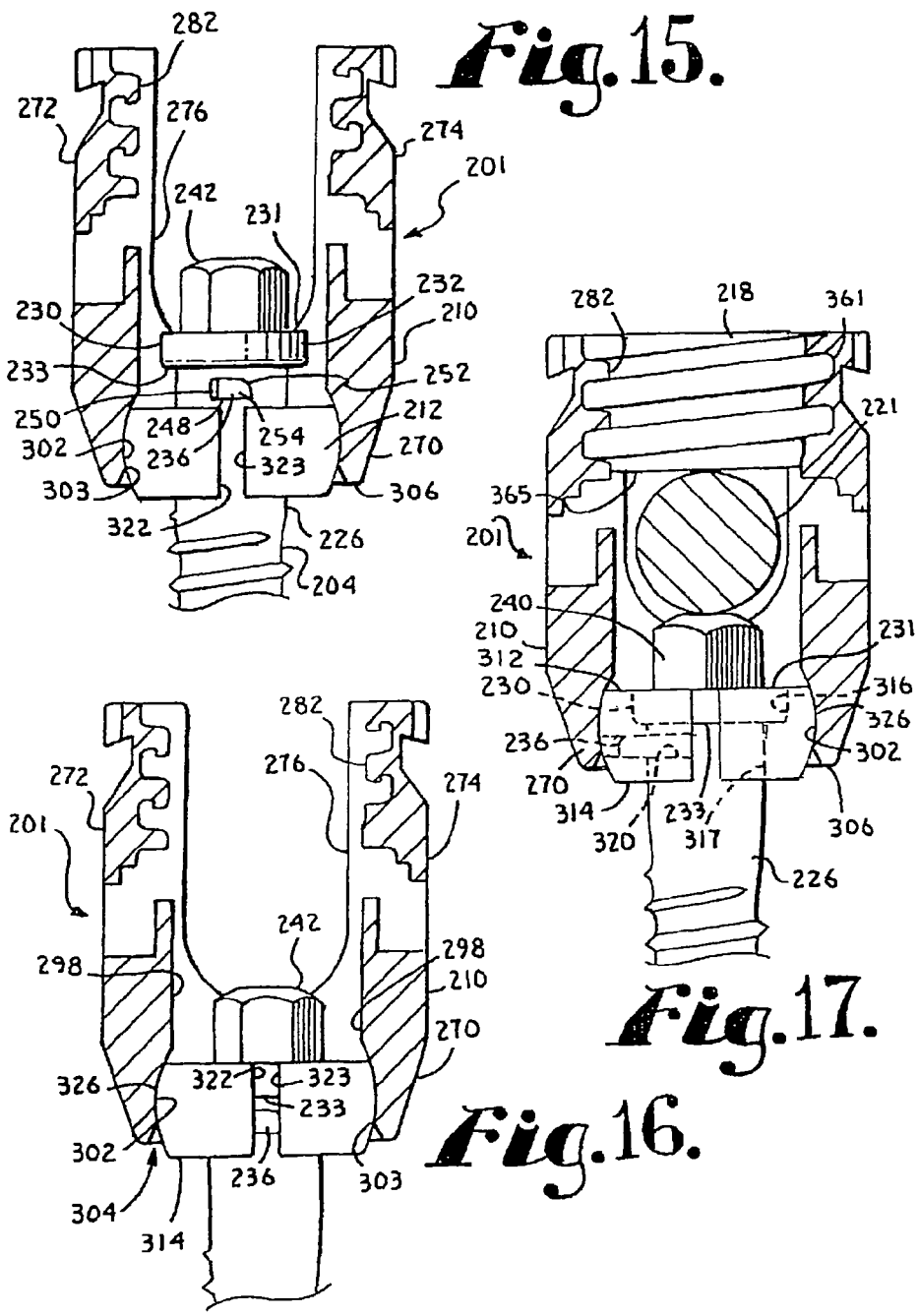

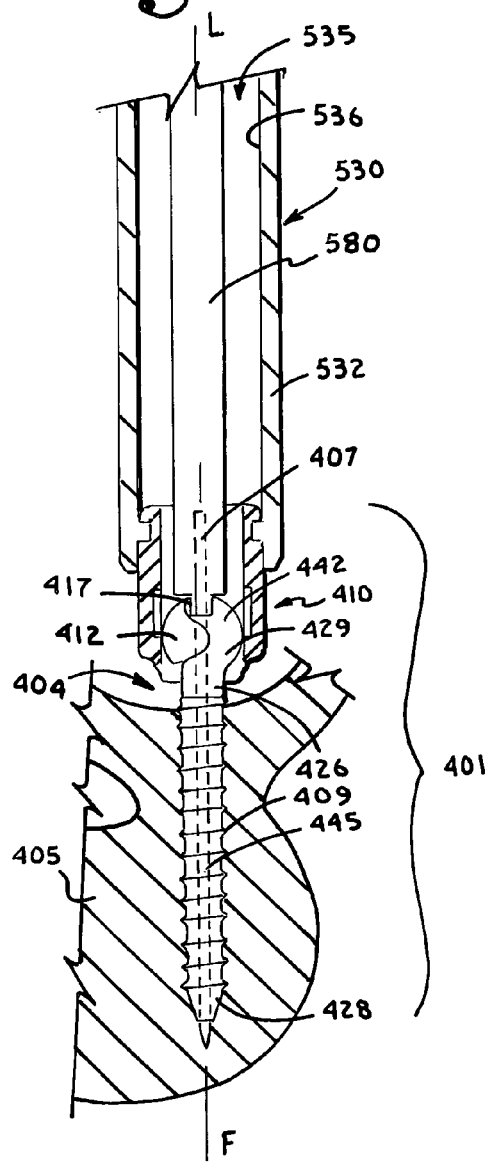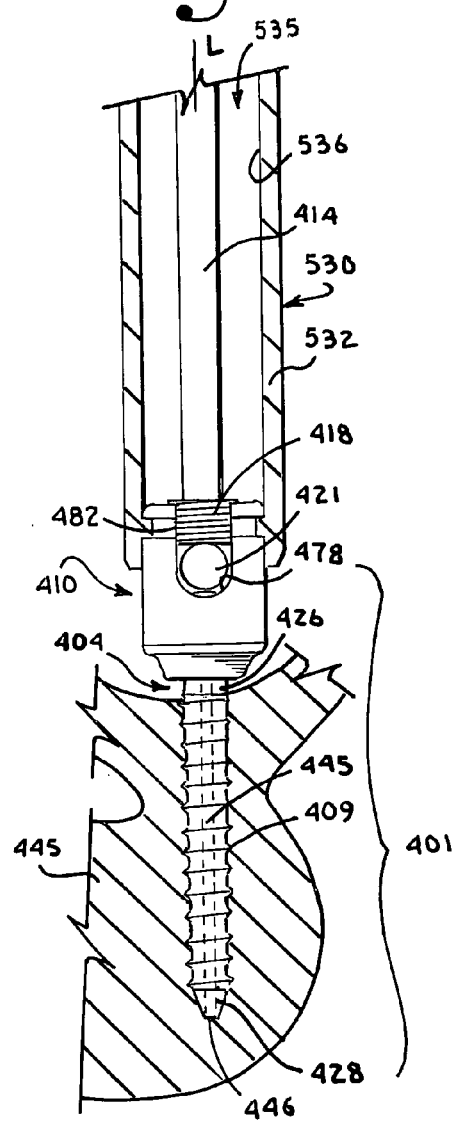

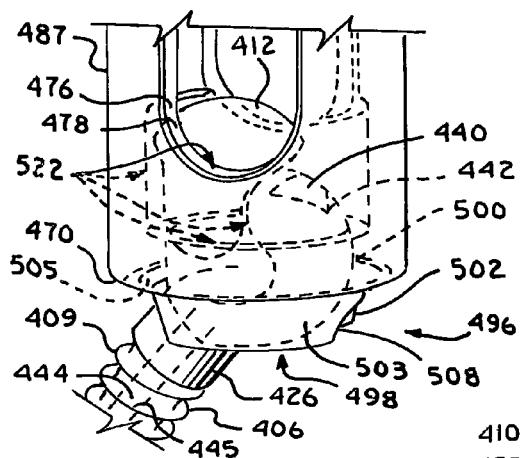
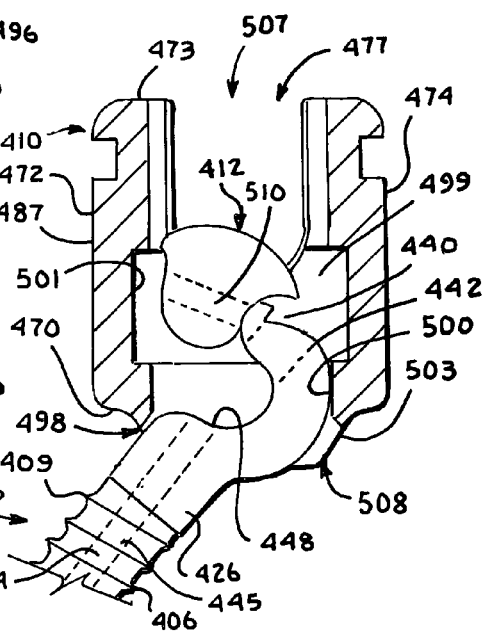
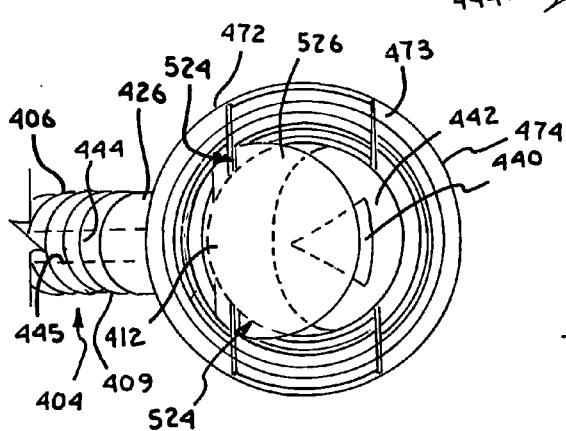

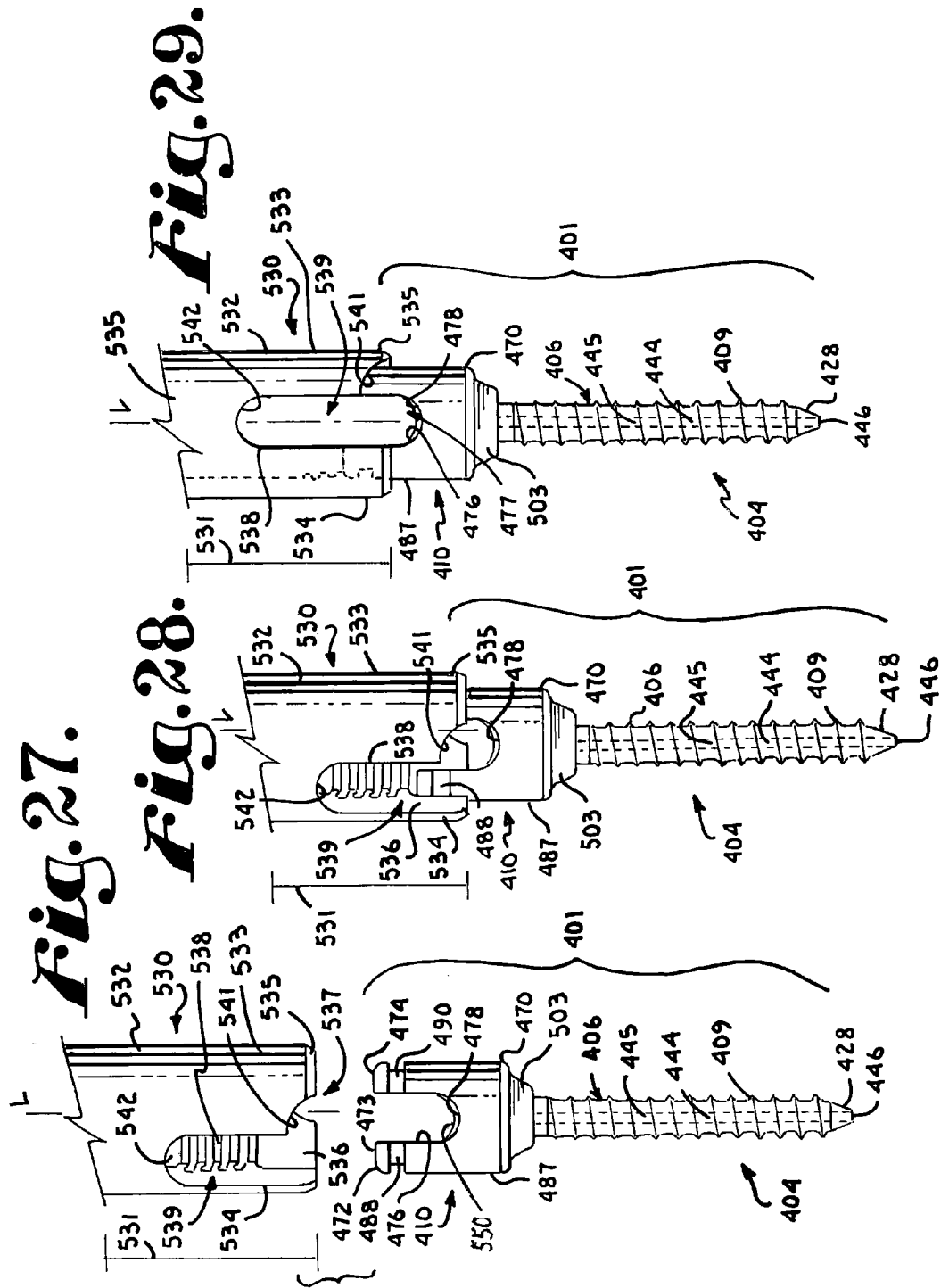

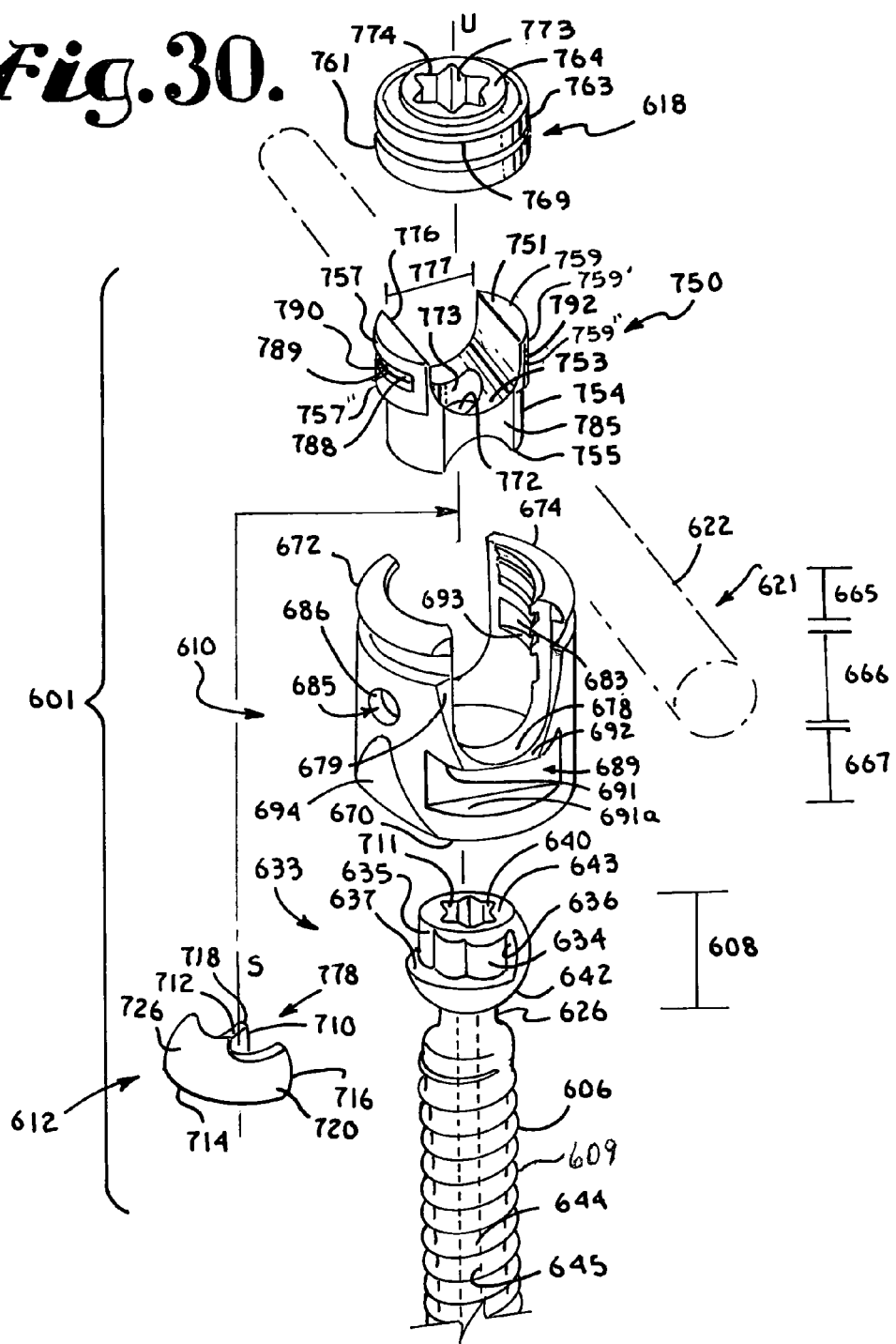

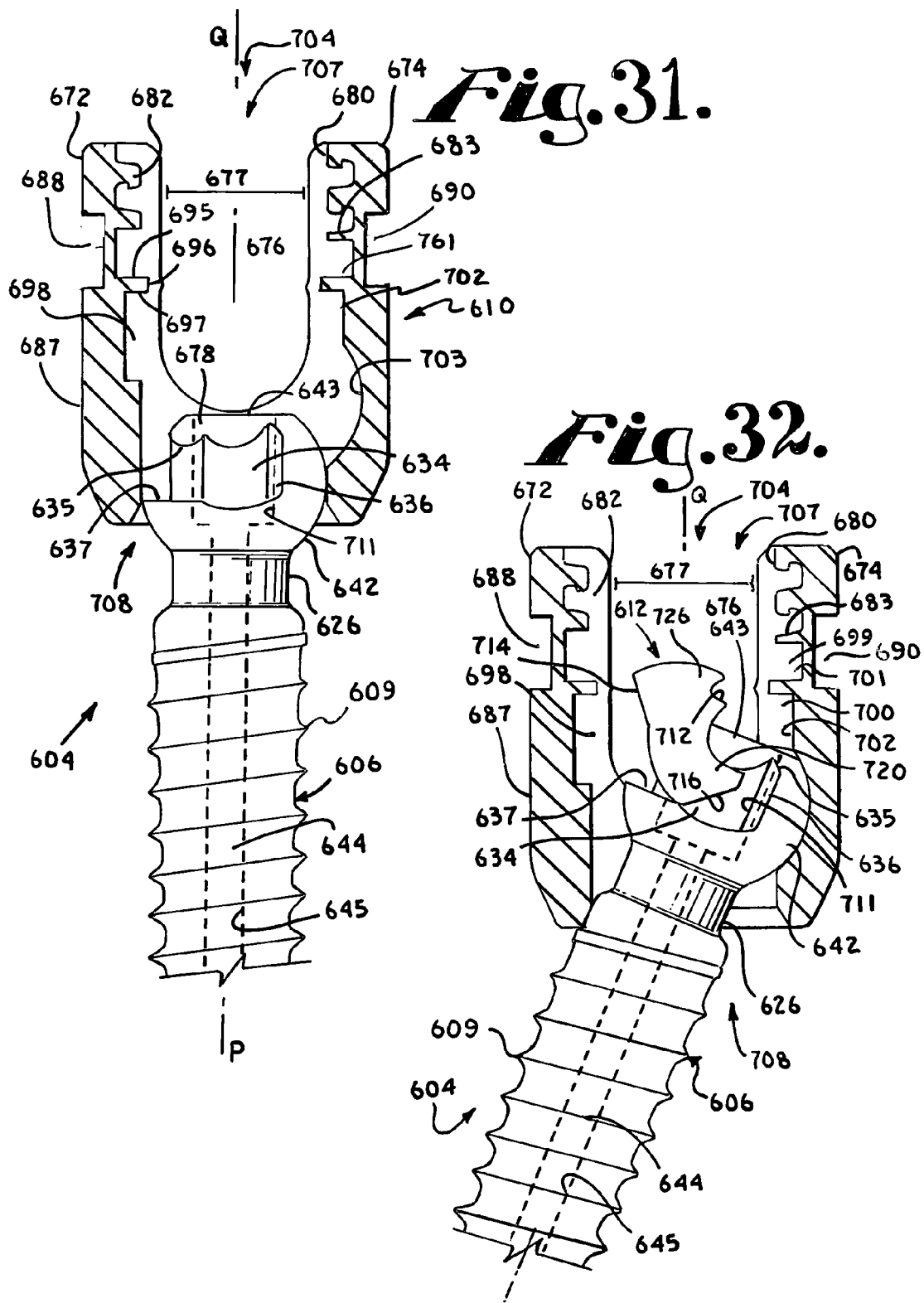

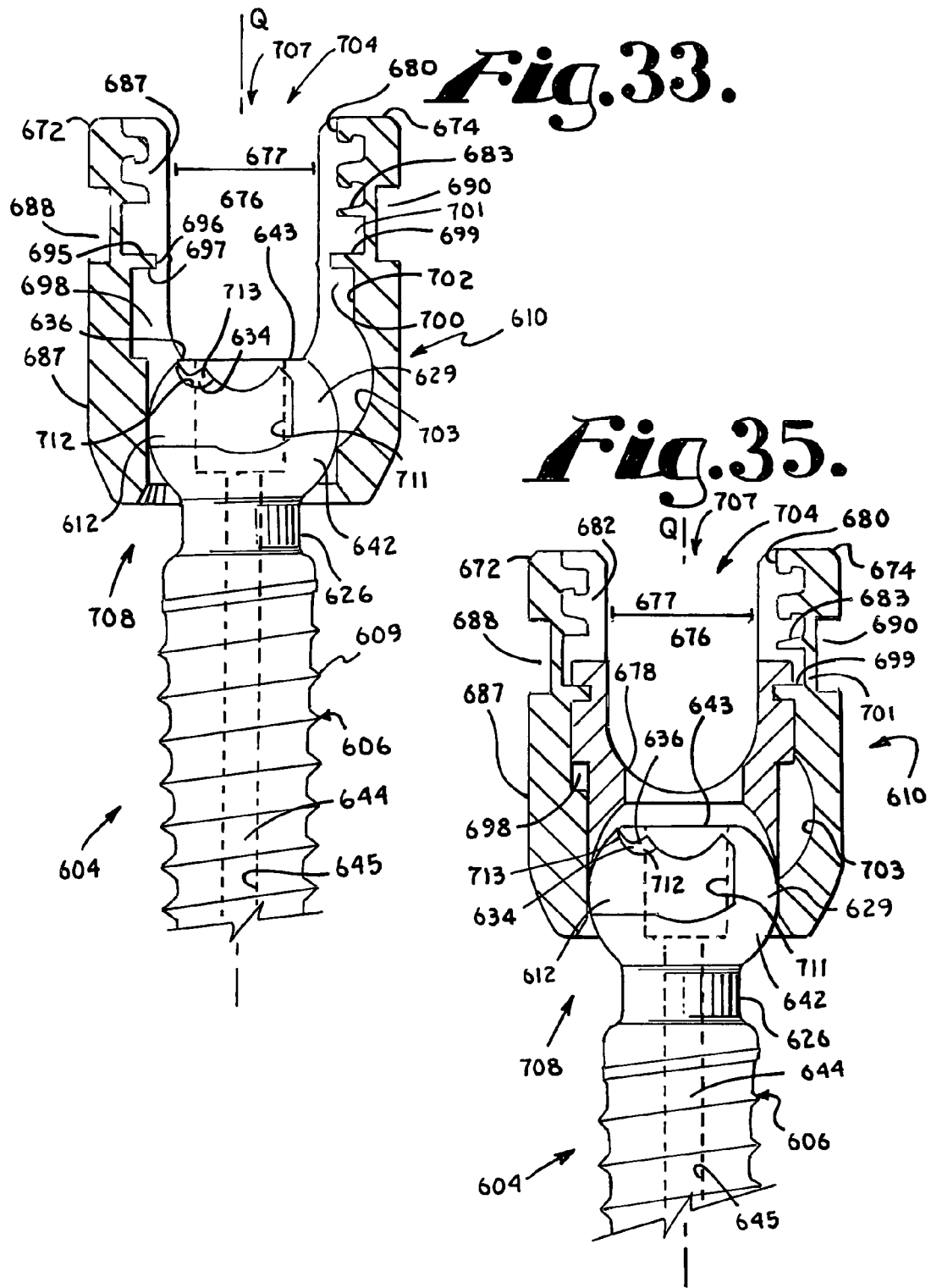

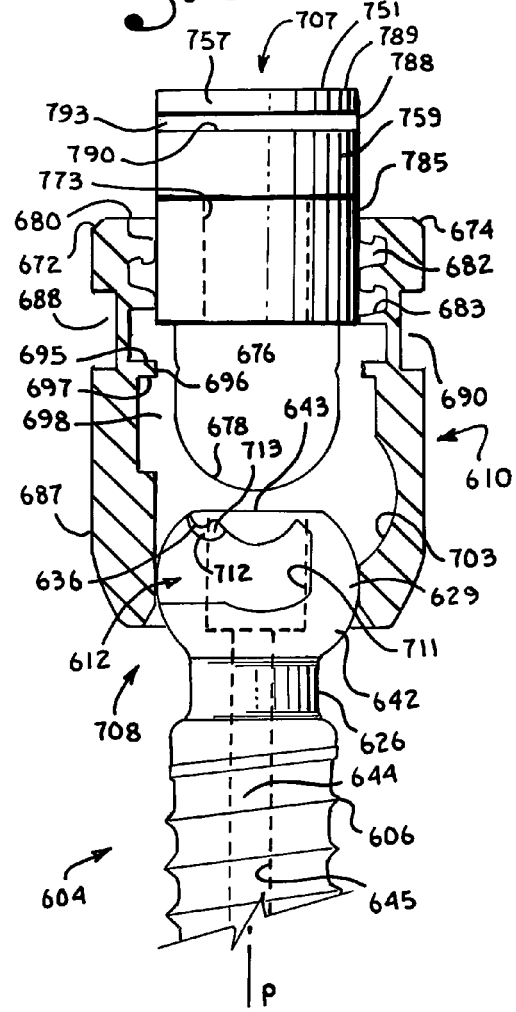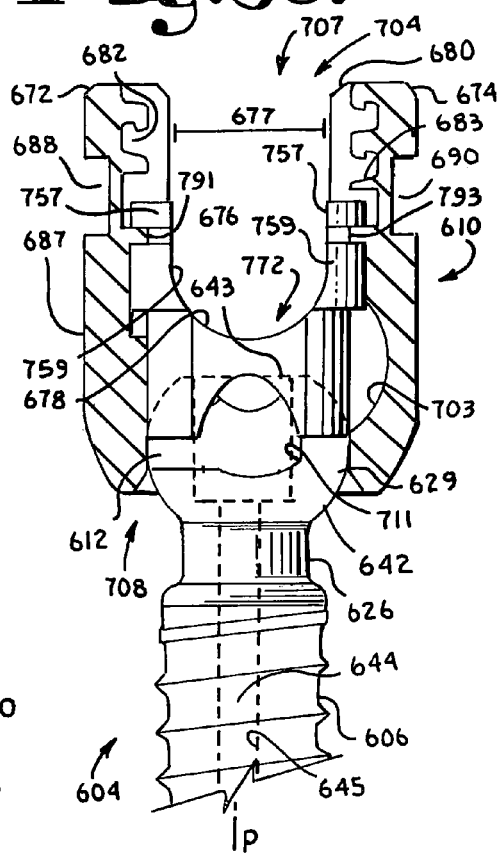

POLYAXIAL BONE SCREW ASSEMBLY

CROSS REFERENCE TO RELATED APPLICATIONS

This application is a Continuation-in-Part of U.S. application Ser. No. 12/800,314, filed May 12, 2010 that claimed the benefit of U.S. Provisional Application No. 61/178,840 filed May 15, 2009, entitled "Polyaxial Bone Screw Assembly", all of which are incorporated herein by reference. U.S. application Ser. No. 12/800,314 was also a continuation-in-part of U.S. patent application Ser. No. 12/009,130, filed Jan. 16, 2008, which is a continuation-in-part of U.S. patent application Ser. No. 10/818,554, filed Apr. 5, 2004, now U.S. Pat. No. 7,662,175, which is a continuation of U.S. patent application Ser. No. 10/464,633, filed Jun. 18, 2003, now U.S. Pat. No. 6,716,214. U.S. patent application Ser. No. 10/818,554 is also a continuation-in-part of U.S. patent application Ser. No. 10/651,003, filed Aug. 28, 2003, the contents of all referenced applicationers are incorporated herein by reference in their entireties.

BACKGROUND OF THE INVENTION

The present invention is directed to polyaxial bone screws for use in bone surgery, particularly spinal surgery. Such screws have a receiver or head that can swivel about a shank of the bone screw, allowing the receiver to be positioned in any of a number of angular configurations relative to the shank.

Many spinal surgery procedures require securing various implants to bone and especially to vertebrae along the spine. For example, elongate members, such as solid rigid rods or more flexible elongate members are often utilized that extend along the spine to provide support to vertebrae that have been damaged or weakened due to injury or disease. Such elongate members must be supported by certain vertebrae and support other vertebrae.

The most common mechanism for providing vertebral support is to implant bone screws into certain bones which then in turn support the elongate member or are supported by the elongate member. Bone screws of this type may have a fixed head or receiver relative to a shank thereof. In the fixed bone screws, the head cannot be moved relative to the shank and the rod must be favorably positioned in order for it to be placed within the head. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod can be inserted into the receiver and eventually the receiver is locked or fixed in a particular position relative to the shank.

A variety of polyaxial or swivel-head bone screw assemblies are available. One type of bone screw assembly includes an open head or receiver that allows for placement of a rod within the receiver. A closure top or plug is then used to capture the rod in the receiver of the screw.

SUMMARY OF THE INVENTION

The present application is related to a polyaxial bone screw assembly and its method of implantation and use. The present application is also related to methods for assembling a polyaxial bone screw assembly.

In some embodiments, a polyaxial bone screw assembly comprises a receiver, a shank, a retainer structure and a bushing. The receiver includes an upper portion having a first opening and a lower portion having a second opening. The upper portion comprises two spaced apart arms that may be internally threaded. The upper portion may further comprise a U-shaped channel extending along a second axis transverse to the first axis adapted to receive a rod member. The shank includes a threaded shaft and an upper head portion having a first partial spherical surface. The retainer structure includes a second partial spherical surface capable of mating with the upper head portion of the shank to form a spherical ball joint. The bushing comprises a lower rounded surface that is capable of engaging the top surface of the spherical ball joint formed by the shank and retainer structure.

Objects and Advantages of the Invention

Certain embodiments of the invention provide an implant wherein all of the parts remain together and do not separate; providing a lightweight, low profile polyaxial bone screw that assembles in such a manner that the components cooperate to create an overall structure that prevents unintentional disassembly; certain embodiments providing a polyaxial bone screw with features adequate frictional or gripping surfaces for bone implantation tools and may be readily, securely fastened to each other and to bone; and certain embodiments provide apparatus and methods that are easy to use and especially adapted for the intended use thereof and wherein the apparatus are comparatively inexpensive to make and suitable for use. Other aspects of the invention descended herein provide advantageous results and advantages not previously formed in the prior art.

Further objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a an exploded perspective view of a polyaxial bone screw assembly according to the present invention having a shank, a receiver, and a retainer with cam track and further shown with a rod and a closure structure.

FIG. 2 is an enlarged top plan view of the retainer of FIG. 1.

FIG. 3 is an enlarged cross-sectional view taken along the line 3-3 of FIG. 2.

FIG. 4 is an enlarged front elevational view of the shank of FIG. 1.

FIG. 5 is a partial exploded view of the shank, retainer and receiver of FIG. 1 with portions broken away to show the detail thereof.

FIG. 6 is a partial view similar to FIG. 5 showing the shank being uploaded into the retainer in a stage of assembly therewith cam connection shown in phantom.

FIG. 7 is a partial view similar to FIGS. 5 and 6 showing the shank after rotation into a frictionally engaged locked assembled position with respect to the retainer with cam connection shown in phantom and further shown with a holding tool.

FIG. 8 is an enlarged top plan view of the shank and retainer of FIG. 1 shown in the locked orientation of FIG. 7.

FIG. 9 is a an exploded perspective view of a second embodiment of a polyaxial bone screw assembly according to the present invention having a shank, a receiver, and a retainer with cam track and further shown with a rod and a closure structure.

FIG. 10 is an enlarged front elevational view of the retainer of FIG. 9.

FIG. 11 is an enlarged rear elevational view of the retainer of FIG. 9 and showing the cam track in phantom.

FIG. 12 is an enlarged top plan view of the retainer of FIG. 9.

FIG. 13 is an enlarged top plan view similar to FIG. 12, also showing the shank of FIG. 9 with portions broken away to show the detail thereof and showing the retainer in a stage of assembly with the shank.

FIG. 14 is an enlarged top plan view similar to FIG. 13 showing the retainer in a subsequent stage of assembly with the shank.

FIG. 15 is a partial front elevation view of the shank, retainer and receiver of FIG. 9 showing the shank and connected retainer of FIG. 14 loaded into the retainer in a stage of assembly therewith portions broken away to show detail of the receiver.

FIG. 16 is a partial view similar to FIG. 15 showing the shank prior to rotation into a frictionally engaged locked assembled position with the retainer.

FIG. 17 is a partial view similar to FIG. 16 showing the shank after rotation into a frictionally engaged locked assembled position with respect to the retainer with cam connection shown in phantom and further shown the closure of FIG. 9.

FIG. 18 is a cross-sectional view of the bone screw assembly after being driven into a vertebra by a driving tool, held in position by a holding tool.

FIG. 19 is cross-sectional view of FIG. 18, of the bone screw assembly after being driven into a vertebra and with a receiver of the assembly fully shown held in position by a holding tool, being locked by a closure being installed by an installation tool.

FIG. 21 is a side view of the third polyaxial bone screw assembly partially assembled and illustrating zones of friction, with parts of the receiver and shank shown in phantom.

FIG. 22 is a partial cross-sectional view of the third polyaxial bone screw assembly partially assembled and prior to fully mating a retainer structure with a shank.

FIG. 23 is a top view of the third polyaxial bone screw assembly partially assembled illustrating zones of friction, with certain internal parts shown in phantom.

FIG. 27 is a side view of a guide tool and the third polyaxial bone screw assembly with portions broken away showing an initial alignment step in attaching the holding tool to the third polyaxial bone screw assembly.

FIG. 28 is a side view of the holding tool with portions broken away showing an intermediate step in attaching the holding tool of FIG. 18 to the polyaxial bone screw assembly of FIG. 20, wherein a slot of the holding tool is not yet aligned with a U-shaped channel of the receiver.

FIG. 29 is a side view of the holding tool with portions broken away showing the holding tool of FIGS. 18-19 attached to the polyaxial bone screw assembly, wherein the holding tool has been rotated 90-degrees clockwise and the slot of the holding tool is substantially aligned with the U-shaped channel of the receiver.

FIG. 30 is a an exploded perspective view of a fourth polyaxial bone screw assembly according to the present invention having a shank, a receiver, a retainer, a bushing, and a closure with a rod shown in phantom.

FIG. 31 is a partial cross-sectional view of the fourth polyaxial bone screw assembly partially assembled and prior to mating a retainer structure with a shank.

FIG. 32 is a partial cross-sectional view of the fourth polyaxial bone screw assembly partially assembled and just prior to mating the retainer with the shank as the retainer is being positioned in the receiver.

FIG. 33 is a partial cross-sectional view of the fourth polyaxial bone screw assembly partially assembled after mating the retainer with the shank.

FIG. 34 is a partial cross-sectional view of the fourth polyaxial bone screw assembly as the bushing is positioned in the receiver.

FIG. 35 is a partial cross-sectional view of the fourth polyaxial bone screw assembly after positioning the bushing in the receiver, and prior to locking the bushing.

FIG. 36 is a partial cross-sectional view of the fourth polyaxial bone screw assembly after the bushing is rotated into a locked position with shank head partially shown in phantom behind the bushing.

DETAILED DESCRIPTION OF EMBODIMENTS OF THE INVENTION

Figure 20:
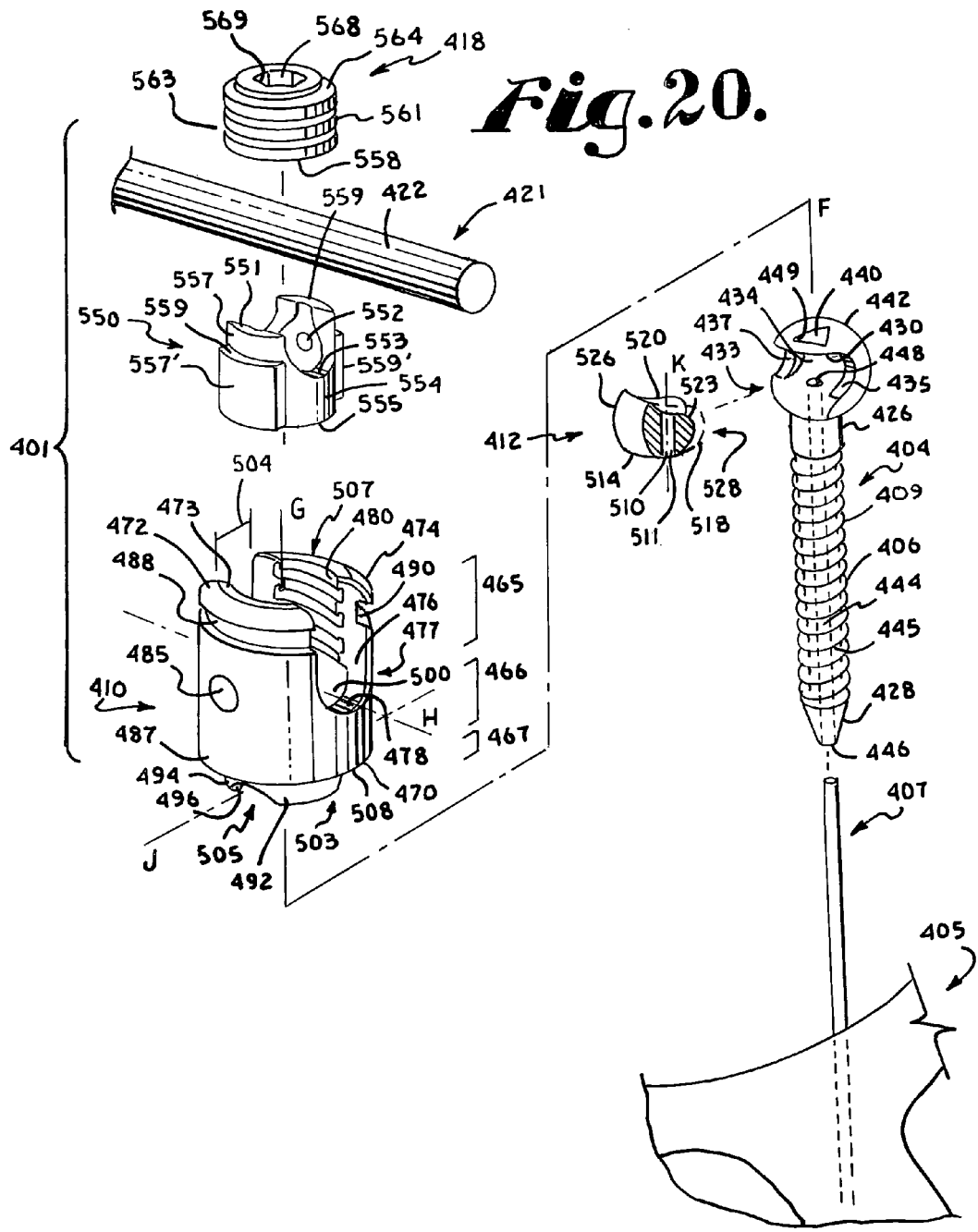
FIG. 20 is a an exploded perspective view of a third embodiment of a polyaxial bone screw assembly according to the present invention having a shank, a receiver, a retainer, and a bushing and further shown with a rod and a closure structure with a partial vertebra and guide wire.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-8, the reference number 1 generally represents an embodiment of a polyaxial bone screw apparatus or assembly according to the present invention. The assembly 1 includes a shank 4 that further includes a threaded body 6 integral with an upper portion 8; a receiver 10; and a closed or integral retainer structure or ring 12. The shank 4, receiver 10 and retainer structure 12 preferably are factory assembled prior to implantation of the shank body 6 into a vertebra (as similarly shown in FIG. 18).

With further reference to FIG. 1, also shown is a closure structure 18 for biasing a longitudinal connecting member such as a rod 21 against the shank upper portion 8 which biases the retainer 12 into fixed frictional contact with the receiver 10, so as to fix the rod 21 relative to the vertebra (as similarly shown in FIG. 18). The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1, 4, 5 and 8, is elongate, with the shank body 6 having a helically wound bone implantable thread 24 extending from near a neck 26 located adjacent to the upper portion 8 to a tip 28 of the body 6 and extending radially outwardly therefrom. During use, the body 6 utilizing the thread 24 for gripping and advancement is implanted into the vertebra (as similarly shown in FIG. 18) leading with the tip 28 and driven down into the vertebra with an installation or driving tool (as similarly shown in FIG. 18), so as to be implanted in the vertebra to near the neck 26, and as is described more fully in the paragraphs below. The shank 4 has an elongate axis of rotation generally identified by the reference letter A.

The neck 26 extends axially upwardly from the shank body 6. The neck 26 may be of reduced radius as compared to an adjacent top 32 of the threaded body 6. Further extending axially upwardly from the neck 26 is the shank upper portion 8 that provides a connective or capture apparatus disposed at a distance from the threaded body top 32 and thus at a distance from the vertebra when the body 6 is implanted in the vertebra (as similarly shown in FIG. 18).

The shank upper portion 8 is configured for a polyaxial connection between the shank 4 and the receiver 10 and capturing the shank 4 upper portion 8 in the receiver 10. The upper portion 8 generally includes a retainer seat portion 33; a substantially cylindrical portion 34 having a laterally extending extension in the form of a lug or tab 36; a tool engagement structure 40 and a top end surface 42. A driving tool is configured to fit about the tool engagement structure 40 so as to form a socket and mating projection for both driving and rotating the shank body 6 into the vertebra (as similarly shown in FIG. 18). In the embodiment shown in the figures, the tool engagement structure 40 is in the shape of a hexagonally shaped extension head coaxial with both the threaded shank body 6 and the shank upper portion 8. Other embodiments of the invention may include up to a plurality of lugs 36, for example, a pair of opposed lateral lugs.

The top end surface 42 of the shank 4 is preferably curved or dome-shaped as shown in the drawings, for contact engagement or positive mating engagement with the rod 21, when the bone screw assembly 1 is assembled, as shown in FIG. 7 and in any alignment of the shank 4 relative to the receiver 10. In certain embodiments, the surface 42 is smooth. While not required in accordance with practice of the invention, the surface 42 may be scored or knurled to further increase frictional positive mating engagement between the surface 42 and the rod 21.

The shank 4 shown in the drawings is cannulated, having a small central bore 44 extending an entire length of the shank 4 along the axis A. The bore 44 is defined by an inner cylindrical wall 45 of the shank 4 and has a first circular opening 46 at the shank tip 28 and a second circular opening 48 at the top surface 42. The bore 44 is coaxial with the threaded body 6 and the capture structure outer surface 34. The bore 44 provides a passage through the shank 4 interior for a length of wire (shown in FIG. 18) inserted into the vertebra (as similarly shown in FIG. 18) prior to the insertion of the shank body 6, the wire providing a guide for insertion of the shank body 6 into the vertebra.

With reference to FIGS. 4 and 5, the retainer seat 33 of the shank upper portion 8 includes a substantially planar annular upper surface 50 disposed perpendicular to the Axis A of the shank and sized and shaped to be bottom loaded in the receiver 10 with a radially extending width sufficient for frictional mating with the retainer 12 as will be described in greater detail subsequently herein. The seat 33 further includes a substantially spherically shaped surface 52 extending from an edge or rim 54 of the flat annular surface 50 and curving downwardly toward the shank body 6 to the neck 26. Although a spherical surface 52 is shown, it is noted that the surface may be conical or otherwise non-spherically curved. In the disclosed embodiment, the surface 52 is flush with an outer surface of the retainer 12 when the seat 33 engages the retainer 12 as will be discussed below.

The cylindrical portion 34 of the shank upper portion 8 is disposed between the seat portion 33 and the tool engagement structure 40. The portion 34 includes a top surface or narrow ledge 56 and a substantially smooth cylindrical surface 58 that runs from the ledge 56 to the annular surface 50 of the seat 33. The surface 58 is uniform about the axis A. The lug 36 extends laterally from the surface 58 near the ledge 56. The lug 36 includes a top surface 60, a bottom surface 61, a pair of opposed and substantially parallel side surfaces 62 and 63 and an outer curved surface 64. The curved surface 64 is cylindrical and coaxial with the surface 58. The top surface 60 extends from the tool engagement structure 40 and in some embodiments may slope slightly downwardly toward the seat 33 as well as outwardly toward the outer surface 64 as illustrated. The bottom surface 61 extends from the cylindrical surface 58 to the outer surface 64. As best illustrated in FIG. 4, the bottom surface 61 is also preferably sloped or ramped at an angle directed downwardly from the side 62 to the side 63 so as to fully frictionally engage a cam track ramped surface of the retainer 12 as will be described in greater detail below. It is foreseen that the bottom surface 61 may also be disposed generally parallel to the seating surface 50 resulting in an edge of the bottom surface 61 ultimately in frictional locking engagement with the cam track of the retainer 12.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate (Ca 3(PO 4) 2, tetra-calcium phosphate (Ca 4P 2 0 9), amorphous calcium phosphate and hydroxyapatite (Ca 10(P0 4) 6(OH) 2). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Referring to FIGS. 1 and 5, the receiver 10 has a generally U-shaped appearance with a partially cylindrical inner profile and a partially curved and partially faceted outer profile; however, the outer profile could also be partially cylindrical. The receiver 10 includes a somewhat curved or spherical base 70 integral with a pair of upstanding arms 72 and 74 forming a U-shaped cradle and defining a U-shaped channel 76 between the arms 72 and 74 with an upper opening 77 and a lower seat 78 having substantially the same radius as the rod 21 for operably snugly receiving the rod 21.

Each of the arms 72 and 74 has an interior surface 80 that defines the inner cylindrical profile and includes a partial helically wound guide and advancement structure 82. In the illustrated embodiment, the guide and advancement structure 82 is a partial helically wound interlocking square thread configured to mate under rotation with a similar structure on the closure structure 18, as described more fully below. However, it is foreseen that the guide and advancement structure 82 could alternatively be a flange form, a buttress thread, a reverse angle thread or other thread like or non-thread like helically wound advancement structures for operably guiding under rotation and advancing the closure top downward between the arms 72 and 74.

Tool engaging apertures 85 are formed on or through surfaces of the arms 72 and 74 that may be used for holding the receiver 10 during assembly with the shank 4 and the retainer structure 12 and also during the implantation of the shank body 6 into a vertebra (as similarly shown in FIG. 18). Furthermore, each of the arms 72 and 74 also includes a V-shaped or undercut tool engagement groove 88 and 90, respectively, formed on outer surfaces thereof which may be used for holding the receiver 10 with a holding tool (shown in FIG. 18) having projections that are received within the grooves 88 and 90 during implantation of the shank body 6 and/or during subsequent installation of the rod 21 and the closure structure 18. It is foreseen that tool receiving grooves or apertures may be configured in a variety of shapes and sizes and be disposed at other locations on the receiver arms 72 and 74.

Communicating with and located beneath the U-shaped channel 76 of the receiver 10 is a chamber or cavity 98 substantially defined by an inner surface 100 of the base 70, the cavity 98 opens upwardly into the U-shaped channel 76. The inner surface 100 is substantially spherical, with at least a portion thereof forming a partial internal spherical seating surface 102 having a first radius. The surface 102 is sized and shaped for mating with the retainer structure 12, as described more fully below.

The base 70 further includes a restrictive neck 103, having a second radius R and defining a bore 104 communicating with the cavity 98 and a lower exterior 106 of the base 50. The bore 104 is coaxially aligned with respect to a rotational axis B of the receiver 10. The neck 103 and associated bore 104 are sized and shaped to be smaller (the second radius) than a radial dimension of the retainer structure 12 (the first radius), so as to form a restriction at the location of the neck 103 relative to the retainer structure 12, to prevent the retainer structure 12 from passing from the cavity 98 and out into the lower exterior 106 of the receiver 10 when the retainer structure 12 is seated within the receiver 10.

The inner surface 100 further defines an elongate upper loading recess 107 for accommodating and loading the retainer structure 12 into the cavity 98. The loading recess 107 is generally vertically disposed in the receiver 10, extending between and communicating with both the channel 76 and the cavity 98, allowing for ease in top loading the retainer structure 12 into the cavity through the upper opening 77 and otherwise allowing for the spherical wall 100 of the receiver 10 to have a comparatively enlarged radius to allow for increased thickness and strength of the receiver base 70; however, the loading recess 107 is not always necessary.

The retainer structure or ring 12 is used to capture the shank upper portion 8 and retain the upper portion 8 within the receiver 10. The retainer 12, best illustrated in FIGS. 2, 3 and 8, has an operational central axis that is the same as the rotational axis A associated with the shank 4, but when the retainer structure 12 is separated from the shank 4, the axis of rotation is identified as axis C, as shown in FIG. 1. The retainer structure 12 has a central bore 110 that passes entirely through the retainer structure 12 from a top surface 112 to a bottom surface 114 thereof. The bottom surface 114 is substantially planar and disposed perpendicular to the axis C. A first inner cylindrical surface 116 defines a substantial portion of the bore 110. The cylindrical surface 116 is sized and shaped to be slidingly received about the cylindrical surface portion 34 of the shank upper portion 8. A slot, generally 118 is formed in the inner surface 116 and also portions of the top surface 112 and the bottom surface 114. The slot 118 may be further described as including a through slot, generally 120 and a cam track, generally 122, the through slot 120 cooperating and communicating with the cam track 122. The through slot 120 is sized and shaped to receive the lug 36 of the shank upper portion therethrough during installation of the retainer 12 on the shank upper portion 8 within the receiver cavity 98. The cam track 122 is sized and shaped to frictionally engage the bottom surface 61 of the lug 36 of the shank upper portion 8, with the retainer 12 bottom surface 114 being seated on the upper surface 50 of the seat 33 of the shank upper portion 8.

With particular reference to FIGS. 2 and 3, the through slot 120 is defined by an inner cylindrical surface 126 coaxial with the cylindrical surface 116. The cylindrical surface 126 also partially defines the cam track 122. At the slot 120, the surface 126 extends between and through the top surface 112 and the bottom surface 114. The through slot 120 is further defined by opposed side surfaces 128 and 130, both of which run parallel to the axis C. The side surface 128 extends between and through the top surface 112 and the bottom surface 114. The side surface 130 begins at the bottom surface 114 and ends at a ramped surface 132 that partially defines the cam track 122. The cam track 122 is further defined by the inner cylindrical surface 126 that extends to a surface or stop 134 that runs substantially parallel to the axis C. Thus, the cam track 122 is defined by a portion of the cylindrical surface 126, the ramped or sloped surface 132 and the stop 134. The ramped surface 132 slopes upwardly in a direction toward the top surface 112 as the surface 132 runs from the surface 130 to the stop 134. A degree of inclination of the surface 132 substantially matches a degree of inclination of the bottom surface 61 of the lug 36. In some embodiments according to the invention, one or both the ramped surface 132 and the lug bottom surface 61 includes a roughening, ridges or some other treatment to further aid frictional locking of the retainer 12 with respect to the lug 36.

The top surface 112 of the retainer 12 in cooperation with the ledge 56 of the shank upper portion 8 provide a surface about the tool engagement structure 40 that is a stable seating surface for the driving tool (shown in FIG. 18). The illustrated slightly curved top surface 112 provides somewhat of a recess to better grip the driving tool (shown in FIG. 18). It is also foreseen that the top surface 112 may be planar or include recesses or apertures for receiving a holding tool therein.

The retainer 12 also has a radially outer partially spherically shaped surface 144 sized and shaped to mate with the partial spherical shaped seating surface 102 of the receiver and having a third radius approximately equal to the first radius associated with the surface 102. The retainer structure third radius is larger than the second radius of the neck 103 of the receiver 10. Although not required, it is foreseen that the outer partially spherically shaped surface 144 may be a high friction surface such as a knurled surface or the like.

The elongate rod or longitudinal member 21 that is utilized with the assembly 1 can be any of a variety of shapes and implants utilized in reconstructive spinal surgery, but is normally a cylindrical elongate structure having a cylindrical surface 146 of uniform diameter and having a generally smooth surface. The longitudinal connecting member 21 may be made from metal, metal alloys or other suitable materials, including plastic polymers such as polyetheretherketone (PEEK), ultra-high-molecular weight-polyethylene (UH-MWP), polyurethanes and composites. The illustrated rod 21 is preferably sized and shaped to snugly seat near the bottom of the U-shaped channel 76 of the receiver 10 and, during normal operation, is positioned slightly above the bottom of the channel 76 at the lower seat 78. In particular, the rod 21 normally directly or abuttingly engages the shank top surface 42 and is biased against the dome shank top surface 42, consequently biasing the shank 4 downwardly in a direction toward the base 70 of the receiver 10 when the assembly 1 is fully assembled. For this to occur, the shank top surface 42 must extend at least slightly into the space of the channel 76 when the retainer structure 12 is snugly seated in the lower part of the receiver cavity 100. The shank 4 and retainer 12 are thereby locked or held in position relative to the receiver 10 by the rod 21 firmly pushing downward on the shank top surface 42.

With reference to FIG. 1, the closure structure or closure top 18 can be any of a variety of different types of closure structures for use in conjunction with the present invention with suitable mating structure on the upstanding arms 72 and 74. In the embodiment shown, the closure top 18 is rotatably received between the spaced arms 72 and 74. The illustrated closure top 18 has a generally cylindrical shaped base 158 with an upwardly extending break-off head 160. The base 158 includes a helically wound guide and advancement structure 161 that is sized, shaped and positioned so as to engage and interlock with the guide and advancement structure 82 on the arms 72 and 74 to provide for rotating advancement of the closure structure 18 into the receiver 10 when rotated clockwise and, in particular, to cover the top or upwardly open portion 77 of the U-shaped channel 76 to capture the rod 21 without splaying of the arms 72 and 74. The guide and advancement structure 161 utilized in accordance with the present invention may take a variety of forms, including the illustrated substantially square thread and also those described in Applicant's U.S. Pat. No. 6,726,689, which is incorporated herein by reference.

The closure structure 18 also operably biases against the rod 21 by advancement and applies pressure to the rod 21 under torquing, so that the rod 21 is urged downwardly against the shank top end surface 42 that extends up into the channel 76. Downward biasing of the shank top surface 42 operably produces a frictional engagement between the rod 21 and surface 42 and also urges the retainer structure 12 toward the base 70 of the receiver 10, so as to frictionally seat the retainer structure external spherical surface 144 fixedly against the partial internal spherical seating surface 102 of the receiver 10, also fixing the shank 4 and retainer structure 12 in a selected, rigid position relative to the receiver 10.

In the embodiment shown, the closure structure break-off head 160 secured to the base 158 at a neck 164 that is sized and shaped so as to break away at a preselected torque that is designed to properly seat the retainer 12 in the receiver 10. The break-off head 160 includes an external faceted surface 165 that is sized and shaped to receive a conventional mating socket type head of a driving tool (shown in FIG. 18) to rotate and torque the closure structure 18. The break-off head 160 may also include a central bore or other drive or manipulation apertures (not shown) for operably receiving manipulating tools.

The closure structure 18 also includes removal tool engagement structure which in the present embodiment is illustrated in phantom as an aperture 168, such as a hex-shaped and axially aligned aperture disposed in the base 158. The aperture 168 is accessible after the break-off head 160 breaks away from the base 158. The aperture 168 is coaxial with the helically wound guide and advancement structure 161 and is designed to receive a driving tool (shown in FIG. 18), such as a hex tool of an Allen wrench type, into the aperture 168 for rotating the closure structure base 158 subsequent to installation so as to provide for removal thereof, if necessary. The aperture 168 may take a variety of tool-engaging forms and may include one or more apertures of various shapes, such as a pair of spaced apart apertures, or a left hand threaded bore, or an easy-out engageable step down bore, or a Torx aperture, or a multi-lobular aperture or the like.

With particular reference to FIGS. 5-8, prior to the polyaxial bone screw assembly 1 being placed in use according to the invention, the ring-like retainer 12 is typically first inserted or top-loaded, into the receiver U-shaped channel 76 and then into the cavity 98 through the vertical loading recess 107 to dispose the structure 12 within the inner surface 100 of the receiver 10. Then, the retainer structure 12 is rotated approximately 90 degrees so as to be coaxial with the receiver 10 and then seated in sliding engagement with the seating surface 102 of the receiver 10 as illustrated in FIG. 5. With reference to FIG. 6, the shank capture structure 8 is then inserted or bottom-loaded into the receiver 10 through the bore 104 defined by the neck 103. The retainer structure 12, now disposed in the receiver 10 is coaxially aligned with the shank capture structure 8 so that the lug 36 is received by and moved through the through slot 120 until the bottom surface 114 of the retainer 12 engages the surface 50 of the seat 33. The retainer 12 is then rotated about the axis A of the shank 4 until the lug 36 is received in the cam track 122. With reference to FIGS. 7 and 8, as the retainer 12 is rotated and the lug 36 is moved toward the stop 134, the lug bottom surface 61 frictionally engages the ramped surface 132 of the cam track 122, frictionally locking the retainer 12 between the lug 36 and the seat 33, the retainer 12 now in fixed coaxial relationship with the shank 4. Preferably, the shank 4 and or the retainer 12 are rotated to fully mate such structures at a factory setting that includes tooling for holding and precisely rotating the shank 4 and/or the retainer 12 until locking frictional engagement therebetween is accomplished. With reference to FIG. 7, a driving tool 180 having an inner surface 182 providing a socket for operatively mating with the shank tool engagement structure 40 is used to hold the shank upper portion 8 while in the receiver 10 during mating rotation of the shank upper portion 8 with the retainer 12. Although not shown, it is noted that the retainer structure 12 may also have tooling features, such as a pair of small apertures so that the retainer 12 is also securely held during the rotation of the lug 36 along the cam track 122. Permanent, rigid engagement of the capture structure 8 to the retainer structure 12 may be further supported by the use of adhesive, a spot weld, a deformation, or the like. At this time both the shank 4 and the retainer 12 are in rotatable and swivelable engagement with the receiver 10, while the shank upper-portion 8 and the lower aperture or neck 103 of the receiver 10 cooperate to maintain the shank body 6 in swivelable relation with the receiver 10. Only the retainer 12 is in slidable engagement with the receiver spherical seating surface 102. The shank upper end 41 and the shank body 6 are in spaced relation with the receiver 10. The shank body 6 can be rotated through a substantial angular rotation relative to the receiver 10, both from side to side and from front to rear so as to substantially provide a universal or ball joint.

In use, the assembly 1 is typically screwed into a bone, such as a vertebra (as similarly shown in FIG. 18), by rotation of the shank 4 using a driving tool (as similarly shown in FIG. 18, but having a socket similar to the socket 182 of the tool 180) that operably drives and rotates the shank 4 by engagement thereof with the tool engagement structure 40 that is in the form of a hexagonally shaped extension head. Preferably, when the driving tool (shown in FIG. 18) engages the engagement structure 40, an end portion thereof engages the ledge 56 and may also engage a portion of the curved retainer top surface 112, providing additional gripping of the driving tool (shown in FIG. 18).

The vertebra may be pre-drilled to minimize stressing the bone and have a guide wire (as similarly shown in FIG. 18) that is shaped for the cannula 44 inserted to provide a guide for the placement and angle of the shank 4 with respect to the vertebra. A further tap hole may be made using a tap with the guide wire as a guide. Then, the assembly 1 is threaded onto the guide wire utilizing the cannulation bore 44 by first threading the wire into the bottom opening 46 and then out of the top opening 48. The shank 4 is then driven into the vertebra, using the wire as a placement guide (as similarly shown in FIG. 18).

The rod 21 is eventually positioned within the receiver U-shaped channel 76, and the closure structure or top 18 is then inserted into and advanced between the arms 72 and 74 so as to bias or push against the rod 21. The break-off head 160 of the closure structure 18 is twisted to a preselected torque, for example 90 to 120 inch pounds, to urge the rod 21 downwardly. The shank top end surface 42, because it is rounded to approximately equally extend upward into the channel 76 approximately the same amount no matter what degree of rotation exists between the shank 4 and receiver 10 and because the surface 42 is sized to extend upwardly into the U-shaped channel 76, the surface 42 is engaged by the rod 21 and pushed downwardly toward the base 70 of the receiver 10 when the closure structure 18 biases downwardly toward and onto the rod 21. The downward pressure on the shank 4 in turn urges the retainer structure 12 downward toward the receiver seating surface 102, with the retainer structure surface 144 in frictional engagement with the receiver seating surface 102. As the closure structure 18 presses against the rod 21, the rod 21 presses against the shank. The retainer structure 12 that is now rigidly attached to the shank 4 is in turn urged downwardly and becomes frictionally and rigidly attached to the receiver 10, fixing the shank body 6 in a desired angular configuration with respect to the receiver 10 and rod 21.

If removal of the assembly 1 and associated rod 21 and closure structure 18 is necessary, disassembly is accomplished by using a driving tool of an Allen wrench type (not shown) mating with the aperture 168 and turned counterclockwise to rotate the base 158 and reverse the advancement thereof in the receiver 10. Then, disassembly of the assembly 1 is accomplished in reverse order to the procedure described previously herein for assembly.

With reference to FIGS. 9-17, the reference number 201 generally represents an alternative embodiment of a polyaxial bone screw apparatus or assembly according to the present invention. The assembly 200 includes a shank 204 that further includes a threaded body 206 integral with an upper portion 208; a receiver 210; and an open retainer structure or ring 212. The shank 204, receiver 210 and retainer structure 212 preferably are factory assembled prior to implantation of the shank body 206 into a vertebra (as similarly shown in FIG. 18).

With further reference to FIG. 9, also shown is a closure structure 218 for biasing a longitudinal connecting member such as a rod 221 against the shank upper portion 208 which biases the retainer 212 into fixed frictional contact with the receiver 210, so as to fix the rod 221 relative to the vertebra (as similarly shown in FIG. 18). The receiver 210 and the shank 204 cooperate in such a manner that the receiver 210 and the shank 204 can be secured at any of a plurality of angles, articulations or rotational alignments relative to one another and within a selected range of angles both from side to side and from front to rear, to enable flexible or articulated engagement of the receiver 210 with the shank 204 until both are locked or fixed relative to each other near the end of an implantation procedure.

The shank 204, best illustrated in FIGS. 9 and 15-17, is elongate, with the shank body 206 having a helically wound bone implantable thread 224 substantially similar to the shank body 6 previously described herein with respect to the assembly 1. The shank 204 has an elongate axis of rotation generally identified by the reference letter E.

A shank neck 226 extends axially upwardly from the shank body 206. Further extending axially upwardly from the neck 226 is the shank upper portion 208 that provides a connective or capture apparatus disposed at a distance from the threaded body 206 and thus at a distance from the vertebra when the body 206 is implanted in the vertebra (as similarly shown in FIG. 18).

Similar to the assembly 1, the shank upper portion 208 of the assembly 201 is configured for a polyaxial connection between the shank 204 and the receiver 210 and capturing the shank 204 upper portion 108 in the receiver 210. The upper portion 208 generally includes a retainer seat portion 230 that is substantially cylindrical having an upper annular surface 231, an outer cylindrical surface 232 and a lower annular surface 233. The seat portion 230 extends radially outwardly from the neck 226. The upper and lower surfaces 231 and 233 are both disposed substantially perpendicular to the axis E. Located on the neck 226 and near the lower annular seat surface 233 is a laterally extending extension in the form of a lug or tab 236. Extending upwardly axially from the upper annular surface 231 is a tool engagement structure 240 having a top end surface 242. A driving tool is configured to fit about the tool engagement structure 240 so as to form a socket and mating projection for both driving and rotating the shank body 206 into the vertebra (as similarly shown in FIG. 18). Specifically in the embodiment shown in the figures, the tool engagement structure 240 is in the shape of a hexagonally shaped extension head coaxial with both the threaded shank body 206 and the shank upper portion 208. The upper annular surface 231 provides a seating surface for the driving tool (shown in FIG. 18). The top end surface 242 of the shank 204 is preferably curved or dome-shaped as shown in the drawings, for contact engagement or positive mating engagement with the rod 221, when the bone screw assembly 201 is assembled, as shown in FIG. 17 and in any alignment of the shank 204 relative to the receiver 210. In certain embodiments, the surface 242 is smooth. While not required in accordance with practice of the invention, the surface 242 may be scored or knurled to further increase frictional positive mating engagement between the surface 242 and the rod 221.

The shank 204 shown in the drawings is cannulated, having a small central bore 244 extending an entire length of the shank 204 along the axis E. The bore 244 is coaxial with the threaded body 206 and the capture structure outer surface 232. The bore 244 provides a passage through the shank 204 interior for a length of wire inserted into the vertebra prior to the insertion of the shank body 206, the wire providing a guide for insertion of the shank body 206 into the vertebra (as similarly shown in FIG. 18). To provide a biologically active interface with the bone, the threaded shank body 206 may be coated, perforated, made porous or otherwise treated as previously described herein with respect to the shank body 6 of the assembly 1.

With particular reference to FIG. 15, the shank upper portion 208 is sized and shaped to be bottom loaded in the receiver 210 with a compressed retainer 212 connected thereto, the retainer seat portion having an un-compressed or neutral radially extending width sufficient for frictional mating with the retainer 212 as will be described in greater detail subsequently herein. When attached to the shank in an operational position, the retainer 212 engages both the cylindrical surface 232 and the lower annular surface 233 of the shank upper portion 208. It is noted that although a cylindrical surface 232 is shown, the surface may have another shape such as polygonal, spherical, conical or otherwise curved. In the disclosed embodiment, the upper surface 231 is flush with a top surface of the retainer 212 when the seat 230 engages the retainer 212 as will be discussed below. The lug 236 that extends laterally from the neck 226 near the lower annular surface 233 includes a lower or bottom surface 248, a side surface 250 disposed substantially perpendicular to the bottom surface 248 and a curved or sloping surface 252 extending between and connecting the bottom surface 248 and the side surface 248. The side surface 250 is disposed substantially parallel to the axis E. The surfaces 248, 250 and 252 also define an outer curved surface 254 that is cylindrical and coaxial with the neck 226. The surface 252 is preferably sloped or ramped at an angle directed downwardly from the side 250 so as to fully frictionally engage a cam track ramped surface of the retainer 212 as will be described in greater detail below. As with the assembly 1 previously described herein, other surfaces of the lug 236 may be sloped or ramped to result in frictional locking engagement with the cam track of the retainer 212.

Referring to FIGS. 9 and 15-17, the receiver 210 is substantially similar to the receiver 10 of the assembly 1. In particular, for example, the receiver 210 includes a base 270, arms 272 and 274 forming a U-shaped channel 276, a guide and advancement structure 282, a cavity 298 partly defined by a spherical seating surface 302, and a neck 303 defining a bore 304 opening into a base lower exterior 306, that are the same or substantially similar to the respective base 70, arms 72 and 74, U-shaped channel 76, guide and advancement structure 82, cavity 98, spherical seating surface 102, neck 103, bore 104 and lower exterior 106 previously described herein with respect to the bone screw assembly 1.

The retainer structure or ring 212 is used to capture the shank upper portion 208 and retain the upper portion 208 within the receiver 210. The retainer 212, best illustrated in FIGS. 10-14, has an operational central axis that is the same as the rotational axis E associated with the shank 204. The retainer structure 212 has a central bore 310 that passes entirely through the retainer structure 212 from a top surface 312 to a bottom surface 314 thereof. The bottom surface 314 is substantially planar and disposed perpendicular to the axis C. A first inner or upper cylindrical surface 316 defines a portion of the bore 310. A second inner cylindrical surface 317 defines a remainder of the bore 310, the surface 317 having a diameter smaller than a diameter of the surface 316. An annular seat or step 318 connects the first cylindrical surface 316 with the second cylindrical surface 317, the seat 318 being disposed substantially parallel to the top surface 312 and the bottom surface 315 and perpendicular to the cylindrical surfaces 316 and 317. The seat 318 is sized and shaped to fully engage the lower annular surface 233 of the shank upper portion 208. The cylindrical surface 316 is sized and shaped to be slidingly received about the cylindrical surface portion 232 of the shank upper portion 208 while the cylindrical surface 317 is sized and shaped to be slidingly received around the shank neck 226. A cam track or slot 320 is formed in the inner surface 317. The cam track 320 is sized and shaped to receive the lug 236 of the shank upper portion 208 during installation of the retainer 212 on the shank upper portion 208 within the receiver cavity 298. The cam track 320 is sloped or ramped with respect to the axis E and sized and shaped to frictionally engage the lug surfaces 248 and 252, with the retainer 212 seat or step 318 being ultimately frictionally seated on the lower surface 233 of the shank upper portion 208.

As stated above, the retainer 212 is in the form of an open or discontinuous ring, having end surfaces 322 and 323 running through the top surface 312 and the bottom surface 314. The cam track 320 is open at the end surface 322 and sized and shaped to receive the lug 236 therein. The retainer 212 further includes an outer partially spherical surface 326 sized and shaped for slidably mating with the receiver spherical seating surface 302. Formed in the outer surface 326 are at least a pair of expansion grooves 328 running between the top surface 312 and the bottom surface 314, the grooves 328 allowing for the opening or spreading apart of the end surfaces 322 and 323 during installation of the retainer 212 on the shank 204 as will be described in greater detail below. In some embodiments according to the invention, one or more lug 236 surfaces and/or surfaces defining the cam track 320 may include a roughening, ridges or some other treatment to further aid frictional locking of the retainer 212 with respect to the lug 236.

The top surface 312 of the retainer 212 in cooperation with the upper surface or ledge 231 of the shank upper portion 208 provide a surface about the tool engagement structure 240 that is a stable seating surface for the driving tool (shown in FIG. 18). Although not required, it is foreseen that the outer partially spherically shaped surface 326 may be a high friction surface such as a knurled surface or the like.

The elongate rod or longitudinal member 221 that is utilized with the assembly 201 can be any of a variety of implants utilized in reconstructive spinal surgery as described above with respect to the 21 of the assembly 1. The rod 221 normally directly or abutingly engages the shank top surface 242 and is biased against the dome shank top surface 242, consequently biasing the shank 204 downwardly in a direction toward the base 270 of the receiver 210 when the assembly 201 is fully assembled. For this to occur, the shank top surface 242 must extend at least slightly into the space of the channel 276 when the retainer structure 212 is snugly seated in the lower part of the receiver cavity 302. The shank 204 and retainer 212 are thereby locked or held in position relative to the receiver 210 by the rod 221 firmly pushing downward on the shank top surface 242.

With reference to FIGS. 9 and 17, the closure structure or closure top 218 can be any of a variety of different types of closure structures for use in conjunction with the present invention with suitable mating structure on the upstanding arms 272 and 274. In the embodiment shown, the closure top 218 is rotatably received between the spaced arms 272 and 274. The illustrated closure top 218 is generally cylindrical in shape and includes a helically wound guide and advancement structure 361 that is sized, shaped and positioned so as to engage and interlock with the guide and advancement structure 282 on the arms 272 and 274 to provide for rotating advancement of the closure structure 218 into the receiver 210 when rotated clockwise and, in particular, to cover the top or upwardly open portion of the U-shaped channel 276 to capture the rod 221 without splaying of the arms 272 and 274. The guide and advancement structure 361 utilized in accordance with the present invention may take a variety of forms, including the illustrated substantially square thread and also those described in Applicant's U.S. Pat. No. 6,726,689, which is incorporated herein by reference.

The closure structure 218 also operably biases against the rod 221 by advancement and applies pressure to the rod 221 under torquing, so that the rod 221 is urged downwardly against the shank top end surface 242 that extends up into the channel 276. Downward biasing of the shank top surface 242 operably produces a frictional engagement between the rod 221 and surface 242 and also urges the retainer structure 212 toward the base 270 of the receiver 210, so as to frictionally seat the retainer structure external spherical surface 326 fixedly against the partial internal spherical seating surface 302 of the receiver 210, also fixing the shank 204 and retainer structure 212 in a selected, rigid position relative to the receiver 210.

In the embodiment shown, the closure structure includes a top surface 364 and an opposed bottom substantially planar surface 365. The top surface 364 has an internal drive feature 366 formed thereon shown as a star-shaped or Torx aperture sized and shaped to receive a driving tool (shown in FIG. 18). The aperture 366 may take a variety of tool-engaging forms and may include one or more apertures of various shapes, such as a pair of spaced apart apertures, or a left hand threaded bore, or an easy-out engageable step down bore, hex drive or multi-lobular aperture or the like.

With particular reference to FIGS. 12-14, prior to the polyaxial bone screw assembly 201 being placed in use according to the invention, the ring-like retainer 212 is first inserted onto the shank 204 at the neck 226. With reference to FIG. 13, the retainer end surfaces 322 and 323 are pulled away from one another, the retainer 212 thereby expanding to receive the shank neck 226 within the inner walls 316 and 317 with the retainer top surface 312 facing the shank upper portion 208. The expansion grooves 328 compress as the retainer 212 is expanded. Once the neck of the shank 204 is past the end surfaces 322 and 323 as shown in FIG. 14, the retainer 212 returns to a neutral non-expanded substantially circular configuration. The retainer 212 is then compressed with the end surfaces 322 and 323 being pushed toward one another to a touching or near touching configuration. While in such a compressed orientation, the shank upper portion 208 and the compressed retainer 212 are up or bottom loaded into the receiver 210 at the neck 303. Once both the upper portion 208 and the retainer 212 are within the receiver cavity 298, pressure is released from the retainer 212 and the end surfaces 322 and 323 are allowed to return to an original spaced and neutral position as illustrated in FIG. 15 with the retainer outer surface 326 in sliding engagement with the receiver seating surface 302. With reference to FIG. 16, the shank capture structure 208 is then lowered into the retainer 212 with the lug 236 disposed between the end surface 322 and the end surface 323. The retainer 212 or the shank 204 is then rotated with respect to the axis E of the shank 104 with the lug 236 entering the cam track 320 at the surface 322. With reference to FIGS. 16 and 17, as the retainer 212 or the shank 208 is rotated, the lug 236 is moved along the sloped cam track 320 until the track terminates or the lug is otherwise fully frictionally engaged with surfaces defining the track 320 and with the retainer annular seating surface 318 fully frictionally engaged with the shank lower annular surface 233, frictionally locking the retainer 212 between the lug 236 and the lower seat or surface 233, the retainer 212 now in fixed coaxial relationship with the shank 204. Preferably, the shank 204 and or the retainer 212 are rotated to fully mate such structures at a factory setting that includes tooling for holding and precisely rotating the shank 204 and/or the retainer 212 until locking frictional engagement therebetween is accomplished. Although not shown, it is noted that the retainer structure 212 may also have tooling features, such as a pair of small apertures so that the retainer 212 is also securely held during the rotation of the lug 236 along the cam track 320. Permanent, rigid engagement of the capture structure 208 to the retainer structure 212 may be further supported by the use of adhesive, a spot weld, a deformation, or the like. At this time both the shank 204 and the retainer 212 are in rotatable and swivelable engagement with the receiver 210, while the shank upper portion 208 and the lower aperture or neck of the receiver 210 cooperate to maintain the shank body 206 in swivelable relation with the receiver 210. Only the retainer 212 is in slidable engagement with the receiver spherical seating surface 302. The shank body 206 can be rotated through a substantial angular rotation relative to the receiver 210, both from side to side and from front to rear so as to substantially provide a universal or ball joint.

In use, the assembly 201 is typically screwed into a bone, such as a vertebra, by rotation of the shank 204 using a driving tool that operably drives and rotates the shank 204 by engagement thereof with the tool engagement structure 240 that is in the form of a hexagonally shaped extension head.

The vertebra may be pre-drilled to minimize stressing the bone and have a guide wire that is shaped for the cannula 244 inserted to provide a guide for the placement and angle of the shank 204 with respect to the vertebra (as similarly shown in FIG. 18). A further tap hole may be made using a tap with the guide wire as a guide. Then, the assembly 201 is threaded onto the guide wire utilizing the cannulation bore 244. The shank 204 is then driven into the vertebra, using the wire as a placement guide.

The rod 221 is eventually positioned within the receiver U-shaped channel 276, and the closure structure or top 218 is then inserted into and advanced between the arms 272 and 274 so as to bias or push against the rod 221. The shank top end surface 242, because it is rounded to approximately equally extend upward into the channel 276 approximately the same amount no matter what degree of rotation exists between the shank 204 and receiver 210 and because the surface 242 is sized to extend upwardly into the U-shaped channel 276, the surface 242 is engaged by the rod 221 and pushed downwardly toward the base 270 of the receiver 210 when the closure structure 218 biases downwardly toward and onto the rod 221. The downward pressure on the shank 204 in turn urges the retainer structure 212 downward toward the receiver seating surface 302, with the retainer surface 326 in frictional engagement with the receiver seating surface 302. As the closure structure 218 presses against the rod 221, the rod 221 presses against the shank. The retainer structure 212 that is now rigidly attached to the shank 204 is in turn urged downwardly and becomes frictionally and rigidly attached to the receiver 210, fixing the shank body 206 in a desired angular configuration with respect to the receiver 210 and rod 221.

If removal of the assembly 201 and associated rod 221 and closure structure 218 is necessary, disassembly is accomplished by using a driving tool of Torx wrench type (not shown) mating with the aperture 366 and turned counterclockwise to rotate the closure structure 218 and reverse the advancement thereof in the receiver 210. Then, disassembly of the assembly 201 is accomplished in reverse order to the procedure described previously herein for assembly.

With reference to FIGS. 18-30, the reference number 401 generally represents an embodiment of a polyaxial bone screw apparatus or assembly according to the present invention. The assembly 401 includes a shank 404 that further includes a threaded body 406 integral with an upper portion 408; a receiver 410; and a retainer structure 412. The shank 404, receiver 410 and retainer structure 412 preferably are factory assembled prior to implantation of the shank body 406 into a vertebra 405, but may also be assembled at the site of usage.

With reference to FIG. 20, also shown is a closure structure 418 for biasing a longitudinal connecting member such as a rod 421 indirectly against the shank upper portion 408 which biases the retainer 412 and the shank upper portion 408 into fixed frictional contact with the receiver 410, so as to fix the angular position of the shank 404 relative to the receiver and fixes the position of the rod 421 relative to the vertebra 405. In particular, the rod member 421 rests on a bushing 550, which in turn rests on the top of the shank 404 as described below. The receiver 410 and the shank 404 cooperate in such a manner that the receiver 410 and the shank 404 can be secured at any of a plurality of angles, articulations or rotational alignments relative to one another and within a selected range of angles both from side to side and from front to rear, to enable flexible or articulated engagement of the receiver 410 with the shank 404 during positioning until both are locked or fixed relative to each other near the end of an implantation procedure.

In some embodiments, to assemble the bone screw assembly, first the shank 404 is inserted into the receiver 410 through the bottom of the receiver 410. Subsequently, the retainer structure 412 is slid into the receiver 410 and mated with an upper head portion 408 of the shank 404 to form a ball 429 (shown in FIGS. 23-24). Next, the bushing 550 is slid into the top of the receiver 410 over the spherical ball formed by the shank 404 and the retainer 412 (shown in FIGS. 24-26). The assembled shank 404, retainer structure 412 and receiver 410 are preferably then joined with a vertebra 405 by screwing the shank body 406 into a vertebra 405 or the like, such as a pedicle, ilium, or sacrum (shown in FIGS. 18 and 19). It is foreseen that the shank 404 first be screwed into the vertebra 405 and then the retainer structure 412 and receiver 410 joined therewith. Thereafter, a rod 421 or elongate member can be delivered to be coupled with the bone screw assembly 401. In some embodiments, a cap screw or closure member 418 can be downwardly inserted into the receiver 410 to apply a downward compression force on the rod 421. The force of the cap screw 418 on the rod 421 is be transmitted to the ball joint 429 to lock the shank 404 at a fixed angle by compressive forces.

Illustrated in FIG. 18, the shank 404 is elongate, with the shank threaded body 406 having a helically wound bone implantable thread extending from a neck 426 portion of the threaded body 406 located adjacent to the upper portion 408 to a tip 428 of the body 406 and extending radially outwardly therefrom. To provide a biologically active interface with the bone, the threaded shank body 406 may be coated, perforated, made porous or otherwise treated as previously mentioned.

The shank 404 is cannulated, having a small central bore 444 extending an entire length of the shank 404 along an axis F. The bore 444 is defined by an inner cylindrical wall 445 of the shank 404 body 406; a second inner cylindrical wall 511 in the retainer structure 412 (shown in FIG. 20); an inner triangular wall 449 in the shank head portion 408; and six openings, including a first circular opening 446 at the shank tip 428; a second circular opening 448 along a first engagement wall 434 on the bottom surface of a undercut portion 430 in a mating segment 433; a third circular opening (not shown) along the first engagement wall 434 on the top surface of the undercut portion 430 in the mating segment 433; a fourth opening, a tool engagement aperture 440; a fifth opening 511 along a second engagement wall 523; and a sixth opening (not shown) on a bottom surface 515 of the retainer structure 412. The bore 444 is coaxial with the threaded body 406 and axis F, through the upper head portion 408 of the shank 404 and through the retainer structure 412 coaxial with an axis K. The bore 444 provides a passage through the shank 404 and an interior of the retainer structure 412 interior for a length of wire 407 inserted into the vertebra 405 prior to the insertion of the shank body 406 (shown in FIG. 18).

Illustrated in FIG. 18, during use, the body 406 utilizing the thread 409 for gripping and advancement is implanted into the vertebra 405 leading with the tip 428 and driven down by rotating into the vertebra 405 with an installation or driving tool 580 so as to be implanted in the vertebra 405 to near the neck 426. A wire 407 provides a guide for insertion of the shank body 406 into the vertebra 405. The upper portion 408 generally includes the tool engagement aperture 440 and a partially spherical surface top end surface 442. As seen in FIG. 18, the driving tool 580 is configured to fit about the tool engagement aperture 440 so as to form a socket and mating projection for both driving and rotating the shank body 406 into and reversibly from the vertebra 405. When the driving tool 580 is mounted on the bone screw head 408, the mating portion 417 of the driving tool 580 extends downwardly around and into a tool engagement aperture 440. Preferably, when the driving tool 580 engages the inner triangular wall 449, the mating portion 417 may also engage a portion of the curved surface 442 of the shank head 408, providing additional gripping of the driving tool 580.

The vertebra 405 may be pre-drilled to minimize stressing the bone and have the guide wire 407 that is shaped for the cannula bore 444 inserted to provide a guide for the placement and angle of the shank 404 with respect to the vertebra 405. It is foreseen that the bore 444 may be threaded using a tap (not shown) with the guide wire as a guide. The guide wire 407 is placed into the cannulation bore 444 by first threading the wire 407 into the bottom opening 446 and then out of the top opening 440. The shank 404 is then driven into the vertebra 405, using the wire 407 as a placement guide after which the wire 407 is removed.

Illustrated in FIGS. 21-26, the tool engagement aperature 440 is in the shape of a triangular shaped depression coaxial with both the threaded shank body 406 and the shank upper portion 408. It is also foreseen that the top surface 442 may have a planar surface or include recesses or apertures of other shapes for receiving numerous different shapes of driving tool 580 therein. If removal of the shank 404 is necessary, disassembly is accomplished by using the driving tool 580 mating with the tool engagement aperture 440 and turned counterclockwise to rotate the shank 404 and reverse the advancement thereof from the vertebra 405.

Referring to FIG. 20, the shank neck 426 extends axially upwardly from the shank body 406. The neck 426 may be of reduced radius as compared to an adjacent top 408 of the threaded body 406. Further extending axially upwardly from the neck 426 is the shank upper portion 408 that provides a capture or mating segment 433 disposed at a distance from the threaded body 406 and thus at a distance from the vertebra 405 when the body 406 is implanted in the vertebra 405. From the uppermost portion 408 of the shank 404 a surface extends transversely in a first direction away from the longitudinal axis F of the shank 404 and then curves back in an opposite, second direction to form an overhang over an undercut portion 430 defining the mating segment 433 to a matching segment 528 in the retainer structure 412.

The mating segment 433 in one embodiment includes a first engagement wall 434 extending along a middle of the undercut portion, and a pair of recesses 435 and 437 extending from lateral sides of the first engagement wall 434 in the first direction. The recesses 435 and 437 comprise inwardly sloping surfaces relative to the engagement wall 434. The engagement surface 434 in this embodiment is generally concaved sized and shaped to be capable of receiving the matching convex mating surface 528 of the retainer structure 412. It is foreseen, in other embodiments, the engagement wall 434 can be convex and the mating surface 528 can be concave. While in this embodiment, the engagement wall surface 434 is smooth and mates with a like smooth mating surface 528, it is foreseen that the surface 434 may be roughened to increase frictional mating between the engagement wall 434 and mating surface 528.

The shank upper portion 408 is configured for a polyaxial connection between the shank 404 and the receiver 410 by capturing the shank 404 upper portion 408 in the receiver 410. The top end surface 442 of the upper portion 408 of the shank 404 is preferably curved or dome-shaped as shown in the drawings, for contact engagement or positive mating engagement with the bushing 550, when the bone screw assembly 401 is assembled, as shown in FIGS. 18 and 19 and in any alignment of the shank 404 relative to the receiver 410. In certain embodiments, the top end surface 442 is smooth. While not required in accordance with practice of the invention, the surface 442 may be scored or knurled to further increase frictional positive mating engagement with the bushing 550.

Referring to FIG. 20, the receiver 410 has a generally U-shaped appearance with a partially cylindrical inner profile and a partially curved and partially faceted outer profile; however, the outer profile 487 could also be partially spherical. The receiver 410 has three portions: an upper portion 465, an intermediate portion 466, and a lower portion 467. A bore 504 is defined by interior surface 480 and extends from a first upper opening 507 to a second lower opening 508 along an axis G. It is noted that at times, axis F, G, L will coaxially align with each other. The bore 504 provides a passage through the receiver 410 for the bushing 550 and the retainer structure 412 as described below. In other embodiments, receiver 410 may include one or more of the features discussed above for receivers 10, 210 and 610.

The receiver 410 includes a somewhat curved or cylindrical base 470 integral with a pair of upstanding arms 472 and 474 forming a U-shaped cradle that defines a U-shaped channel 476 extending along an axis H transverse to the axis G. The U-shaped channel 476 between the arms 472 and 474 creates gaps 477 and a lower seat 478 having substantially the same radius as the rod 421 for operably snugly receiving the rod 421 slightly spaced from a seat 478 of the channel 476. The rod member 421 is loaded downwardly in the first opening 507 and through the gaps 477, until the surface of the rod 421 rests near the bottom portion seat 478 of the U-shaped channel 476 (shown in FIG. 19). The rod member 421 rests on the bushing 550, as the bushing 550 extends upward into the channel 476, as described below. In some embodiments, the U-shaped channel 476 has substantially the same radius as the rod member 421 so as to be capable of snugly receiving the rod member 421 on the sides thereof, while it is foreseen that in other embodiments, the U-shaped channel 476 may have a slightly larger radius. The top of the rod member 421 when inserted in the U-shaped channel 476 is located at a lower end of the guide and advancement structure 482 formed on the arms 472 and 474 of the receiver 410, as discussed below.

Referring to FIG. 20, the arms 472 and 474 are generally symmetrical and shaped similarly, although in some embodiments one arm can be sized or shaped differently from another. Each of the arms 472 and 474 defines an interior surface 480 that forms the inner cylindrical profile of the receiver 410 and includes in one embodiment a smooth surface. Interior surface 480 comprises a cylindrical body having a radius equal to the shortest distance between the inner wall of arms 472 and 474 and a point on the axis G. The inner cylinder formed is not a continuous solid due to the gaps 477 formed between the arms 472 and 474. The interior surface 480 includes a partial helically wound guide and advancement structure 482.

In the illustrated embodiment in FIG. 20, the guide and advancement structure 482 along the interior surface 480 is a partial helically wound interlocking flange form configured to mate under rotation with a similar structure on the closure structure 418, as described more fully below. However, it is foreseen that the guide and advancement structure 482 could alternatively be a square thread, a buttress thread, V-shaped threads, a reverse angle thread or other thread like or non-thread like helically wound advancement structure for operably guiding under rotation and advancing the closure top 418 downward between the arms 472 and 474. In some embodiments, the internal threads or guide 482 comprise helically wound forms capable of interlocking with other surfaces as described in Applicant's U.S. Pat. No. 6,726,689, which is incorporated herein by reference in its entirety. In other embodiments, a thread relief or abutment surface is incorporated.

Tool engaging apertures 485 and interior surfaces 486 are formed on or through exterior surfaces 487 of the arms 472 and 474 that may be used for holding the receiver 410 during assembly with the shank 404 and the retainer structure 412 and also during the implantation of the shank body 406 into a vertebra 405. The opening 485 can be used to couple with one or more holding instruments having protruding members or indentors. For example, in one technique, a protruding tab member of a surgical instrument can be received within the opening interior surface 486 to mate the surgical instrument with the receiver 410. While FIG. 20 illustrates a single opening 485 on one side of the receiver 410, the receiver 410 can also include a second opening on the opposite side of the receiver 410. In other embodiments, a plurality of openings 485 can be provided around the surface of the receiver so as to provide multiple receiving or coupling areas.

Furthermore, each of the arms 472 and 474 also includes a V-shaped or C-shaped undercut tool engagement groove 488 and 490, respectively, formed on outer surface 487 thereof which may be used for holding the receiver 410 with a holding tool 530 as described later (shown in FIGS. 18, 19, 27-29). The grooves 488 and 490 are radiused perpendicularly with respect to the axis G and are preferable horizonitally aligned. In the present embodiment, the grooves 488 and 490 extend internally from one side to the an opposite side of a respective arm 472 and 474. It is foreseen that the grooves 488 and 490 may only extend part way or be slightly sloped to produce a cam effect. The tool engagement grooves 488 and 490 form a shoulder that extends from one edge of an arm 472 adjacent a U-shaped channel 476 on one side of the receiver 410 to a second edge of the arm 474 adjacent a U-shaped channel 476 on the other side of the receiver 410. In other embodiments, it is foreseen that the grooves 488 and 490 need not extend across the entire surface of an arm 472 from one edge to another. For example, one end of the groove 488 can begin midway through the arm 472 and continue to edge of the arm 474. The grooves 488 and 490 have an inward or interior surface 484. The grooves 488 and 490 form a track feature on each arm 472 and 474. It is foreseen, in some embodiments, an holding instrument 530 (shown in FIGS. 18, 19, 27-29) having a wound guide 543 interior that can slideably engage and mate with the surface of the grooves 488 and 490. The holding instrument 530 is positioned so that the wound guide 543 are aligned with and then rotated so as to be placed within the grooves 488 and 490, thereby providing a secure attachment between the holding instrument 530 and the receiver 410.

Figure 26:
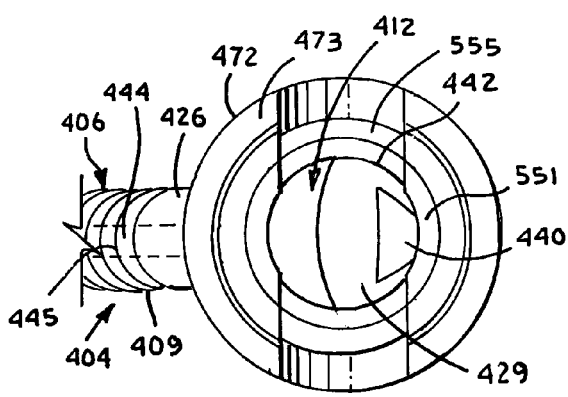
FIG. 26 is a top view similar to FIG. 24, of the third polyaxial bone screw assembly.

Illustrated in FIG. 20, a restrictive neck 503 is located on the base 470. The neck 503 is formed by extend downwardly to produce spaced lower legs or arms 492 and 494. The arms 492 and 494 are defined by a cut-out portion 505 forming and defining upside down U-shaped channel 495 extending along an axis J transverse to the axis G and running perpendicular to the axis H. It is foreseen that the axis J may not run perpendicular to axis H. Upside down U-shaped channel 495 between the arms 492 and 484 creates gaps 496. The inner surface of arms 492 and 494 create a shaped wall 502 in the interior surface of the restrictive neck 503 as shown in FIGS. 21, 24 and 26.

Figure 24:
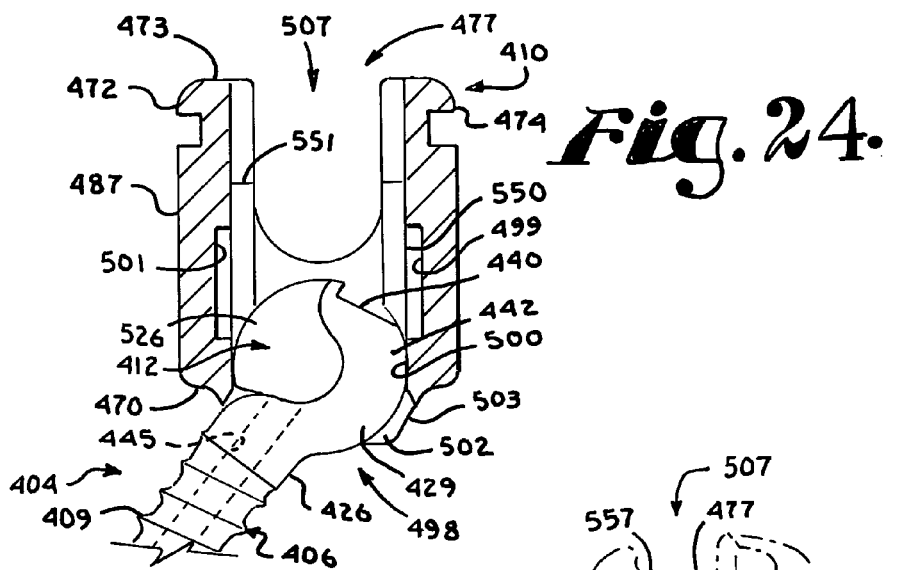
FIG. 24 is a cross-sectional view of partially assembled polyaxial bone screw assembly with the retainer fully mated with the shank.

Illustrated in FIGS. 22 and 24, a partially continuous inner recess 499 is formed on the interior surface 480 beneath the guide and advancement structure 482. It is foreseen, the inner recess 499 may comprise substantially cylindrical inner walls 501 that form a continuous cylinder having a radius larger than the radius of the cylindrical shape formed by the internal threads in the interior surface 480 of the receiver 410. The inner recess 499 is sized and shaped to receive protrusions 557 and 559 of the bushing 550 (as described later). It is foreseen that the inner recess 499 may be rectangularly shaped and form a continuous cylinder, and in other embodiments, the inner recess 499 can comprise a rounded recess that does not form a cylinder.

Illustrated in FIGS. 22 and 24, communicating with and located above the second opening 508 of the receiver 410 is a chamber or cavity 498. The cavity 498 communicates upwardly into the bore 504 and downwardly to the second opening 508. The cavity 498 is defined by a inner continuous cylindrical friction wall 499 and the friction wall 500. The continuous friction wall 500 is formed below the inner surface 480 of the receiver 410 and has a smaller radius than that of the recess 499, and may have a radius substantially similar to the cylinder formed by the interior surface 480. The continuous friction wall 500 transitions into the inner shaped wall 502 of the restrictive neck 503. It is foreseen that, in one embodiment, the shaped wall 502 is tapered inward and forms an inverted conical surface that has a cross-sectional radius smaller than the cylinder formed by the continuous friction wall 500. It is also foreseen that the interior of the shaped wall 502 may be rounded. The shaped wall 502 is sized and shaped for mating with the head portion 408 of the shank 404, which is uploaded into the cavity 498 through the lower opening 508 where the shank 404 mates with retainer 412 to form the ball 429 which has a larger diameter than the opening 508 so as to secure the shank 404 in the receiver 410, but allow polyaxial rotation of the shank 404 relative to the receiver 410 during positioning and until later locked. The retainer structure 412 polyaxially rotates with the shank 404 relative to the receiver 410 during positioning.

It is foreseen that, in some embodiments, prior to insertion through the second opening 508 of the receiver 410, the shank 404 axis F is kept in coaxial alignment with the longitudinal axis G of the receiver, while in other embodiments, the shank 404 is kept at an angle from the longitudinal axis G of the receiver 410, such as between 1 and 90 degrees, or between 25 and 70 degrees. The shank 404 can be inserted vertically through the second opening 508. Using a cut-away portion 505 of the cavity 498 (as shown in FIG. 20), the shank 404 can be angulated, if not angulated already or more precisely angulated such that the shank 404 may be aligned at an angle between 30 and 60 degrees, more preferably about 45 degrees, such that the outer partial spherical surface 442 of the shank 404 rests firmly against the interior of the receiver 410 (e.g., against the friction wall 500 as seen in FIGS. 21-26). It is also foreseen that in some embodiments, the head portion 408 of the shank 404 can be placed into firm contact with both the friction wall 500 and the shaped wall 502 of the restrictive neck 417, as shown in FIGS. 22-27. When the shank 404 is appropriately angulated within receiver 410, the retainer structure 412 can be pre uploaded or downloaded through the channel 476 into the receiver 410 to mate with the head 408 of the shank 404 to form the spherical ball 430 (shown in FIGS. 24-26). The shank 404 is normally bottom loaded into the receiver 410, which allows the diameter of the lower portion of the shank 404 to be larger than would fit through the channel 476 to increase the strength of the shank 404.

Referring to FIG. 20, the retainer structure 412, has an operational central axis K that is the same as the rotational axis F associated with the shank 404 and can be aligned or non-aligned with the axis G associated with the receiver 410 when assembled, but when the retainer structure 12 is separated from the shank 404, the central axis of rotation is identified as an axis K.

Illustrated in FIG. 20, the retainer structure 412, in one embodiment comprises a second partial spherical outer portion 526 and a second mating section 528. A pair of protrusions 518 and 520 extend from each side of a second engagement wall surface 523, which is convex. The protrusions 518 and 520 and the second engagement wall 523 make up the second mating segment 528. The protrusions 518 and 520 are sized and shaped to mate with the pair of recesses 435 and 437 of the head portion 408 of the shank 404 when the retainer structure 412 is joined or snap fitted into place with the shank 404 in the receiver 410. Joining the retainer structure 412 and the upper head portion 408 of the shank 404 also results in a fitting contact between the concave surface of the first engagement wall 434 and the convex surface of the second engagement wall 523. In this embodiment, when joined together, the retainer structure 412 and shank 404 form the large sphere or ball 429 that is engageable with the lower inner rounded surface 555 of the bushing 550 (shown in FIGS. 24-26). The retainer structure 612 has a central bore 510 through the second engagement wall 523 that once mated with the shank 404 that further defines the bore 444. The retainer 412 is not joined with the shank 404 until both are in the receiver 410. This allows the shank 404 to be uploaded through the lower opening 508 in the receiver 410, as the shank 404 upper portion 408 fits through the opening 508 when not joined with the retainer structure 412, but the ball 429 created by the joining of the shank 404 and the retainer 412 has a larger diameter than the lower opening, thereby capturing the shank 404 in the receiver 410.

Referring to FIGS. 21-23 are side and top views of a partially assembled polyaxial bone screw assembly illustrating zones of friction 522 and 524 during assembly. The shank 404 and retainer structure 412 are held in place not just by joining or snap fitting, but also by frictional forces between surfaces. Frictional forces 522 and 524 also exist between the elements during screw assembly.

FIGS. 21-23 illustrates a retainer structure 412 being delivered downwardly or top-loaded through the channel 476 of the receiver 410 prior to mating with the shank 404. Illustrated in FIG. 21, the retainer structure 412 is initially delivered down the receiver 410 in such a manner that the retainer structure 412 makes frictional contact with the inner wall 501 of the receiver 410. This may require some twisting or rotating, depending upon the angle by which the shank 404 is bottom-loaded. The contact between the retainer structure 412 and the inner wall 501 create several zones of friction 496. The zones of friction 522 provide greater control over the retainer structure 412 during assembly by preventing slipping of the retainer structure 412 with the inner wall 501 of the receiver 410.

FIG. 22 illustrates a fragmentary cross-sectional view of a partially assembled polyaxial bone screw assembly 401, in which the upper head portion 408 of the shank is in contact with both the continuous friction wall 500 and shaped wall 502 and is ready to receive and securely join with the retainer structure 412, preferably with a frictional joining or snug locking. In contrast to the shank 404 which was bottom-loaded through the receiver 410, the retainer structure 412 is preferably top-loaded through the upper surface of the receiver 410. The rounded upper head portion 408 makes firm contact with the friction wall 500 and shaped wall 502. The retainer structure 412 is then delivered downwardly or top-loaded through the first opening 507 at the top of the receiver 410. The retainer structure 412 makes contact with the upper head portion 408 of the shank 404 and is then joined or snap fitted into place to form the spherical ball member 429. Once the retainer structure 412 and shank 404 are joined together into place inside the receiver 410, the bushing 550 is delivered downwardly through the top of the receiver 410, as shown in FIGS. 24-27.

In addition, referring to FIG. 23, during assembly, zones of friction 524 are formed between the upper head portion 408 of the shank 404 against the inner wall 502 of the receiver 410 as the retainer structure 412 pushes against the shank 404. The zones of friction 524 provide greater control over the shank 404 while the retainer structure 412 is delivered to mate with the shank 404. It is foreseen that in some embodiments, frictional forces 522 and 524 between the retainer structure 412 and the inner wall 501 are maintained while the retainer structure 412 is in the process of engagement with the head portion 408 of the shank 404 to help ensure that the retainer structure 412 does not back out or become removed during the engagement process.

Referring to back to FIG. 20, in the illustrated embodiment, the bushing 550 includes an upper surface 551, a seat 553, an exterior surface 554, a lower rounded surface 555, and upward extending arms 557 and 559. The bushing 550 is used to capture the shank upper portion 408 and retain the upper portion 408 within the receiver 410, while independently locking the portion of the shank 404 relative to the receiver 410. In addition, the bushing 550 further comprises U-shaped channel 576 between the arms 557 and 559 that create gaps 577 and a lower seat 553 having substantially the same radius as the rod 621 for operably snugly receiving the rod 621. The seat 553 of the bushing 550 substantially matches the shape and size of the bottom surface of the U-shaped channel 476 of the receiver 410, such that the two can be aligned to allow a rod member 421 to be delivered into the seat 553 and bottom surface of the U-shaped channel 476. In this embodiment, the bushing 550 further comprises a bottom inward sloping spherical surface 555 that mates with or is substantially similar to the outer surface 442 of the upper portion 408 of the shank 404 and outer surface 526 of the retainer structure 412.

In this embodiment, protrusions 557' and 559' are sized and shaped so as to fit into the recess 499 of the receiver 410. The protrusions 557' and 559' are rounded with a cylindrical, convex outer surface 554. The protrusions 557' and 559' comprise a projection or a spline to be fitted into the recess 499 of the receiver 410. One skilled in the art will appreciate that the protrusions 557' and 559' can be of various shapes and sizes. It is foreseen in some embodiments, bushing 550 may comprise one of the bushings or incorporate one or more of the bushing elements described or covered in U.S. Pat. No. 7,377, 923 and U.S. patent application Ser. No. 12/290,244, which are incorporated herein by reference in their entireties.

FIG. 24 is a partially cross-sectional side view of the polyaxial bone screw assembly, prior to placement of the bushing 550 downwardly into the receiver 410. The bushing 550 is initially oriented such that the pair of outwardly extending protrusions 557' and 559' face the gaps 477 formed by the arms 472 and 474 of the receiver 410 (shown in FIG. 25). The bushing 550 is then slideably deposited downwardly through the top opening 507 of the receiver 410 and along the gaps 477 until the lower inner rounded surface 555 rests firmly on the spherical ball member 429 formed by the mated shank 404 and retainer structure 412.

Figure 25:
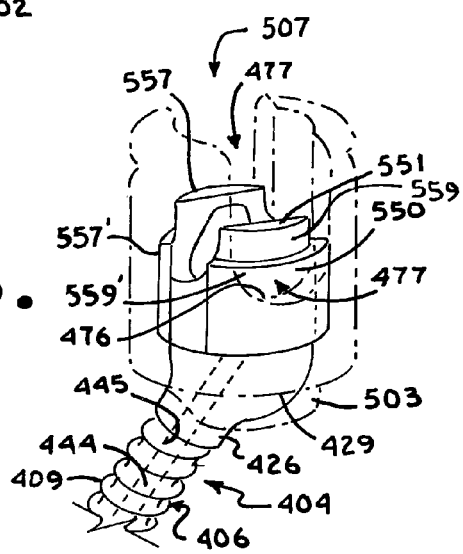
FIG. 25 is a side view of a polyaxial bone screw assembly with the bushing located in the receiver, with the receiver shown in phantom.

Referring to FIG. 25, once the bushing 550 has been deposited such that the inner rounded surface 553 rests on the surface formed by the shank 404 and the retainer structure 412, the bushing 550 is then rotated until the protrusions 557' and 559' are received into the recess 499. To fit the protrusions 557' and 559' into the recess 499, the bushing 550 is rotated 90 degrees, thereby securing the bushing 550 relative to the receiver 410. The bushing 550 is rotated into place using an instrument or automated using a fixture, which is normally done at a factory. It is foreseen that in some embodiments, the bushing 550 can include one or more additional protrusions (not shown) in addition to the protrusions 557' and 559' on the outer wall 554 of the bushing 550 that will cause an interference fit with an inner wall (not shown) of the receiver when the bushing 550 is rotated into place. The additional protrusions can assist in preventing the bushing 550 from rotating under normal loading conditions.

FIG. 26 is a top view of a fully assembled polyaxial bone screw assembly 401. As seen from above, the spherical ball member 429 formed by the upper head portion 408 of the shank 404 mated with retainer structure 412 appear as a dome surface 442. The bushing 550 has been rotated about 90 degrees relative to the initial loading such that the protrusions 557' and 559' of the bushing 550 fit into the recess 499 of the receiver 410. The spherical ball 429 creates a joint by initially resting on the shaped wall 502 of the lower portion 467 of the receiver 410 and is capable of multi-axial rotation and angulation. While the degree of angulation can vary, it is foreseen that preferably the spherical ball 429 joint is capable of angulation (e.g., between 1 and 90 degrees) in many different directions. From the top view, it is easy to see that the spherical ball member is capture and secured by the bushing 550, while the bushing itself is secured to the receiver 410. With each subsequent additional element, the polyaxial bone screw assembly 401 becomes more and more secure from disassembly.

It is possible to disassemble the bone screw assembly 401 by removing the frictional bond between the deposited bushing 550 and the shank 404. Several ways to remove the frictional bond between the deposited bushing 550 and the shank 404 are described. An aperture 552, in any shape, is provided in the bushing 550 that allows an external instrument to engage with the aperture 552 to facilitate disengagement between the bushing 550 and the shank 404. The aperture 552 can be located in the outside of the receiver 410 such that an instrument (not shown) can extend into the aperture 552 and press against a top portion of the bushing 550, thereby reducing the friction between the bushing 550 and the shank 404. It is foreseen that in other embodiments, an aperture 552 can be placed in the inner wall of the receiver 410 such that an instrument (not shown) can enter through the interior of the receiver 410 to rotatably remove the bushing 550 from the receiver 410. The instrument can then pull the bushing 550 away from shank 404 to reduce the friction. It is foreseen that in other embodiments, a first instrument (not shown) can be provided that has the shape of the bushing seat 553, and a second instrument (not shown) can be provided that holds the receiver 410 rigid, while the first instrument is used to rotate the bushing 550 by 90 degrees, thereby reversing the assembly process and disengaging the bushing 550 from the assembly 401. Thus, using the disassembly methods described above, it is possible to restore the variable angular capability of the shank 404.

Illustrated in FIGS. 18, 19, 27-29, the holding tool 530 of the present invention has a substantially cylindrical elongate body 532 that is sized and shaped to be sufficiently long to extend from an attached implanted bone screw assembly 401 through an exterior of a patient's skin so as to provide an outwardly extending upper handle portion (not shown) that allows and provides for gripping by a surgeon during procedures utilizing the holding tool 530.

Referring to FIGS. 27-29, a bottom portion 531 of the holding tool 530 is shown. A body 532 of the holding tool 530 includes outer surface 533 and side walls 534, wherein the outer surface 533 is cylindrically shaped and extends from a top to the bottom portion 531 of the holding tool 530. A cylindrical through-bore or through-channel 535, extends axially along an axis L through the holding tool inner surface body 536, so as to join a first or top opening of the holding tool 530 and a bottom opening 537 located at the bottom portion 531.

Referring to FIG. 27, the holding tool 530 bottom portion 531 includes a arched cutout portion 538 wherein a portion of the outer surface 533 of the body 532 and inner surface 536 of the bore 535 are removed in order to provide a slot-shaped region or through-slot 539. The through-slot 539 is alignable with the receiver U-shaped channel 476, and is also sized and shaped to allow passage of the rod 421 therethrough, such as is described below. The through-slot 539 extends through the outer surface 533, such that the side walls 534 create an upside down U-shape or arch.

Additionally, the holding tool 530 also may include a radiused and inwardly directed projection or guide 543 sized and shaped to slideably engage and reversibly engage the tool engagement grooves 488 and 490 that are both commonly radiused to allow rotatable mating. The guide 543 is shown only on one side but it is foreseen that the guide 543 may be on opposite sides and may extend entirely around the interior 536 of both sides or just partially in which case the grooves 488 and 490 may be less than fully across the receiver arms 472 and 474. The guide 543 may also be slightly sloped relative to the grooves 488 and 490 to produce a camming effect when joined. The inner surface 536 is shown including an inner holding tool surface helically wound or partially helically wound guide and advancement structure 543 which may include conventional helical threads, helically wound square threads, or other guide and advancement structure sized and shaped to cooperate with complementary equivalent grooves 488 and 490 on the arms 472 and 474 of the receiver 410. It is foreseen that holding tool guide 543 may be configured in a variety of shapes and sizes and be disposed at other locations on the receiver arms 472 and 474. Outside of this guide, the through-bore 535 has a substantially smooth cylindrical inner surface 536 and is sized and shaped to threadably receive there through: the closure top 418 for closing the bone screw assembly 401, the retainer structure 412, and the bushing 550. The through-bore 535 is also sized so as to receive there through a closure installation tool 414 (shown in FIG. 19), and optionally additional tools, such as but not limited to a driving tool 580 (shown in FIG. 18) and a guide wire 407 (shown in FIG. 18).

As seen in FIG. 28, the holding tool 530 is rotatably attached to the receiver 410 having grooves 488 and 490 that receive the guide 543, using a twist on procedure. The holding tool 530 is turned or rotated so a through slot 539 faces the through gap 477 so as to provide a continuous path sized and shaped to receive the rod 421 there through (shown in FIG. 19). When the holding tool 530 is mounted on to receiver 410, the holding tool 530 extends around the upper portion 465 of the receiver 410, and the screw guide 543 contacts or abuts the arms 472 and 474 to properly position and align the guide 543 with the grooves 488 and 490. In the illustrated embodiment, the inner chamber surface 536 contacts the receiver 410 exterior surface 487. Additionally, the holding tool 530 guide 543 reversibly interlocks and mates with the tool engagement grooves 488 and 490 on the receiver 410, so as to secure the holding tool 530 and the bone screw assembly 401 together. It is foreseen that in some embodiments, portions the body inner surface 536 and side surface 534 adjacent to the through-slot openings 539 are beveled, slanted or partially conical, so as to guide, direct or assist in threading or passing an end of the rod 421 into the recess 541 of the through-slot 539.

Also located near the holding tool bottom 531 is a rod abutment relief surface 541 cutout from the side surface 534, that is sized and shaped for the purpose of bridging the rod 421 when the holding tool 530 is rotated for removal, as described elsewhere herein. When the rod 421 is through the through slot 539, the holding tool 530 can be manipulated to further align the shank 404 upper head portion 408 relative to the rod 421 prior to tightening and torquing of the closure top 418 via the closure installation tool 414 (shown in FIG. 19). It is understood that the holding tool 530 can be used in any embodiment of the invention and is not limited to this embodiment.

Referring to FIGS. 19-20, after assembling the polyaxial bone screw assembly 401 and inserting the assembly 401 into a bone member 405, a rod member 421 is placed in the tool slot 539 and thereafter placed into the receiver 410, past the gaps 477. Once the rod member 421 is placed in the receiver 410, the rod member 421 will rest only on the seat 553 of the bushing 550. The bushing 550 must remain at least slight above the U-shaped channel 476 to prevent the rod member 421 from bottoming out on the lower end 478 of the channel 476 and thus not being able to transmit a locking pressure from the rod member to the shank 404. Preferably, once the bushing 550 is fully installed, the bushing 550 applies light pressure to the ball 429, so that the shank 404 is positionable with respect to receiver, but not fully locked. The receiver is held in a substantially stiff position and not floppy relative to the shank 404, and can be manipulated by the surgeon. In embodiments in which the arms 472 and 474 of the receiver 410 include internal threads 482 (e.g., for mating with the external threads of the closure 418 having a bottom surface 558, the top of the rod member 421 preferably rests above the bottom of the lowest internal thread member to allow positive locking of the rod member 421. The rod member 421, when loaded and biased downwardly by the closure 418, is biased against the bushing 550, consequently biasing the shank 404 downwardly in a direction toward the base 470 of the receiver 410 when the bone screw assembly 401 is fully assembled to snug the shank 404 against the cavity 498 shaped wall 502 and thereby lock the position of the shank 404 relative to the retainer 410 due to friction therebetween. The shank 404 and retainer 412 are thereby locked or held in position relative to the receiver 410 by the rod 421 firmly pushing downward on the ball member 429 or flat upper surface 643.

It is foreseen that in some embodiments, the rod member 421 comprises a rectangular or cylindrical elongate structure, or any variety of implants utilized in spinal surgery. The rod member 421 is of uniform diameter and has a generally smooth surface 422. The rod member 421 can be made from metal, metal alloys or other suitable materials, including plastic polymers such as polyetheretherketone (PEEK), ultra-high-molecular weight-polyethylene (UHMWP), polyurethanes and composites.

Referring to FIG. 20, the closure structure 418 comprises: the bottom base surface 558, a generally cylindrical shaped body 563 comprising helically wound threads 561, a top surface 564, and an aperture 568 that is sized and shaped for operably receiving manipulating installation tool 414 (shown in FIG. 19), in a hex-shaped and axially aligned aperture 568 disposed into the top surface 564. The aperture 568 that is shown as sized and shaped for operably receiving a lower hex shaped manipulating installation tool 414 into the aperture 568 for rotating the closure structure body 563 subsequent to installation and to provide for removal thereof, if necessary. It is foreseen that the aperture 568 may take a variety of tool-engaging forms and may include one or more apertures of various shapes, such as a pair of spaced apart apertures, or a left hand threaded bore, or an easy-out engageable step down bore, or a Torx aperture, or a multi-lobular aperture or the like. The interior surface 569 shaped for the installation tool, shown is a hex shaped surface. It is foreseen that the closure structure 418 may include a break-off head (not shown), so as to break away at a preselected torque that is designed to properly seat the closure structure in the receiver. The closure structure or closure top can be constructed of any of a variety of different types of materials and cooperative closure structures for use in conjunction with the present invention with suitable mating structure on the upstanding arms 672 and 674.

In FIGS. 19-20, after seating the rod member 421 in the receiver 410, the cap screw or closure structure 418 is rotatably threaded down the holding tool through-bore 535 and through the first opening 507 of the receiver 410 to cover the top of the U-shaped channel 476 and captures the rod member 421 therein. The closure structure 418 comprises a cylindrical body 563 having external threads 561 capable of mating with the internal threads guide 482 of the arms 472 and 474. The closure structure 418 is rotated clockwise between the arms 472 and 474, so the threads thereof rotatably mate to drive the rod member 421 downwardly through the first upper opening 507 of the receiver 410 using the closure installation tool 414. The installation tool 414 with closure structure 418 therein is placed in the elongate through-bore 535 of the holding tool 530. The closure structure 418 is then driven by use of the installation tool 414 toward the rod member 421.

The closure structure 418 makes contact with a top surface 422 of the rod member 421, and applies downward pressure to the rod member 421 to create frictional forces between the rod member 421, the seat portion 753 of the bushing 550, which presses therethrough to the top portion 408 of the shank 404 and ball member 429. The closure structure 418 thus provides downward compressive forces that lock the shank 404 at a fixed angle with respect to the longitudinal axis G of the receiver 410. The shank top end surface 442 and retainer structure outer spherical surface 526, because they are rounded so as to approximately equally extend upward onto the bottom surface 555 of the bushing 550 no matter what degree of rotation exists between the shank 404 and receiver 410. The spherical ball 429 surfaces 442 or 526 are engaged by the rod 421 and pushed downwardly toward the base 470 of the receiver 410 when the closure structure 418 is rotated downwardly toward and onto the rod 421. The downward pressure on the shank 404 in turn urges the retainer structure 412 in a tighter mating fit. The retainer structure 412 that is thereafter rigidly attached to the shank 404 is in turn urged downwardly and becomes frictionally and rigidly attached to the receiver 410, fixing the shank body 406 in a desired angular configuration with respect to the receiver 410 and rod 421. The closure structure 418 therefore further provides downward compressive forces that lock the shank 404 at a fixed angle on axis F with respect to the longitudinal axis G of the receiver 410. It is foreseen that the guide and advancement structure 561 utilized in accordance with the present invention may take a variety of forms, including the illustrated substantially square thread and also those described in Applicant's U.S. Pat. No. 6,726,689, which is incorporated herein by reference.

It is noted that during assembly the shank 404 and retainer structure 412 have generally equally radiused mating surfaces so that the retainer structure 41 rotates into the shank 404 about a pivot and thereafter friction fits to form a cam lock or juncture therebetween to hold the retainer structure 412 to the shank 404.

After the assembly 401 is complete the holding tool 530 is rotated ninety degrees counterclockwise (see FIGS. 28-30) so that the recess 541 straddles the rod 421 to allow respective holding tool 530 and receiver 410 to detach or disengage from one another. The holding tool 530 is then pulled axially upward away from the shank 404. If removal of the assembly 401 and associated rod 421 and closure structure 418 is necessary, disassembly is accomplished by using the installation tool 414 mating with the aperture 568 and turned counterclockwise to rotate the base 558 and reverse the advancement thereof in the receiver 410. Then, disassembly of the assembly 401 is accomplished in reverse order to the procedure described previously herein for assembly.

With reference to FIGS. 30-36, the reference number 601 generally represents an embodiment of a polyaxial bone screw apparatus or assembly according to the present invention. The assembly 601 includes a shank 604 that further includes a threaded body 606 integral with an upper portion 608; a receiver 610; and a retainer structure 612. The shank 604, receiver 610 and retainer structure 612 preferably are factory assembled prior to implantation of the shank body 606 into a vertebra, but can also be assembled at the site of usage.

With further reference to FIG. 30, also shown is a closure structure 618 for biasing a longitudinal connecting member such as a rod member 621 indirectly against the shank upper portion 608 which biases the retainer 612 and the shank upper portion 608 into fixed frictional contact with the receiver 610, so as to fix the angular position of the shank 604 relative to the receiver 610 and fixes the position of the rod 621 relative to the vertebra (as seen similarly in FIG. 18). In particular, the rod member 621 rests on a bushing 750, which in turn rests on the top of the shank 604, as further described below. The receiver 610 and the shank 604 cooperate in such a manner that the receiver 610 and the shank 604 can be secured at any of a plurality of angles, articulations or rotational alignments relative to one another and within a selected range of angles both from side to side and from front to rear, to enable flexible or articulated engagement of the receiver 610 with the shank 604 during positioning until both are locked or fixed relative to each other near the end of an implantation procedure.

In some embodiments, to assemble the bone screw assembly 601, first the shank 604 is inserted into the receiver 610 through the bottom of the receiver 610 (shown in FIG. 32). Subsequently, the retainer structure 612 is slid into the receiver 610 from the top of the receiver 610 and mated with the mating portion 633 of the shank 604 to form a ball member 629 (shown in FIGS. 33-36) with an upper surface 643. Next, the bushing 750 is slid into the top of the receiver 610 over the spherical ball 629 formed by the shank 604 and the retainer 612 (shown in FIGS. 33-36) or the surface 643. The assembled shank 604, retainer structure 612 and receiver 610 are preferably then joined with a vertebra by screwing the shank body 606 into the vertebra or the like, such as a pedicle, ilium, or sacrum (as similarly shown in FIG. 18). It is foreseen that the shank 604 may first be screwed into the vertebra and then the retainer structure 612 and receiver 610 joined therewith, but normally these elements would be preassembled. Thereafter, a rod or elongate member 621 is provided to be coupled with the bone screw assembly 601. A cap screw or closure top or closure member 618 is downwardly inserted into the receiver 610 to apply a downward compression force on the rod (shown in FIG. 30). The force of the cap screw 618 on the rod 621 is transmitted to the bushing 750 and then to the ball 629 on surface 643 to bias the shank 604 against the receiver 610 to lock the shank 604 at a fixed angle by compressive forces.

Illustrated in FIG. 30, the shank 604 is elongate, with the shank threaded body 606 having a helically wound bone implantable thread extending from a neck 626 portion of the threaded body 606 located adjacent to the upper portion 608 to a tip (not shown) of the body 606 and extending radially outwardly therefrom. To provide a biologically active interface with the bone, the threaded shank body 606 may be coated, perforated, made porous or otherwise treated as previously mentioned.

The shank 604 is cannulated, having a small central bore 644 extending an entire length of the shank 604 along the axis P. The bore 644 is defined by an inner cylindrical wall 645 of the shank body 606; a second inner star shaped wall 711 in the shank head portion 608 with a larger outer radius; and two openings: a first circular opening (not shown) at the shank tip (not shown) and a second opening being a tool engagement aperture 640 in the shape of a star Allen wrench tool. The upper head portion 608 illustrated includes the tool engagement aperture 640 shown in a star shape and the top surface 643 (seen in FIG. 30). It is also foreseen that the top surface 643 may include recesses or apertures 640 for receiving numerous shapes of driving tools therein (not shown). A driving tool (as similarly seen in FIG. 18) is configured to fit about the tool engagement aperture 640 so as to form a socket and mating projection for both driving and rotating the shank body 606 into and reversibly from the vertebra (as similarly seen in FIG. 18). The bore 644 is coaxial with the threaded body 606 and through the upper head portion 608 of the shank 604. The bore 644 provides a passage through the shank 604 for a length of wire (as similarly seen in FIG. 18) inserted into the vertebra (as similarly seen in FIG. 18) prior to the insertion of the shank body 606.

Referring to FIGS. 30-36, the shank neck 626 extends axially upwardly from the shank body 606. The neck 626 may be of reduced radius as compared to an adjacent top portion 608 of the threaded body 606. Further extending axially upwardly from the neck 626 is the shank upper portion 608 that provides a capture cut out or mating segment surface 633 disposed at a distance from the threaded body 606 and thus at a distance from the vertebra when the body 606 is implanted in the vertebra (as similarly seen in FIG. 18). On the upper portion 608 of the shank 604, four shaped surfaces 634, 635, 636, 637 define the mating segment 633. First shaped surface 634 is semi-cylindrical in nature with a radius smaller than that of the outer spherical surface 642 corresponding difference being the thickness of the retainer structure 612. The first shaped surface 634 contours inward along its lowest section running perpendicular to a fourth shaped surface 637, following upward perpendicular to a third shaped surface 636, and running perpendicular to a second shaped surface 635 semi-circularly across two and a quarter scalloped semi-circles to meet at the top surface 643, and then is mirrored on the other side to cooperate with an inner surface 710 of the mating segment 728 of the retainer structure 612. Second shaped surface 635 is scalloped in nature connecting with the top surface 643 and third shaped surface 636 to cooperate with the top surface of the retainer structure 612 and then is mirrored on the other side. The third shaped surface 636 is a planar surface substantially or completely perpendicular with the top surface 643 and connects second shaped surface 635 to the fourth shaped shaped surface 637. The third shaped surface 636 cooperates with the prongs 720 of the retainer structure 612 and is mirrored on each side for this purpose. The fourth shaped surface 637 is parallel with the top surface 643 and the second shaped surface 635. The fourth shaped surface 637 faces the second shaped surface 635 and creates a seat for the retainer structure 612 bottom surface 714. The fourth shaped surface cooperates with the first shaped surface 634 by running perpendicular to the first shaped surfaces 634 bottom to the intersection of the first shaped surface 634 and the third shaped surface 636. It is foreseen these four surfaces 634, 635, 636, 637 could be any shape to cooperate and mate with retainer structure and create a ball-like surface with a top surface 643.

The first shaped wall 634 in one embodiment comprises a generally concave surface capable of receiving a matching convex surface. In some embodiments, the first shaped wall 634 can be convex and matched with a concave surface. While in general, the surface 634 of the mating segment 633 is smooth and mates with a like smooth surface, in some embodiments, the surface can be roughened to increase frictional mating between the mating segment 633 of the shank 604 and the mating segment 728 of the retainer structure 612.

The shank upper portion 608 is configured for a polyaxial connection between the shank 604 and the receiver 610 by capturing the shank 604 upper portion 608 in the receiver 610. The upper portion 608 of the shank 604 is preferably curved or dome-shaped surface 642 as shown in the drawings, for contact engagement or positive mating engagement with the bushing 750, when the bone screw assembly 601 is assembled and in any alignment of the shank 604 relative to the receiver 610. In certain embodiments, the top end surface 643 is smooth. While not required in accordance with practice of the invention, the surface 643 may be scored or knurled to further increase frictional positive mating engagement with the bushing 750.

Referring to FIG. 30, the receiver 610 has a generally U-shaped appearance with a partially cylindrical inner profile and a partially curved and partially faceted outer profile; however, the outer profile 687 could also be partially spherical. The receiver 610 has three portions: an upper portion 665, an intermediate portion 666, and a lower portion 667. A bore 704 is defined by interior surface 680 and extends from a first upper opening 707 to a second lower opening 708 along an axis Q. It is noted that at times, axis P, Q, and R coalign with each other. The bore 704 provides a passage through the receiver 610 for the bushing 750 and the retainer structure 612 as described below. In other embodiments, receiver 610 may include one or more of the features discussed above for receivers 10, 210, or 410.

The receiver 610 includes a somewhat curved or cylindrical base 670 integral with a pair of upstanding arms 672 and 674 forming a U-shaped cradle that defines a U-shaped channel 676 extending along an axis R transverse to the axis Q. The U-shaped channel 676 between the arms 672 and 674 creates gaps 677 and a lower seat 678 having substantially the same radius as the rod 621 for operably snugly receiving the rod 621 slightly spaced from the seat 678 of the channel 676. The rod member 621 is loaded downwardly in the first opening 707 and through the gaps 677, until the surface of the rod 621 rests near a bottom portion seat 678 of the U-shaped channel 676. The rod member 621 rests on the bushing 750, as the bushing 750 extends upward into the channel 676, as described below. In some embodiments, the U-shaped channel 676 has substantially the same radius as the rod member 621 so as to be capable of snugly receiving the rod member 621 on the outside surface 622 thereof, while it is foreseen that in other embodiments, the U-shaped channel 676 may have a slightly larger radius. The top of the rod member 621 when inserted in the U-shaped channel 676 is located at a lower end of the guide and advancement structure 682 formed on the arms 672 and 674 of the receiver 610.

Referring to FIG. 30, the arms 672 and 674 are generally symmetrical and shaped similarly, although in some embodiments one arm can be sized or shaped differently from another. Each of the arms 672 and 674 defines an interior surface 680 that forms the inner cylindrical profile of the receiver 610, and in this embodiment is a smooth surface. Interior surface 680 comprises a cylindrical body having a radius equal to the shortest distance between the inner wall of arms 672 and 674 and a point on the axis Q. The inner cylinder formed is not a continuous solid due to the gaps 677 formed between the arms 672 and 674. In the illustrated embodiment, the interior surface 680 includes a partial helically wound guide and advancement structure 682.

In the illustrated embodiment in FIG. 30, the guide and advancement structure 682 along the interior surface 680 is a partial helically wound interlocking flange form configured to mate under rotation with a similar structure on the closure structure 618, as described more fully below. However, it is foreseen that the guide and advancement structure 682 could alternatively be a square thread, a buttress thread, V-shaped threads, a reverse angle thread or other thread like or non-thread like helically wound advancement structure for operably guiding under rotation and advancing the closure top 618 downward between the arms 672 and 674 when rotated clockwise. In some embodiments, the internal threads or guide 682 comprise helically wound forms capable of interlocking with other surfaces as described in Applicant's U.S. Pat. No. 6,726,689, which is incorporated herein by reference in its entirety. Beneath the internal threads 682 is a thread relief 683. The thread relief 683 comprises a ledge member 693 located below the threads 682 and above the seat surface 678. The thread relief 683 serves to space the threads 682 from the seat surface 678 to ensure that a rod 421 resting on the seat surface 678 and/or bushing 750 seat is preferably completely beneath the lowest thread member.

Tool engaging aperture 685 and interior surfaces 686 are formed on or through exterior surfaces 687 of the arms 672 and 674 that may be used for holding the receiver 610 during assembly with the shank 604 and the retainer structure 612 and also during the implantation of the shank body 606 into a vertebra (shown in FIGS. 18-20). The aperture 685 can be used to couple with one or more holding instruments having protruding members or indentors. For example, in one technique, a protruding tab member of a surgical instrument can be received within the opening interior 686 to mate the surgical instrument with the receiver 610. While FIG. 30 illustrates a single opening 685 on one side of the receiver 610, it is foreseen that the receiver 610 can also include a second opening on the opposite side of the receiver. In other embodiments, a plurality of openings 685 can be provided around the surface 687 of the receiver so as to provide multiple receiving or coupling areas.

Furthermore, each of the arms 672 and 674 also includes a V-shaped or C-shaped undercut tool engagement groove 688 and 690, respectively, formed on outer surfaces 687 thereof which may be used for holding the receiver 610 with a holding tool (as similarly shown in FIGS. 18, 19, 27-29). The grooves 688 and 690 are radiused perpendicularly with respect to the axis G and are preferable horizonitally aligned. In the present embodiment, the grooves 688 and 690 extend internally from one side to the an opposite side of a respective arm 672 and 674. It is foreseen that the grooves 688 and 690 may only extend part way or be slightly sloped to produce a cam effect. The tool engagement grooves 688 and 690 form a shoulder that extends from one edge of an arm 672 adjacent a U-shaped channel 676 on one side of the receiver to a second edge of the arm 674 adjacent a U-shaped channel 676 on the other side of the receiver 610. In other embodiments, it is foreseen that the grooves 688 and 690 need not extend across the entire surface of an arm 672 from one edge to another. For example, one end of the shoulder can begin midway through the arm 672 and continue to edge of the arm 674. The grooves 688 and 690 have an inward or interior surface 684. The grooves 688 and 690 form a track feature on each arm 672 and 674. In some embodiments, an holding instrument having a protruding member can slideably engage and mate with the surface of the grooves 688 and 690 (shown in FIGS. 18, 19, 27-29). The holding instrument can be delivered down a sleeve and can be rotated so that its protruding segments are placed within the grooves 688 and 690, thereby providing a secure attachment between the holding instrument and the receiver 610 (as similarly shown in FIGS. 18, 19, 27-29).

The receiver 610 comprising additional exposed features, including rod relief flats 679, side groove 689, lip 692, and bottom curved surface 694. These exposed features may be useful for being grasped by instruments during a surgical procedure and/or for facilitating angulation of the shank 604 relative to the receiver 610. For example, the opening interior 686, shoulders 688 and 690, and side groove 689 can serve as instrument interfaces. An holding instrument (as similarly shown in FIGS. 18, 19, 27-29), such as a rod reducer, can be used to attach to the receiver 610 at one or more of the instrument interfaces. The instrument may include a mateable surface that mates with one or more of the exposed features of the receiver 610 in a suitable manner (e.g., by sliding or gripping).

In the illustrated embodiment, the receiver 610 includes rod relief flats 679 located along the edge of the arms 672 and 674 along the U-shaped channel 676. The rod relief flats 679 are external surfaces angled inwardly toward the top of the receiver 610. Due to the inward angle of the flats 679 on the side surface of the receiver 610, the seat surface 678 for rod placement is located at an inward position from the farthest projecting lip surface 692 on the side surface of the receiver 610. When a rod 621 is placed on the seat surface 678 such that the rod 621 extends beyond the seat surface, the inward position of the seat surface 678 (caused by the rod relief flats 679 being angled inwardly) helps to minimize the space occupied by the portion of the rod that extends beyond the receiver surface. For example, even when a rod member 621 extends beyond a seat surface 678, it is possible that the rod member 621 will not extend beyond the farthest projecting lip surface 692 on the side surface of the receiver 610.

In the illustrated embodiment in FIG. 30, the receiver 610 also includes an undercut region or groove 689, located beneath the U-shaped channel 676 seat surface 678. The groove 689 ceiling surface 691 or bottom ledge surface 691a can serve as an external grasping surface for an instrument. For example, in some embodiments, an instrument having a gripping member may grasp the receiver 610 at the groove 689.

The receiver 610 also includes bottom curved surface 694. The bottom curved surface 694 is a inwardly curved section of the receiver 610. The bottom of the curved surface 694 meets at the base 670 of the receiver 610. The bottom curved surface 694 accommodates the spherical ball connection (formed by joining the shank 604 as seen in FIG. 32-36 with the retainer structure 612) when it is positioned within the receiver 610. The bottom curved surface 694 provides for the maximum angulation of the spherical ball connection prior to locking the spherical ball connection at a particular angle.

In the illustrated embodiments of FIGS. 31-36, the bottom-loaded bone screw or shank 604 can be upwardly loaded into the interior 680 of the receiver 610. Partially continuous inner recesses 699 and 700 formed on the interior surface 680 beneath the wound guide and advancement structure 682 and the thread relief 683. In the illustrated embodiment, the inner recesses 699 and 700 comprise substantially cylindrical inner walls 701 and 702 that form a partially continuous cylinder having a radius larger than the radius of the cylindrical shape formed by the interior surface 680 of the receiver 610. The inner recess 699 and 700 are sized and shaped to receive protrusions 757' and 759' of a bushing 750 (as described later). A ridge upper surface 695 mirrored on both sides with an a forward surface 696 and an under surface 697 to mate with recesses 788 and 792 in protrusions 757' and 759' of the bushing 750. In some embodiments, the inner recesses 699 and 700 can be rectangularly shaped or form a continuous cylinder. In other embodiments, the inner recesses 699 and 700 can comprise a rounded recess that does not form a cylinder. In some embodiments, the interior of the receiver 610 can be modified to replace spherical cut-out recesses 699 and 700 with rectangular or angular cut-outs. By providing slots that are of rectangular shape, e.g., where there are two walls to restrict the motion of the shank 606 to one plane.

Referring to FIGS. 31-36, communicating with and located directly above the second opening 708 of the receiver 610 is a chamber or cavity 698. The cavity 698 communicates upwardly into the bore 704 and downwardly to the second opening 708. The cavity 698 is defined by a inner partially continuous cylindrical shaped walls 701 and 702. In some embodiments, the partially continuous shaped walls 701 and 702 transition into the inner shaped wall of a restrictive neck (not shown). In one embodiment, a shaped wall 703 is tapered inward and forms an inverted conical surface that has a cross-sectional radius smaller than the cylinder formed by the interior 680. In some embodiments, the interior of the shaped wall 703 is rounded. In the illustrated embodiment, the shaped wall 703 is sized and shaped for mating with the head portion 608 of the shank 604, which is uploaded into the cavity 698 through the lower opening 708 where the shank 604 mates with retainer 612 to form the ball 629 which has a larger diameter than the opening 708 so as to secure the shank 604 in the receiver 610, but allow polyaxial rotation of the shank 604 relative to the receiver 610 during positioning and until later locked. The retainer structure 612 polyaxially rotates with the shank 604 relative to the receiver 610 during positioning.

It is foreseen in some uses, prior to insertion through the second opening 708 of the receiver 610, the shank 604 is kept in coaxial alignment with the longitudinal axis Q of the receiver, while in other embodiments, the shank 604 is kept at an angle from the longitudinal axis Q of the receiver 610, such as between 1 and 90 degrees, or between 25 and 70 degrees. The shank 604 is preferably inserted vertically through the second opening 708 (shown in FIG. 31). Using a cut-away portion surface 703 of the receiver 610 to seat the shank 604, the shank 604 can be angulated (if not angulated already) or more precisely angulated (if angulated already) such that the shank 604 is aligned at an angle between 30 and 60 degrees, more preferably about 45 degrees, such that the upper head portion 608 of the shank 604 rests firmly against the cut-away portion surface 703 of the receiver 610 (shown in FIG. 32). When the shank 604 is appropriately angulated within receiver 610, a retainer structure 612 can be downwardly deposited or top-loaded through the receiver 610 to mate with the head portion 608 of the shank 604 to form a spherical ball 629 with a top surface 643.

Referring to FIG. 30, the retainer structure 612, has an operational central axis S that is the same as the rotational axis P associated with the shank 404 and can be aligned or non-aligned with the axis Q associated with the receiver 410, but when the retainer structure 612 is separated from the shank 604, the axis of rotation is identified as axis S.

Illustrated in FIG. 30, the retainer structure 612 comprises an inner surface 710, a top surface 712, a bottom surface 714, a pair of protrusions 718 and 720, a second partial spherical outer portion 726, and a second mating segment 728. The protrusions 718 and 720 extend from each side of retainer structure 612 which comprises a convex mating surface. The protrusions 718 and 720 and the inner surface 710 make up the second mating segment 728.

Illustrated in FIGS. 31-36, the protrusions 718 and 720 have a forward surface 716 that are each sized and shaped to mate with the mirror images of the third shaped wall 636 on the head portion 608 of the shank 604 when the retainer structure 612 is joined, cam locked or snap fitted into place with the shank 604 in the receiver 610. Joining the retainer structure 612 and the upper head portion 408 of the shank 404 also results in a fitting contact between the concave surface of the first shaped wall 634 and the convex surface of the inner surface 710 of the retainer structure 612. Whereas when mated, the top surface 712 comes into fitting contact along the second scalloped edge of the second shaped surface 635 only, defining an aperture 713 created by a gap between the top surface 712 of the retainer structure 612 and the second shaped surface 635. The aperture 713 can be made to be in any shape, its purpose to create an aperture deep enough for a tool (not shown) to remove the retainer structure 612 from the shank 604 head portion 608 in disassembly. The bottom surface 714 of the retainer structure 612 comes into fitting contact and mates with the fourth shaped surface 637 when locked. When joined together, the retainer structure 612 and shank 604 form a large sphere 629 with a flat upper surface 643 that is engageably mated with the lower inner rounded surface 755 of the bushing 750. The retainer 612 is not joined with the shank 604 until both are in the receiver 610. This allows the shank 604 to be uploaded through the lower opening 708 in the receiver 610, as the shank 604 upper portion 608 fits through the opening 708 when not joined with the retainer structure 612, but the ball 629 created by the joining of the shank 604 and the retainer 612 has a larger diameter than the lower opening, thereby capturing the shank 604 in the receiver 610.

FIG. 31 illustrates a side view of a partially assembled polyaxial bone screw assembly 601 in which the shank 604 has been uploaded through the second opening 708 at the base of the receiver 610. FIG. 32 shows the upper head portion 608 of the shank 604 is in contact with interior wall 703 and is ready to receive and join with the retainer structure 612. In contrast to the shank 604 which was bottom-loaded through the receiver 610, the retainer structure 612 is preferably top-loaded through channel 676 of the upper surface of the receiver 610 (illustrated in FIG. 32). This may require some twisting or rotating, depending upon the angle by which the shank 604 is bottom-loaded. The retainer structure 612 is initially delivered into the receiver 610 in such a manner that the retainer structure 612 may make frictional contact with the interior surface 680 of the receiver 610.

FIG. 33 is a partially cross-sectional view of an assembled polyaxial bone screw assembly 601 comprising the receiver 610, the shank 604, and the retainer structure 612. The rounded upper head portion 408 can make firm contact with the shaped wall 703. In FIG. 35 the retainer structure 612 has been delivered downwardly or top-loaded through a first opening 707 at the top of the receiver 610. The retainer structure 612 makes contact with the upper head portion 608 of the shank 604 and is then joined or snap fitted into place to form the spherical ball member 629. Once the retainer structure 612 and shank 604 are locked into place, the bushing 750 is locked downwardly through the top of the receiver as shown in FIG. 33. The bushing 750 is used to capture the shank 604 upper portion 608 and retain the upper portion 608 within the receiver 610.

Referring back to FIG. 30, in the illustrated embodiment, the bushing 750 includes an upper surface 751, an exterior surface 754, a lower spherical surface 755, a central bore 772, and a flat exterior arched surface 785. The lower rounded surface 755 is rounded to mate with the spherical ball 629 mated upper shank portion 608 and flat surface 643 and outer surface 726 of the retainer structure 612 and thereby capturing them in the receiver 610. In addition, the bushing 750 further comprises U-shaped channel 776 between the arms 757 and 759 that create gaps 777 and a lower seat 753 having substantially the same radius as the rod 621 for operably snugly receiving the rod 621. The seat 753 of the bushing 750 in this embodiment substantially matches the shape and size of the bottom surface 678 of the U-shaped channel 676 of the receiver 610, such that the two can be aligned to allow a rod member 621 to be delivered into the seat 753 and bottom surface 678 of the U-shaped channel 676 of the receiver 610. A bore 772 is defined by interior surface 773 and extends from a first upper opening 774 to a second lower opening 775 along an axis T. The bore 772 provides a passage through the bushing 750 for driving the shank 604 into a bone, for a guide wire (not shown) or access to the retainer structure 612. Preferably, once the bushing 550 is fully installed, the bushing 550 applies light pressure to the ball 429, so that the shank 404 is frictionally or snugly positionable with respect to receiver 610, but not fully locked. The receiver 610 is held in a substantially stiff position and not floppy relative to the shank 404, and can be manipulated by the surgeon. In embodiments in which the arms and of the receiver include internal threads (e.g., for mating with the external threads of the closure having a bottom surface, the top of the rod member preferably rests above the bottom of the lowest internal thread member to allow positive locking of the rod member.

In the illustrated embodiment, pairs of outwardly extending protrusions 757', 757", 759', and 759" on the exterior surface 785 are rounded with a cylindrical, convex outer surface. In the illustrated embodiment, protrusions 757', 757", 759', and 759" are sized and shaped so as to fit into the recesses 699 and 700 of the receiver 610. In between the pairs of protrusions 757', 757", 759', and 759" lie recesses 788 and 792, each with a top surface 789 and 793, a pair of bottom surfaces 790 and 794, and a pair of back surfaces 791 and 795. One skilled in the art will appreciate that the protrusions 757 and 759 can be of various shapes and sizes. In some embodiments, bushing 750 may comprise one of the bushings or incorporate one or more of the bushing elements described or covered in U.S. Pat. No. 7,377,923 and U.S. patent application Ser. No. 12/290,244, which are incorporated herein by reference in their entireties.

Illustrated in FIG. 35 is a side view of a polyaxial bone screw assembly 601 prior to placement of the bushing 750 downwardly into the receiver 610. The flat arched surface 785 allows for the bushing 750 to slide through the interior 680 of the receiver 610. In some embodiments, the bushing 750 is initially oriented such that the pairs of outwardly extending protrusions 757', 757", 759', and 759" face the gaps 677 formed by the arms 672 and 674 of the receiver 610 (shown in FIG. 36). The bushing 750 is then slideably deposited downwardly through the top opening 707 of the receiver 610 and along the gaps 677 until the lower inner rounded surface 755 rests firmly on the spherical ball member 629.

Referring to FIG. 36, once the bushing 750 has been positioned such that its lower rounded surface 755 rests on the outer surface 642 formed by the shank 604 and the retainer structure 612, the bushing 750 is then rotated until the pairs of protrusions 757', 757", 759', and 759" are received into the pairs of recesses 699 and 700 and the pair of ridge upper surfaces 695 mate with the upper surfaces 789 and 793 of recesses 788 and 792 of the bushing 750 to thereby finally position the bushing axially while allowing slight vertical movement to apply pressure to the bushing 650. This also secures the bushing 650 in the receiver 612. In particular, fit the pairs of protrusions 757', 757", 759', and 759" into the recesses 699 and 700, the bushing 750 is rotated 90 degrees, thereby securing the bushing 750 relative to the receiver 610. The bushing 750 is rotated into place using an instrument or automated using a fixture, which is normally done at a factory. It is foreseen that in some embodiments, the bushing 750 can include one or more additional protrusions (not shown) in addition to the protrusions 757', 757", 759', and 759" on the outer wall of the bushing 750 that will cause an interference fit with the interior surface 680, when the bushing 750 is rotated into place. These additional protrusions can assist in preventing the bushing 750 from rotating under normal loading conditions.

FIG. 36 is a cross-sectional view of a fully assembled polyaxial bone screw assembly 601 comprising the receiver 610, the spherical ball member formed by a mated shank 604 with retainer structure 612 and a bushing 750 with upper surface 643. The bushing 750 has been rotated about 90 degrees relative to initial loading, such that the pair of protrusions 757', 757", 759', and 759" of the bushing 750 fit into the recesses 699 and 700 of the receiver 610. The spherical ball 629 joint rests on the interior wall 680 of the lower portion 667 of the receiver 610 and is capable of multi-axial rotation and angulation. While the degree of angulation can vary, it is foreseen that in some embodiments, the spherical ball 629 joint is capable of angulation (e.g., between 1 and 90 degrees) in many different directions.

It is possible to disassemble the bone screw assembly 601 by counterclockwise rotating the bushing 650 and removing the frictional bond between the bushing 750 and the shank 604. An aperture (as similarly shown in FIG. 20), in any shape, can be provided in the bushing 750 that will allow an external instrument to engage with the bushing 750 to facilitate disengagement between the bushing 750 and the shank 604. An aperture 685 can be located in the outside of the receiver 610 such that an instrument can extend through the opening 685 and press a top portion of the bushing 750, thereby severing a clip that reduces the friction between the bushing 750 and the shank 604. In other embodiments, a opening (not shown) can be placed in the inner wall of the receiver 610 such that an instrument (not shown) can enter through the interior 680 of the receiver 610 to rotatably remove the bushing 750 from the shank 604. The instrument can then pull the bushing 750 away from shank 604 to reduce the friction. It is foreseen in other embodiments, a first instrument (not shown) can be provided that has the shape of the bushing seat 753 and a second instrument (not shown) can be provided that holds the receiver 610 rigid, while the first instrument (not shown) is used to rotate the bushing by 90 degrees, thereby reversing the assembly process and disengaging the bushing 750 from the assembly 601. Thus, using the disassembly methods described above, it is possible to restore the variable angular capability of the shank 604.

After assembling the polyaxial bone screw assembly 601 and inserting the assembly 601 into a bone member (as similarly shown in FIGS. 18 and 19), a rod member 621 is positioned in the receiver 610 through the through the channel 676 along the axis Q aligned between the gaps 677. Once the rod member 621 is placed in the receiver 610, the rod member 621 will rest only on the seat 753 of the bushing 750. The bushing 550 must remain at least slight above the U-shaped channel 676 to prevent the rod member 621 from bottoming out on the lower end 678 of the channel 676 and thus not being able to transmit a locking pressure from the rod member to the shank 604. In embodiments in which the arms 672 and 674 of the receiver 610 include internal threads 682 (e.g., for mating with threads 761 of the closure 618 having a bottom surface 758), the top surface 622 of the rod member 621 can rest above the bottom 758 of the lowest internal thread member 761 of the closure 618 to allow for sliding of the rod or below the second to lowest internal member to allow positive locking of the rod member 621. The rod 621, when loaded and biased downwardly by the closure 618, is biased against the bushing 750, consequently biasing the shank 604 downwardly in a direction toward the base 670 of the receiver 610 when the bone screw assembly 601 is fully assembled to snug the shank 604 against the retainer 610 cavity 698 and thereby lock the position of the shank 604 relative to the retainer 610 due to friction therebetween. The shank 604 and retainer 612 are thereby locked or held in position relative to the receiver 610 by the rod 621 firmly pushing downward on the ball member 629.

It is foreseen in some embodiments, the rod member may be rectangular or cylindrical elongate structure, or any variety of implants utilized in spinal surgery. The rod member 621 is of preferably of uniform diameter whereat the rod member 621 is located in the receiver 612 and has a generally smooth surface. The rod member 621 can be made from metal, metal alloys or other suitable materials, including plastic polymers such as polyetheretherketone (PEEK), ultra-high-molecular weight-polyethylene (UHMWP), polyurethanes and composites.

Referring to FIG. 30, the closure or closure structure 618 comprises: a generally cylindrical shaped body 763 comprising helically wound threads 761, a bottom base surface 758, a top surface 764, and a bore 769. The bore in the bushing 769 is defined by interior surface 773 and extends from a first upper opening 774 to a second lower opening 775 along an axis U. The first upper opening or aperture 774 that is shown as sized and shaped for operably receiving a star shaped manipulating installation tool (as similarly seen in FIG. 19) into the aperture 774 for rotating the closure structure body 763 subsequent to installation so as to provide for removal thereof, if necessary. It is foreseen that the aperture 774 may take a variety of tool-engaging forms and may include one or more apertures of various shapes, such as a pair of spaced apart apertures, or a left hand threaded bore, or an easy-out engageable step down bore, or a Torx aperture, or a multi-lobular aperture or the like. The interior surface 773 is axially aligned with axis U and shaped for the installation tool, shown is a star shaped surface interior 773 all the way through the closure structure 618 to the second lower opening 775. It is foreseen that the closure structure may include a break-off head (not shown), so as to break away at a preselected torque that is designed to properly seat the closure structure in the receiver 610. The closure structure 618 can be construed of any of a variety of different types of materials closure structures for use in conjunction with the present invention with suitable mating structure on the upstanding arms 672 and 674.

After positioning the rod member 621, the closure structure 618 is rotatably threaded down a holding tool through-bore (not shown) or just through the first opening 707 of the receiver 610 to cover the top of the U-shaped channel 676 and capture the rod member 621 therein. The closure structure 618 comprises a cylindrical body 763 having external threads 761 on the closure body 763 capable of rotatably engaging and interlocking with the internal threads guide 682 of the arms 672 and 674, to provide for rotating advancement of the closure structure 618 into the receiver 610 when rotated clockwise and, in particular, to cover the top portion 665 or the upwardly gap 677 of the U-shaped channel 676 in order to capture the rod 621 without splaying of the arms 672 and 674. The closure structure 618 can be rotated relative to the arms 672 and 674, so the threads thereof rotatably mate to the drive the rod downwardly through the first upper opening 707 of the receiver 610 and is driven by using a closure installation tool (as similarly shown in FIG. 19) toward the rod 621 and thread relief 683.

The closure structure 618 makes contact with a top surface 622 of the rod member and applies downward pressure to the rod member 621 to create downward forces between the rod member 621, the seat portion 753 of the bushing 750, which passes therethrough to the top portion 608 of the shank 604. The shank top end surface 442 and retainer structure outer spherical surface 726, are rounded so as to approximately equally extend upward into the cavity 698 no matter what degree of rotation exists between the shank 604 and receiver 610. The spherical ball 629 surfaces 642, 726 or surface 643 are engaged by the rod 621 and pushed downwardly toward the base 670 of the receiver 610 when the closure structure 618 is rotated downwardly toward and onto the rod 621. The downward pressure on the shank 604 in turn urges the retainer structure 612 in a tighter mating fit awith the shank 604. The retainer structure 612 that is thereafter rigidly attached to the shank 604 is in turn urged downwardly and becomes frictionally and rigidly attached to the receiver 610, fixing the shank body 606 in a desired angular configuration with respect to the receiver 610 and rod 621. The closure structure 618 thereafter provides further downward compressive forces that lock the shank 604 at a fixed angle on axis P with respect to the longitudinal axis Q of the receiver 610. It is foreseen that the guide and advancement structure 761 utilized in accordance with the present invention may take a variety of forms, including the illustrated substantially square thread and also those described in Applicant's U.S. Pat. No. 6,726,689, which is incorporated herein by reference. A holding tool, as described above can be used in the installation of the closure structure 618.

If removal of the assembly 601 and associated rod 621 and closure structure 618 is necessary, disassembly is accomplished by using an installation tool (as similarly seen in FIG. 19) mating with the aperture 774 and turned counterclockwise to rotate the body 763 of the closure structure 618 and reverse the advancement thereof in the receiver 610. Then, disassembly of the assembly 601 is accomplished in reverse order to the procedure described previously herein for assembly.

It is to be understood that while certain forms of the present invention have been illustrated and described herein, it is not to be limited to the specific forms or arrangement of parts described and shown.

What is claimed is:

1. A polyaxial bone screw assembly for fixation to a bone, the assembly including a shank with a threaded body and an upwardly extending head portion, a retainer structure sized and shaped to join and polyaxially rotate with the shank, and a receiver that operably receives the head portion and retainer, the assembly further wherein:
   a) the head portion comprising a retainer engagement portion including a partially circumferential curvate groove with contoured upper and lower mating surfaces and a pair of spaced recesses;
   b) the retainer structure being sized and shaped to matingly engage the retainer engagement portion so as to form a substantially spherical ball-shaped pivoting surface with the head portion, the retainer structure comprising
      i) top and bottom mating surfaces complementary contoured for mating with the head portion upper and lower mating surfaces; and
      ii) a pair of spaced prongs sized and shaped to matingly engage the head portion recesses;
   c) the receiver defining an open channel and having a base with a lower seating surface partially defining a cavity, the seating surface being sized and shaped to engage at least a portion of upper head portion, the open channel communicating with the cavity, the cavity communicating with an exterior of the base through an opening sized and shaped to receive the shank upper head portion by uploading the upper head portion through the opening, where the upper head portion mates with the retainer within the cavity.

2. The assembly according to claim 1 including a pressure insert that pivotably engages the shank head portion comprising:
   i) a lower body with a pair of spaced opposed partially cylindrical surfaces and a pair of spaced vertical faces; and
   ii) a pair of opposed upwardly extending arm structures, each arm structure having a radially extending protrusion with a centrally located locking slot, the cavity of the receiver having an interior wall having a protrusion that mates with locking slot.

3. A polyaxial bone screw assembly for fixation to a bone, the assembly including a shank with a threaded body and an upwardly extending head portion, a retainer structure sized and shaped to matingly engage the head portion, a receiver pivotally engaging the head portion, and an upper pressure insert receivable in the receiver and pivotably engaging the head portion, the improvement comprising:
   a) the head portion having a retainer engagement portion including a partially circumferential curvate groove with contoured upper and lower mating surfaces and a pair of spaced locking recesses;
   b) the retainer structure being sized and shaped to matingly engage the retainer engagement portion so as to form a substantially spherical ball-shaped pivoting surface with the head portion, the retainer structure comprising
      i) top and bottom mating surfaces complementary contoured for mating with the head portion upper and lower mating surfaces; and
      ii) a pair of spaced prongs sized and shaped to matingly engage the head portion locking recesses;
   c) the upper pressure insert comprising
      i) a lower body with a pair of spaced opposed partially cylindrical surfaces and a pair of spaced vertical faces; and
      ii) a pair of opposed upwardly extending arm structures, each arm structure having a radially exteding protrusion with a centrally located locking slot; and
   d) a receiver having
      i) two spaced apart arms each being inwardly threaded and defining a gap therebetween,
      ii) a U-shaped channel extending along a second axis transverse to the first axis adapted to receive a rod member,
      iii) a first opening and a second opening extending along the first axis,
      iv) a cavity within the first opening and the second opening, the second opening being sized and shaped to provide for uploading the shank upper head portion therethrough, the shank upper head portion mating with the retainer within the cavity;
      v) a shaped wall, the wall being sized and shaped to slidingly at least partially engage the spherical ball member during positioning, and
      vi) below the threads of the two spaced apart arms are formed two protrusions that operatively connect with the locking slot of the pressure insert.

4. The assembly of claim 3, wherein the retainer further includes an external surfaces angled inwardly toward the top of the receiver located on the edge of the arms along the U-shaped channel.

5. The assembly of claim 3, wherein the
retainer further includes an exterior surface, along the exterior surface is an aperture defining an interior surface.

6. A polyaxial bone screw assembly for fixation to a bone, the assembly including a shank with a threaded body and an upwardly extending head portion, a retainer structure sized and shaped to matingly engage the head portion, a receiver pivotally engaging the head portion, and an upper pressure insert receivable in the receiver and pivotably engaging the head portion, the improvement comprising:
   a) the head portion comprising a retainer engagement portion including a partially circumferential curvate groove with contoured upper and lower mating surfaces and a pair of spaced locking recesses;
   b) the retainer structure being sized and shaped to matingly engage the retainer engagement portion so as to form a substantially spherical ball-shaped pivoting surface of the head portion, the retainer structure comprising:
      i) top and bottom mating surfaces complementary contoured for mating with the head portion upper and lower mating surfaces; and ii) a pair of spaced prongs sized and shaped to matingly engage the head portion locking recesses;

c) the upper pressure insert comprising:
  i) a lower body with a pair of spaced opposed partially cylindrical surfaces and a pair of spaced vertical faces; and
  ii) a pair of opposed upwardly extending arm structures, each arm structure having a radially extending protrusion with a centrally located locking slot; and d) the receiver having an upper portion, an intermediate portion, and a lower portion and defining a first axis extending between the upper and lower portions, the receiver having a first opening at the upper portion and a second opening at the lower portion, the upper portion comprising two spaced apart arms each being inwardly threaded and defining a gap therebetween, the upper portion further comprising a U-shaped channel extending along a second axis transverse to the first axis and adapted to receive a rod member, the lower portion of the receiver having a lower restrictive neck below a cavity formed therein, and the intermediate portion comprising a substantially cylindrical inner wall with a protrusion that mates with the locking slot of the pressure insert, located below the two spaced apart arms and above the lower restrictive neck.

7. A shank and retainer assembly for a bone screw wherein:
a) the shank has a lower threaded portion for implantation in a bone of a patient and an upper portion; the shank upper portion includes a first partial sphere; and
b) the retainer compress a second partial sphere whereby mating of the first and second partial sphere during mating forms a combined substantially ball shaped pivot structure.

8. The assembly according to claim 7, wherein the first partial sphere includes a concave region and the second partial sphere includes a convex region that mates with the concave region.

* * * * *